United States Patent [19]

Jasinski

[11] Patent Number: 4,863,572

[45] Date of Patent: * Sep. 5, 1989

[54] CORROSION PROBE AND METHOD FOR MEASURING CORROSION RATES

[75] Inventor: Raymond J. Jasinski, Tulsa, Okla.

[73] Assignee: Cities Service Oil and Gas Corporation, Tulsa, Okla.

[*] Notice: The portion of the term of this patent subsequent to Jun. 21, 2005 has been disclaimed.

[21] Appl. No.: 182,869

[22] Filed: Apr. 18, 1988

Related U.S. Application Data

[63] Continuation of Ser. No. 903,036, Aug. 29, 1986, Pat. No. 4,752,360, which is a continuation-in-part of Ser. No. 740,497, Jun. 3, 1985, abandoned, which is a continuation-in-part of Ser. No. 646,236, Aug. 31, 1984, abandoned.

[51] Int. Cl.$^4$ .......................................... G01N 27/46
[52] U.S. Cl. ........................... 204/1 T; 204/404; 324/65 CR
[58] Field of Search ................ 204/1 C, 1 T, 404; 324/65 CR

[56] References Cited

U.S. PATENT DOCUMENTS

| | | | |
|---|---|---|---|
| 3,331,021 | 7/1967 | Marsh et al. | 324/71.1 |
| 3,337,440 | 8/1967 | Nestor | 204/404 |
| 3,361,660 | 1/1968 | Chittum et al. | 204/404 |
| 3,406,101 | 10/1968 | Kilpatrick | 204/1 T |
| 3,436,320 | 4/1969 | Marsh | 204/1 T |
| 3,486,996 | 12/1969 | Annand | 204/404 |
| 3,518,530 | 6/1970 | Wilson | 324/323 |
| 3,910,830 | 10/1975 | Mayse | 204/404 |
| 3,980,542 | 9/1976 | Winslow, Jr. et al. | 204/404 |
| 3,996,124 | 12/1976 | Eaton et al. | 204/404 |
| 4,040,931 | 8/1977 | Wilson | 204/404 |
| 4,752,360 | 6/1988 | Jasinski | 204/1 T |

Primary Examiner—Aaron Weisstuch
Attorney, Agent, or Firm—John W. Carpenter

[57] ABSTRACT

A corrosion probe having in combination at least one first, at least one second, and at least one third electrode. A dielectric is positioned between the electrodes, and the dielectric has a structure defining an ionically conductive surface. An apparatus for measuring the corrosion rates of metals, or the like, in a corrosive liquid environment comprising the corrosion probe, a potentiostat electrically attached to the electrodes of the corrosion probe, and a signal generator electrically communicating with the potentiostat. The apparatus also has a voltmeter and an ammeter. A process for measuring the corrosion rates of metals in a corrosive liquid environment comprising attaching electrically the corrosion probe to a potentiostat. The corrosion probe is inserted into the corrosive liquid environment and either a predetermined known current is signaled to the potentiostat or a predetermined known difference in potential is signaled to the potentiostat. The potentiostat transmits the current, or applies the difference in potential, to the corrosion probe. An electromotive force between the first electrode and an area in the corrosive liquid environment in general microscopic proximity to the first electrode is determined. The corrosion current is computed from the determined electromotive force and the measured current. The probe may be utilized to detect electrochemically active components in a generally nonionic conductive fluid.

16 Claims, 20 Drawing Sheets

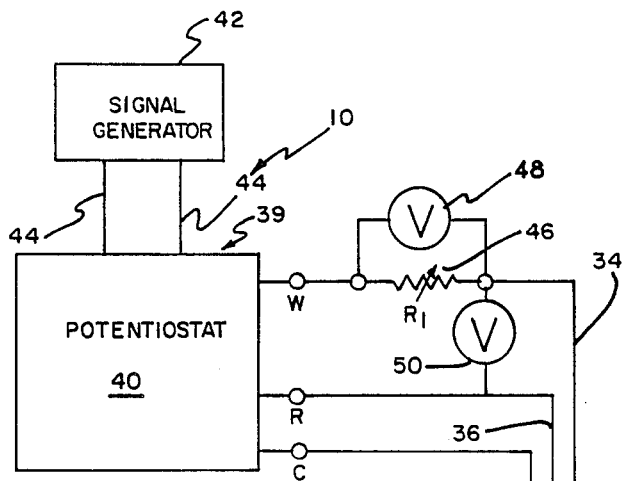
FIG. 1
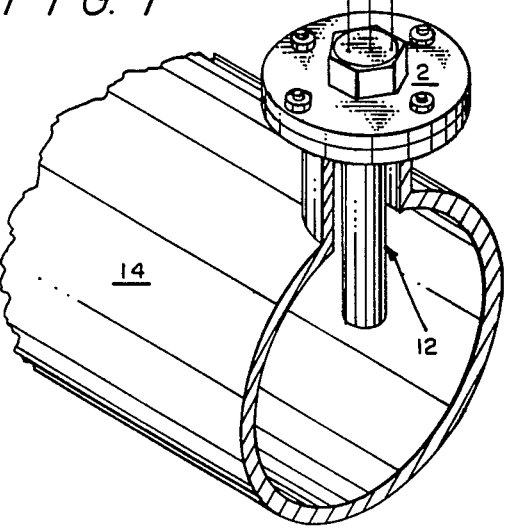
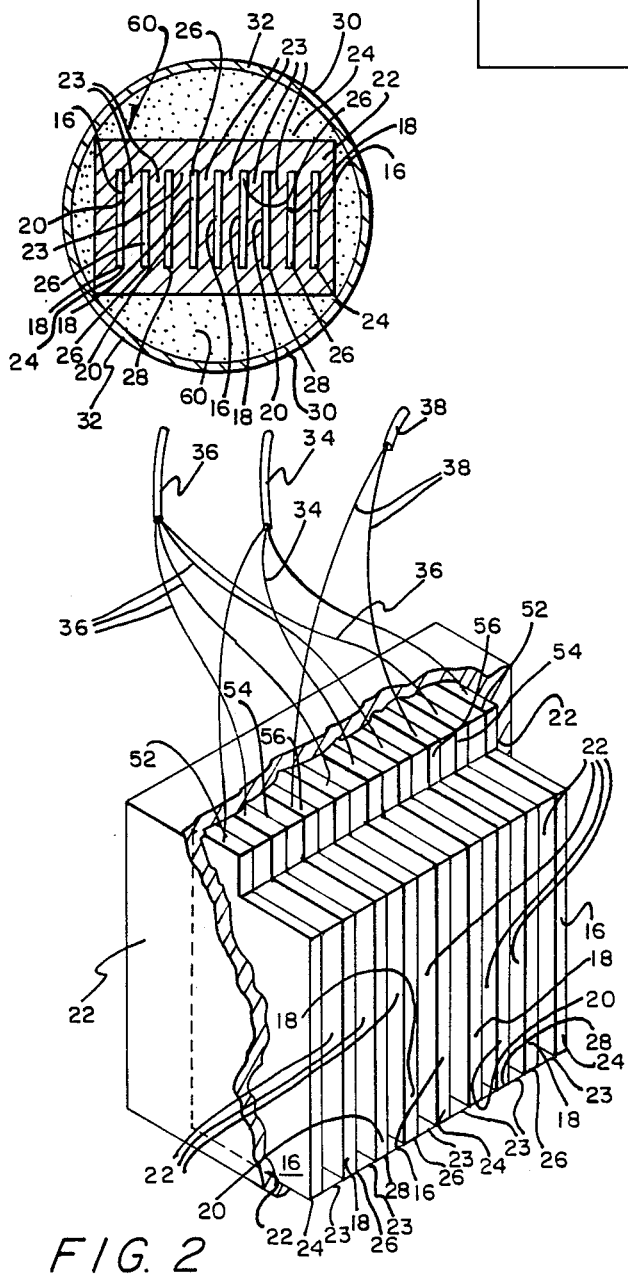
FIG. 3
FIG. 2
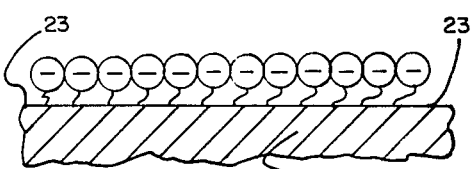
FIG. 4
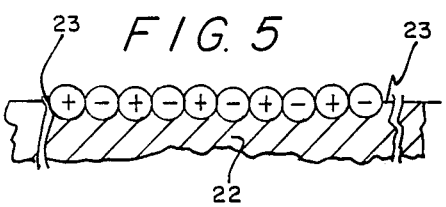
FIG. 5

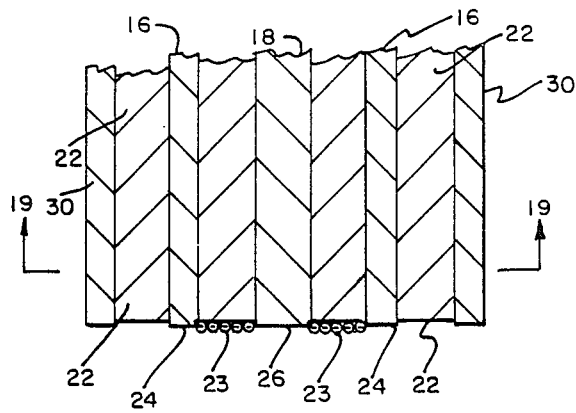
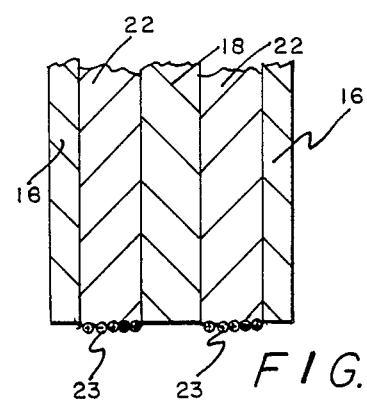
FIG. 16
FIG. 17
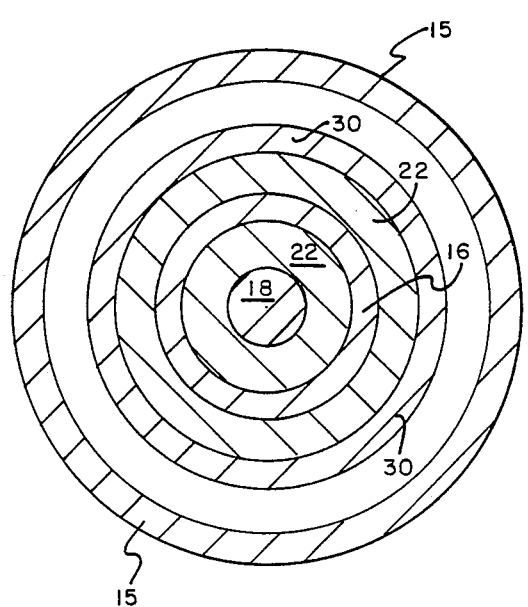
FIG. 18
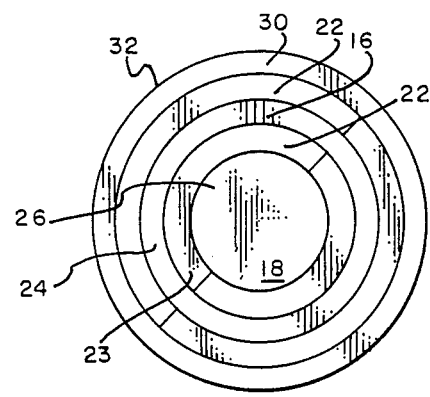
FIG. 21
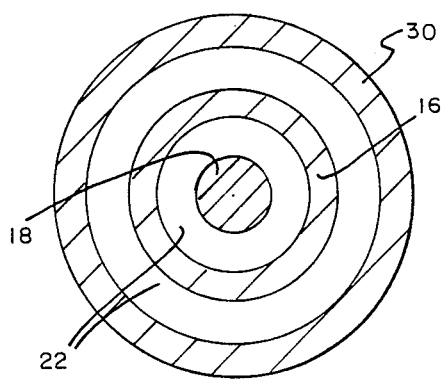
FIG. 19
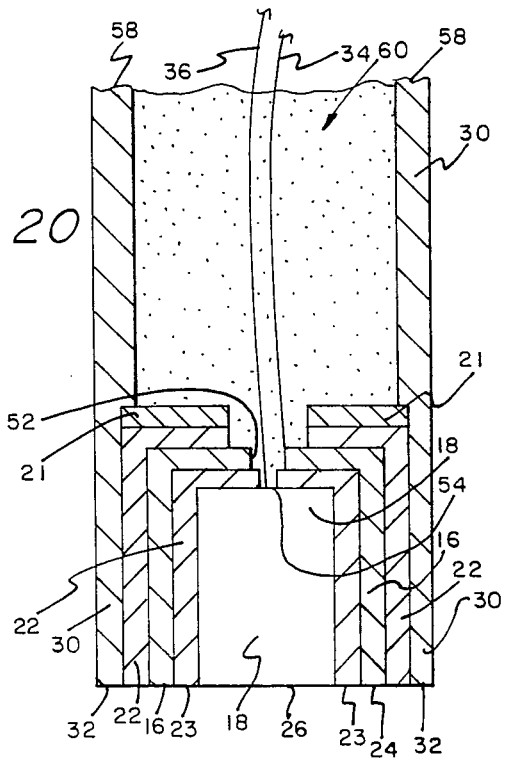
FIG. 20

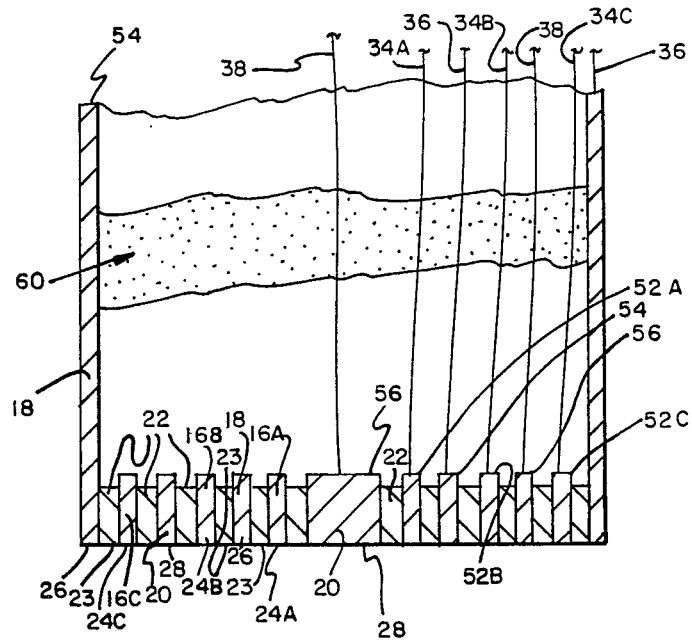
FIG. 32
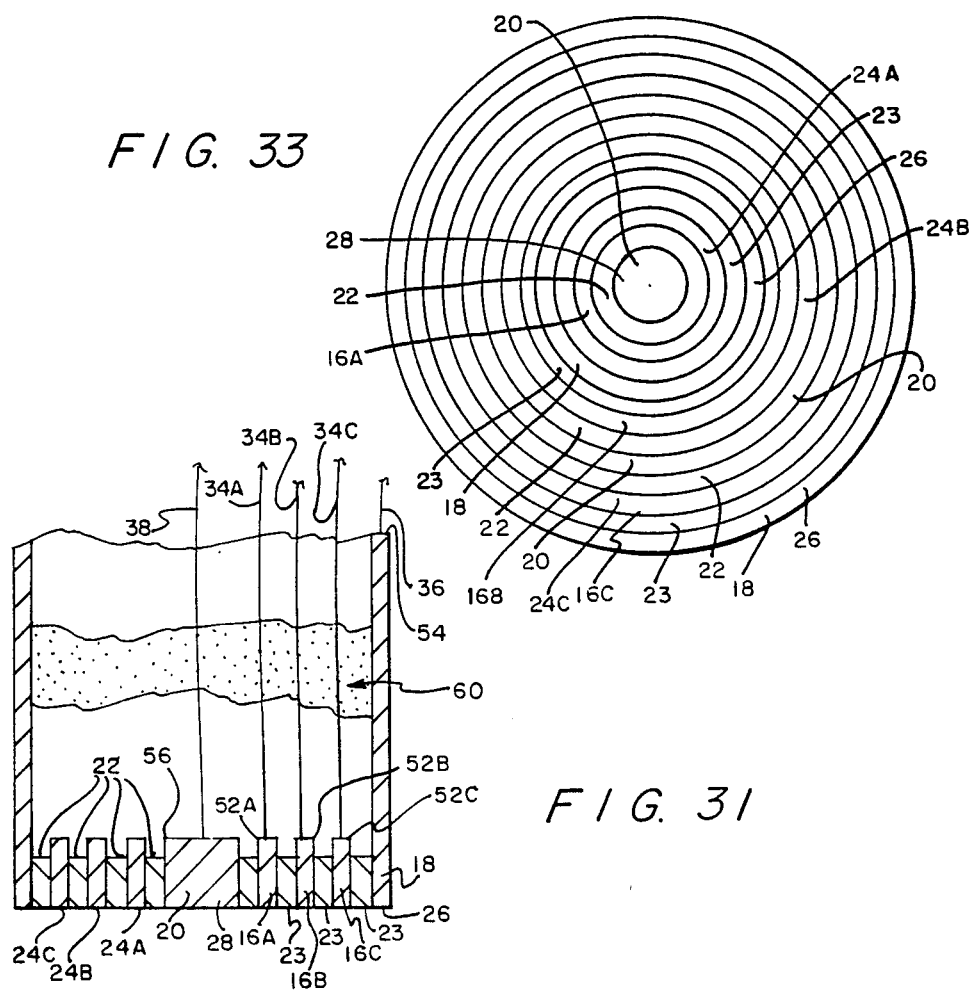
FIG. 33
FIG. 31

CORROSION CURRENT/POTENTIAL CURVES IN CRUDE B, 40% BRINE 760 PSIG $CO_2$, 180°F FOR FIGS. 6,7 & 11 PROBE BEFORE (X) & AFTER (●) TREATMENT WITH HOT KOH.

CORROSION CURRENT/TIME PROFILES FOR VARYING % BRINE (4% NaCl) IN CRUDE C, 760 PSIG $CO_2$, 185°F.

CORROSION CURRENT/TIME PROFILES FOR VARYING % BRINE (4% NaCl) FOR PARALLEL ELECTRODE PROBE IN CRUDE C, 760 PSIG $CO_2$, 185° F.

CORROSION CURRENT VS. TIME FOR N80 STEEL IN CRUDE B, 40% BRINE, 760 PSIG CO$_2$, 185°F

CORROSION RATE (WEIGHT LOSS) VS. TIME FOR N80 STEEL IN CRUDE B, 40% BRINE, 760 PSIG CO$_2$, 185°F

CORROSION CURRENT POTENTIAL CURVES IN CRUDE B, 40% BRINE 760 PSIG $CO_2$, 180°F FOR FIGS 24 & 25 PROBE BEFORE (X) & AFTER (●) TREATMENT WITH HOT KOH.

CORROSION RATE / TIME PROFILES FOR N80 STEEL IN CRUDE A, 40% BRINE, 760 PSIG $CO_2$, 185°F FOR FIGS. 24 & 25 PROBE (X), FIGS. 6 & 7 PROBE (●), AND COUPON WEIGHT LOSS (▲).

PROBE METER AND CORROSOMETER READINGS AND % WATER CUT DETERMINATIONS IN 6-INCH DIAMETER WELL FLOWING.

CORROSION CURRENT / % $H_2O$ PROFILES FOR TETROHYDROFURAN (THF) WITH ADDED $H_2O$ AT VARYING APPLIED POTENTIAL

EFFECT OF ADDING DESSICANT ON THE CORROSION CURRENT/TIME PROFILE FOR PURE TETROHYDROFURAN WITH 0.01% ADDED $H_2O$.

CORROSION CURRENT / POTENTIAL CURVE FOR SAE 30 QUAKER STATE MOTOR OIL WITH 468 PPM $H_2O$

CORROSION CURRENT/WATER CONCENTRATION CURVE FOR SAE 30 QUAKER STATE MOTOR OIL WITH 200 MILLIVOLTS APPLIED VOLTAGE.

CORROSION CURRENT PATTERN WITH RAPIDLY CHANGING APPLIED POTENTIAL

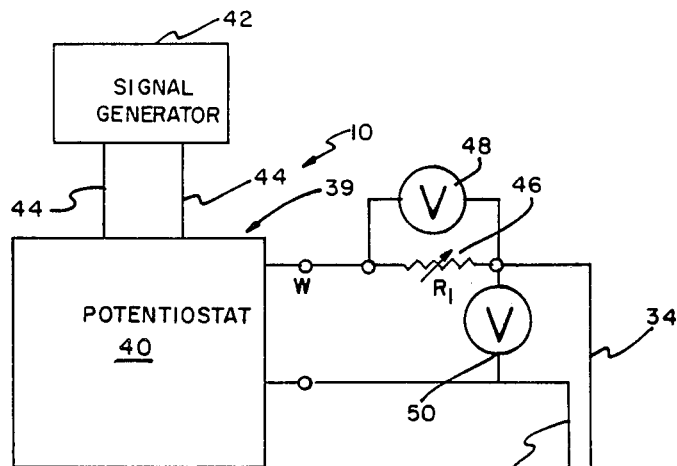
FIG. 48
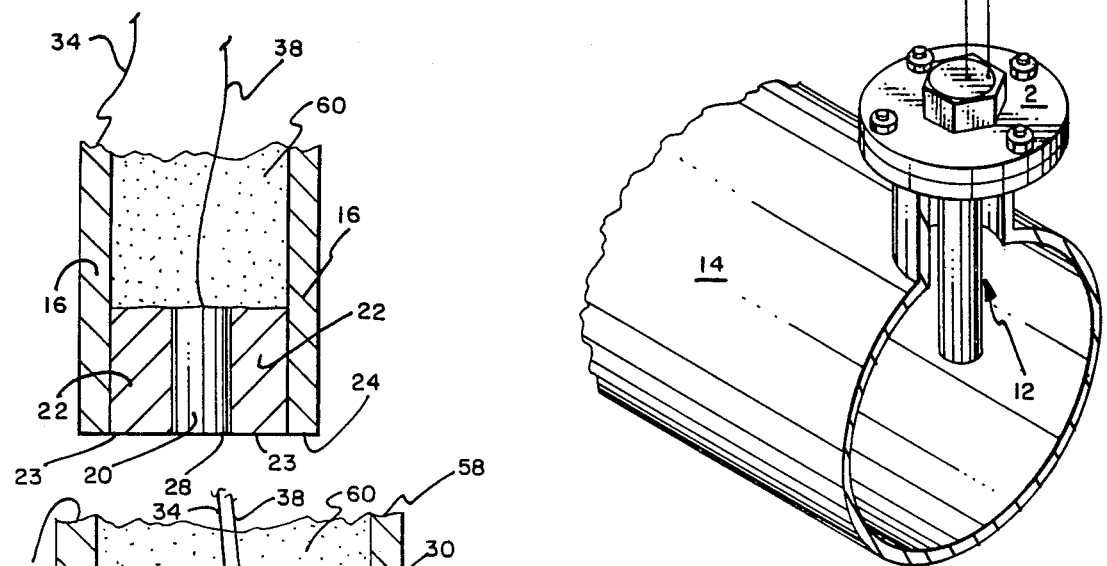
FIG. 49
FIG. 50
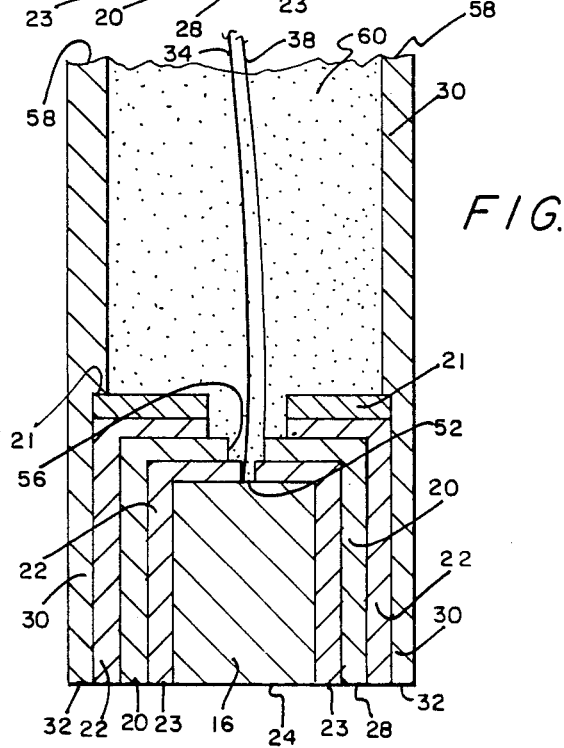
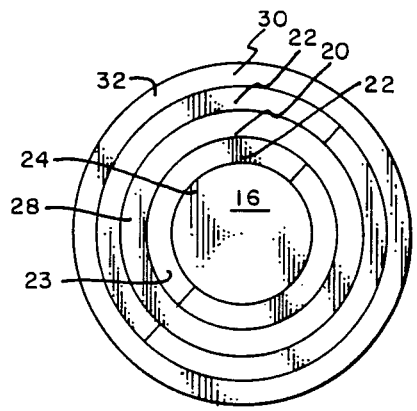
FIG. 51

CORROSION PROBE AND METHOD FOR MEASURING CORROSION RATES

This is a continuation application of co-pending patent application having Ser. No. 903,036 and filed Aug. 29, 1986 now U.S. Pat. No. 4,752,360, issued June 21, 1988. Copending patent application with Ser. No. 903,036, filed Aug. 29, 1986 was a continuation-in-part application of my co-pending patent application having Ser. No. 740,497 and filed on June 3, 1985, now abandoned. Co-pending patent application with Ser. No. 740,497, filed on June 3, 1985 was a continuation-in-part application of my co-pending patent application having Ser. No. 646,236 and filed on Aug. 31, 1984, now abandoned.

BACKGROUND OF THE INVENTION

1. Field of the invention

This invention relates to an improvement in measuring corrosion rates. More specifically, this invention provides an improved corrosion probe and a method for rapidly measuring corrosion rates of metals, or the like, in a corrosive liquid environment.

2. Description of the Prior Art

When crude oil is produced, it often comprises corrosive components, such as brines containing dissolved $CO_2$ or $H_2S$. Carbon dioxide, naturally occurring or used as a "gas lift" to assist the production of crude oil, is one corrosive component that further increases the corrosivity of the crude oil. Corrosion destroys production tubing which can result in production losses and costly workover of the well.

Not all corrosive brine liquid environments, such as brine/crude oil/gas mixtures, induce the same rate of corrosion on metals. Some corrosive liquid environments corrode metals at a more rapid rate than others. It is desirable and cost effective to treat with a corrosive inhibitor those corrosive liquid environments, such as some brine/crude oil/gas mixtures, which are substantially corrosive while not treating or closely monitoring the treatment of those corrosive liquid environments which are negligibly corrosive. This is possible only if the combination of pressure, temperature, gas and fluid compositions which will be corrosive can be predicted along with those metal alloys and inhibitor systems which will minimize corrosion. Reliable predictions and concomitant material selections are possible only if accelerated, accurate and unequivocal corrosion rate measurements can first be made under controlled environmental and chemical conditions, which are identical to, or closely approximating those experienced in the field. It is therefore preferable, if not necessary, that corrosion rate measurements be made directly in corrosive liquid environments in order to obtain reliable predictions along with those metal alloys and inhibitors which will prevent corrosion or keep it at a minimum.

Electrochemical polarization measurements are widely used to measure the corrosion rates of metals in brines. The technique is rapid and accurate and, therefore, the preferred method for monitoring corrosivity. However, the electrical resistance of oil/brine mixtures can be many orders of magnitude greater than the brine itself. This results in an IR voltage correction (current x inter-electrode resistance) many times greater than the voltage involved in the corrosion process (e.g., 10 volts vs. 0.01 volts). This results in considerable scatter and error in the data, limiting the use of electrochemical polarization methods for measuring the corrosivity of oil/brine mixtures.

U.S. Pat. No. 3,331,021 to Marsh, et al. relates to a method and apparatus for measuring instantaneous corrosion rates of specimens exposed to corrosive electrolytes. U.S. Pat. No. 3,337,440 to Nestor teaches a novel and improved apparatus which may be employed to investigate the corrosive characteristics of metallic substances and/or the effectiveness of corrosion inhibitors in water insoluble non-conducting environments. U.S. Pat. No. 3,361,660 to Chittum, et al. provides an apparatus for measuring the electrochemical potential of the inner surface of a tank containing brine. The apparatus comprises a tubular member that can be inserted through an access opening, such as a gate valve that may be installed for such purpose, or one that is already available, in order to make electrolytic contact with the brine solution in the tank. U.S. Pat. No. 3,436,320 to Marsh discloses a method and apparatus for determining the redox current and the corrosion current in a redox solution. The electrodes include an electrode with a corrodible metal to be tested, and a reference electrode. The same direct current voltage is applied to an inert electrode and the reference electrode in measuring the currents. U.S. Pat. No. 3,406,101 to Kilpatrick is concerned with correlating the polarization characteristics of metals with the corrosion rate of the metals, and with the design of a compact and simple apparatus adapted to permit an easy and rapid determination of the rates at which the metals are corroding in electrolytic solutions by means of polarization measurements. U.S. Pat. No. 3,486,996 to Annand discloses a corrosion test probe assembly for determining the corrosion rate of metallic constructional material exposed to a corrodant electrolyte by means of polarization measurements. U.S. Pat. No. 3,518,530 to Wilson teaches the procurement and use of polarization characteristics of metals such that when placed in underground formations, either directly or in cooperation with other electrical properties of the formations, determine the nature of the formation and/or the fluid contents of those formations. U.S. Pat. No. 3,607,673 to Seyl discloses a system for correcting for the IR drop between electrodes when corrosion rate of the electrodes is measured by applying a small dc voltage across the electrodes. U.S. Pat. No. 4,040,931 to Wilson relates to the instruments and the electrochemical techniques used in measuring and testing corrosion processes.

None of the foregoing prior art teaches or suggests the particular corrosion probe, the apparatus, or the processes of this invention for measuring the corrosion rates of metals in a corrosive liquid environment.

SUMMARY OF THE INVENTION

It is therefore an object of this invention to provide a corrosion probe for measuring rapidly and accurately the corrosivity of a corrosive liquid environment on metals.

It is another object of this invention to provide a process for measuring the corrosion rates of metals, or the like, in a corrosive liquid environment which is more rapid than with conventional weight-loss methods.

It is yet another object of this invention to provide a corrosion probe which may be inserted directly into a corrosive liquid environment in order to obtain in situ electrochemical measurement of the corrosivity of the corrosive liquid environment on metals.

Still other objects will be apparent to those skilled in the art from the following description of this invention.

The foregoing objects are achieved according to the practice of the invention. Broadly, this invention comprises a corrosion probe means utilized in measuring the corrosion rates of metals, or the like, in a corrosive liquid environment. The corrosion probe has at least one first electrode means, at least one second electrode means, and at least one third electrode means. A dielectric means is positioned between the first and the second electrode means and between the second and the third electrode means. The dielectric means has an ionically conductive surface.

This invention also comprises an apparatus for measuring the corrosion rates of metals, or the like, in a corrosive liquid environment comprising in combination at least one first electrode means having at least one first depending conductor means attached thereto. At least one second depending conductor means is bound to at least one second electrode means, and at least one third depending conductor means is connected to at least one third electrode means. A dielectric means is positioned between each of the first and second electrode means and between each of the second and the third electrode means. The dielectric means has an ionically conductive surface. At least one means for transmitting current is electrically engaged to the at least one first, to the at least one second, and to the at least one third depending conductor means to transmit current through each of the first electrode means, over the ionically conductive dielectric surface between each of the first electrode means and each of the third electrode means, and through each of the third electrode means back to the means for transmitting current.

In another embodiment of the invention, the means for transmitting current is replaced with at least one means for applying differences in potential which applies differences in potential between of the first electrode means of and the second electrode means. The apparatus also comprises at least one means for measuring the difference in potential between each of the first electrode means and each of the second electrode means and/or at least one means for measuring and determining the current being conducted through the first electrode means and the third electrode means.

This invention further comprises a process for measuring the corrosion rates of metals, or the like, in a corrosive liquid environment. The process includes attaching electrically the corrosion probe means to a means for transmitting current or a means for applying differences in potential. The ohmic resistance between the first and the second electrode means is known. The electromotive force between the second electrode means and an area in the surrounding corrosive liquid environment fluid in general microscopic proximity thereto is also known or, if not known, is constant during the period of the measurement of the corrosion rate because the only determination that is necessary is the additional emf (overvoltage) to pass current between the first electrode and a third electrode. While the corrosion probe means is in the corrosive liquid environment, either a predetermined known current is transmitted through the first electrode means and the third electrode means, and through the third electrode means back to the means for transmitting current; or a predetermined known difference in potential is applied between the first electrode means and the second electrode means. If a predetermined known current is signaled, simultaneously with this signaling, the electromotive force between the first and the second electrode means is measured. If a predetermined known difference in potential is signaled, simultaneously with this signaling, the current is measured that is being conducted through the first electrode means, over the ionically conductive dielectric surface between the first electrode means and the third electrode means, and through the third electrode means back to the means for applying differences in potential. From the predetermined known current, or from the measured current, and the predetermined known ohmic resistance between the first and second electrode means, an electromotive force between an area in the corrosive liquid environment in general microscopic proximity to the first electrode means and an area in the corrosive liquid environment in general microscopic proximity to the second electrode means is calculated. The electromotive force between the first electrode means and an area in the corrosive liquid environment in general microscopic proximity to the first electrode means is determined by subtracting from the measured electromotive force, or the predetermined known difference in potential between the second electrode means and an area in a surrounding fluid means in general microscopic proximity thereto, the predetermined known electromotive force and the electromotive force calculated from the predetermined known current or from the measured current, and the predetermined known ohmic resistance between the first and the second electrode means. The corrosion current on the first electrode means is computed from the predetermined known current or the measured current, and from the determined electromotive force between the first electrode means and an area in the corrosive liquid environment in general microscopic proximity to the first electrode means. The corrosion current may be converted into a corrosion rate.

In another embodiment of the corrosion probe, the corrosion probe has a first electrode means, a second electrode means, and a third electrode .means. A dielectric means is positioned between the first and the second electrode means and between the second and the third electrode means. The dielectric means between the first and the second electrode has an ionically conductive surface. In another embodiment of this embodiment of the corrosion probe, the corrosion probe has a first electrode and a second electrode with a dielectric means therebetween that has an ionic conductive surface.

This invention also comprises another embodiment of an apparatus for measuring the corrosion rates of metals, or the like, in a corrosive liquid environment comprising in combination a first electrode means having a first depending conductor means attached thereto. A second depending conductor means is bound to a second electrode means, and a third, depending conductor means is connected to a third electrode means. A dielectric means is positioned between the first and second electrode means and between the second and the third electrode means. The dielectric means between the first and the second electrode has an ionically conductive surface. A potentiostat means is electrically engaged to the first, to the second, and to the third depending conductor means to transmit current through the first electrode means, through the corrosive liquid environment, and through the third electrode means back to the potentiostat means. Another embodiment of this embodiment of the apparatus for measuring the corrosion rates of metals, or the like, in a corrosive liquid environment comprises in combination a first electrode means having a first depending conductor means attached thereto. A second depending conductor means is bound to a second electrode means. A dielectric means is positioned between the first and the second electrode means and has an ionically conductive surface. A current conductor means is provided with a third conductor means. A potentiostat means is electrically engaged to the first, the second, and the third depending conductor to transmit current through the first electrode, through the corrosive liquid environment, and through the current conductor means back to the potentiostat means.

In yet another embodiment of the invention, a potentiostat means applies differences in potential between the first electrode means and the second electrode means. The apparatus also comprises at least one means for measuring the difference in potential between the first electrode means and the second electrode means and/or at least one means for measuring and determining the current being conducted through the first electrode means and the third electrode means. At least one means is included for signaling to the potentiostat means the difference in potential and/or the current which is to be respectively applied and transmitted by same.

This invention further comprises another embodiment of the process for measuring the corrosion rates of metals, or the like, in a corrosive liquid environment. The process includes attaching electrically the corrosion probe means to a potentiostat means. The electromotive force between the second electrode means and an area in a surrounding corrosive liquid environment in general microscopic proximity thereto is known. The corrosion probe means is inserted into the corrosive liquid environment where the electromotive force is known between the second electrode means and the area in the corrosive liquid environment in general microscopic proximity thereto. Either a predetermined known current is signaled to the potentiostat means which transmits this current through the first electrode means, the corrosive liquid environment, and through the third electrode means, or the current conductor means, back to the potentiostat means; or a predetermined known difference in potential is signaled to the potentiostat means which applies this difference in potential between through the first electrode mean and the second electrode means. If a predetermined known current is signaled, simultaneously with this signaling, the electromotive force between the first and the second electrode means is measured. If a predetermined known difference in potential is signaled, simultaneously with this signaling, the current is measured that is being conducted through the first electrode means, through the corrosive liquid environment, and through the third electrode means, or the current conductor means, back to the potentiostat means. The electromotive force between the first electrode means and an area in the corrosive liquid environment in general microscopic proximity to the first electrode means is determined by subtracting from the measured electromotive force, or from the signaled predetermined known difference in potential, the predetermined known electromotive force between the second electrode means and an area in the surrounding corrosive liquid environment in general microscopic proximity thereto. The corrosion current on the first electrode means is computed from the predetermined known current or the measured current, and from the determined electromotive force between the first electrode means and an area in the corrosive liquid environment in general microscopic proximity to the first electrode means. The corrosion current may be converted into a corrosion rate.

Thus, by the practice of this invention, there is provided a corrosion probe means, and an apparatus and a process for measuring the corrosion rates of metals, or the like, in a corrosive liquid environment which overcomes such problems as the ohmic resistance of hydrocarbon/brine mixtures being much greater than brine itself and resulting in a voltage correction much larger than the voltage associated with the process of corrosion.

BRIEF DESCRIPTION OF THE DRAWINGS

FIG. 1 is a perspective view of the corrosion probe inserted into and attached to a pipe transporting a corrosive liquid, along with the circuitry diagram for the apparatus that measures the corrosion rate of metals in a corrosive liquid environment;

FIG. 2 is an exploded perspective view of one embodiment of the corrosion probe that utilizes a plurality of rectangular shaped plates for the electrodes;

FIG. 3 is a bottom plan view of the embodiment of the corrosion probe of FIG. 2 including a cylindrical sheath means surrounding the corrosion probe and a retaining material means for retaining the corrosion probe within the sheath means;

FIG. 4 is an exploded partial vertical sectional schematic view of the dielectric including the dielectric surface aligned with a plurality of ionically conductive negative charged ions chemically bound to the surface of the dielectric;

FIG. 5 is an exploded partial vertical sectional schematic view of the dielectric including the dielectric surface having a plurality of alternating negative and positive charged ions imbedded therein;

FIG. 16 is a a partial vertical sectional view of another embodiment of the corrosion probe having the reference and the working electrodes with an ionic surface therebetween with negative charged ions imbedded therein and a cylindrical sheath means surrounding the two electrodes shown schematically;

FIG. 17 is a partial vertical sectional view of the embodiment of the corrosion probe of FIG. 16, but without the sheath means and with alternating negative and positive charged ions imbedded therein shown schematically;

FIG. 18 is a horizontal sectional view taken in direction of the arrows and along the plane of line 18—18 in FIG. 12;

FIG. 19 is a horizontal sectional view taken in direction of the arrows and along the plane of line 19—19 in FIG. 16;

FIG. 20 is another embodiment of the corrosion probe having a cylindrical sheath means surrounding a reference and a working electrode;

FIG. 21 is a bottom plan view of the embodiment of the corrosion probe of FIG. 20;

FIG. 31 is a partial vertical sectional view of the corrosion probe with three working electrodes of diverse metals between a reference electrode and a counter electrode;

FIG. 32 is another embodiment of the corrosion probe of FIG. 28 and having three working electrodes of diverse metals;

FIG. 33 is a bottom plan view of the embodiment of the corrosion probe of FIG. 32;

FIG. 48 is a perspective view of the corrosion probe having a working electrode and a counter electrode and inserted into and attached to a pipe transporting a corrosive liquid, along with the circuitry diagram for the apparatus that measures the corrosion rate of metals in a corrosive liquid environment;

FIG. 49 is a partial vertical sectional view of another embodiment of the improved corrosion probe having a cylindrical working electrode surrounding a counter electrode;

FIG. 50 is yet another embodiment of the corrosion probe having a cylindrical sheath means surrounding a centrally positioned working electrode and a counter electrode that is disposed between the working electrode and the sheath means; and FIG. 51 is a bottom plan view of the embodiment of the corrosion probe of FIG. 50.

DETAILED DESCRIPTION OF THE INVENTION

Figure 6:
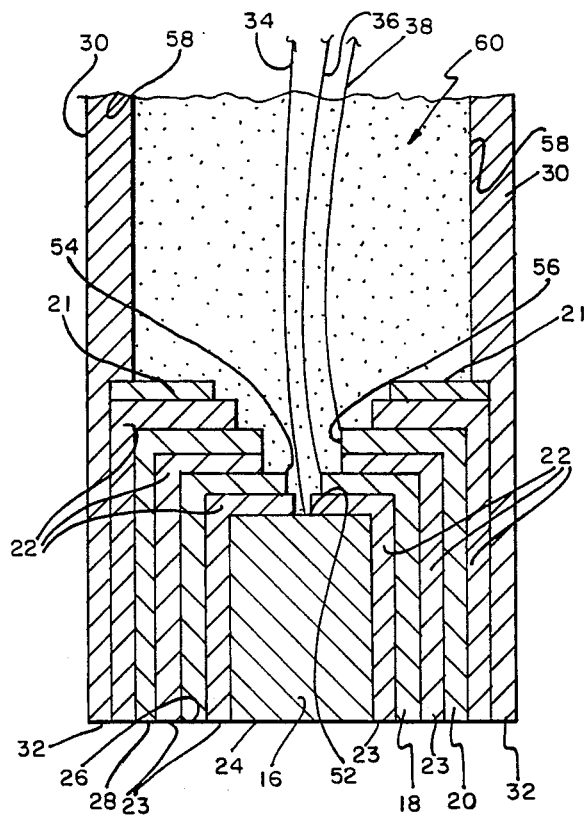
FIG. 6 is a partial vertical sectional view of one embodiment of the corrosion probe having a cylindrical sheath means surrounding three cylindrical electrodes.

Referring in detail now to the drawings, wherein similar parts of the invention are represented by like reference numerals, there is seen in FIG. 1 an apparatus, generally illustrated as 10, for measuring the corrosion rate of metals, or the like, in a corrosive liquid environment, such as a hydrocarbon/brine mixture. The apparatus 10 comprises a corrosion probe, generally illustrated as 12, which is inserted into the corrosive liquid environment contained within a pipe 14, an autoclave 15 (see FIG. 12), or the like.

In one embodiment of the corrosion probe 12 (see FIGS. 2-11), the corrosion probe 12 includes at least one working electrode 16, at least one reference electrode 18, and at least one counter electrode 20. An insulation means or dielectric means 22 is positioned between each of the working electrodes 16 and the reference electrodes 18 and between each of the reference electrodes 18 and the counter electrodes 20. The electrodes 16, 18 and 20 are generally embedded in the dielectric 22. In this embodiment of the corrosion probe 12, the dielectric 22, more particularly the facing of the dielectric 22, between all electrodes has an ionically conductive and electronically insulating surface 23; and the reference electrode 18 is positioned between the working electrode 16 and the counter electrode 20. The ionically conductive surface 23 in the present invention generally functions as a two dimensional Luggin Capillary.

The working electrode 16, the reference electrode 18, and the counter electrode 20 terminate into a working electrode end 24, a reference electrode end 26, and a counter electrode end 28, respectively, which are preferably substantially in a coplanar relationship among and with respect to each other. The electrodes 16, 18 and 20 have generally planar terminal ends 24, 26 and 28, respectively, which are aligned in a plane substantially transverse to the longitudinal axis of said electrodes 16, 18, and 20. The ionically conductive surface 23 of the dielectric 22 is also preferably in a coplanar relationship among and with respect to the working electrode end 24, the reference electrode end 26, and the counter electrode end 28. The dielectric 22, more particularly the ionically conductive surface 23, is substantially flush (or a very small, minuscule finite distance from being flush) with the planar terminal ends 24, 26 and 28 of the electrodes 16, 18 and 20, respectively, such as to have generally a common terminal planar surface. If the ionically conductive surface 23 of the dielectric 22 is not substantially coplanar or substantially flush with the terminal ends 24, 26 and 28 of the electrodes 16, 18 and 20, respectively, and is either recessed or protruded with respect thereto, then the corrosion probe 12 of this invention may be utilized to study crevice corrosion, a phenomenon well known to those skilled in the art. The corrosion probe 12 may additionally comprise a sheath 30 (see FIGS. 6, 7 and 11) that terminates into a sheath end 32. The dielectric 22, preferably without the ionically conductive surface 23, may also be positioned between the counter electrode 20 and the sheath 30. The sheath end 32 and the dielectric 22 between the counter electrode 20 and the sheath 30 are preferably also coplanar with respect to the ionically conductive surface 23 and with respect to the working electrode end 24, the reference electrode end 26, and the counter electrode end 28.

Depending conductors 34, 36 and 38 as illustrated in FIG. 1 attach electrically to the working electrode 16, the reference electrode 18, and the counter electrode 20, respectively, and interconnect electrically the corrosion probe 12 with any means or a device, generally illustrated as 39, which is capable of delivering, applying, or transmitting to the probe 12, a constant voltage or a constant current. Preferably, device 39 comprises a potentiostat 40, which is conventional in design and a signal generator 42, which is also conventional in design. Signal generator 42 electrically engages the potentiostat 40 via conductors 44-44 for instructing or signaling a predetermined known current or amperage, or a predetermined known difference in potential or voltage, to the potentiostat 40 which transmits the same to the corrosion probe 12 through one or more of the conductors 34, 36 and 38, as will be explained hereafter. It should be understood that whenever "amperage" and "voltage" are referred to herein, "amperage" means current and "voltage" means difference in potential.

Variable resistor 46 can be connected in series within conductor 34. Voltmeter 48 is electrically attached across resistor 46, and in combination with the variable resistor 46, is an ammeter to measure and determine the current through conductor 34. For example, if variable resistor 46 is set at 1 megohm, then under Ohm's Law, the readings of the voltmeter 48 in volts are identically current in microamps. Voltmeter 50 interconnects conductors 34 and 36 to measure the difference in potential between these two conductors.

Figure 8:
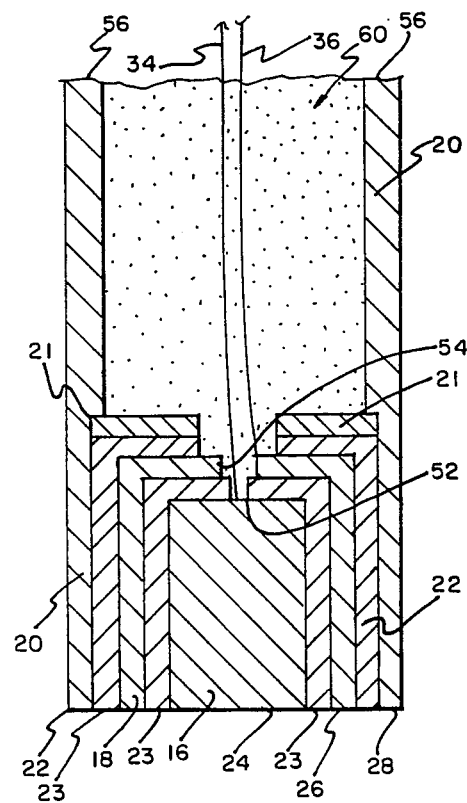
FIG. 8 is a partial vertical sectional view of another embodiment of the corrosion probe having three cylindrical electrodes with no cylindrical sheath means.
Figure 7:
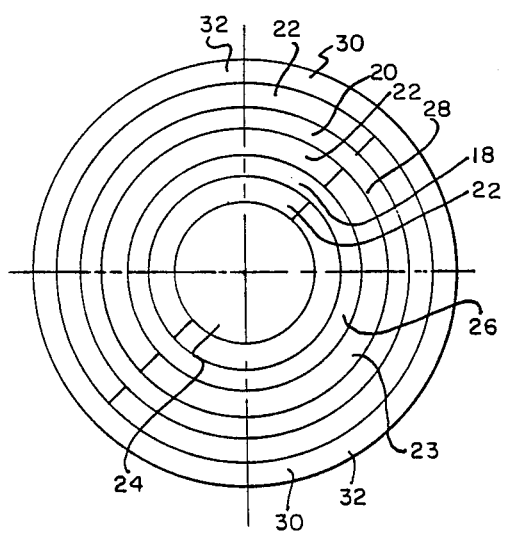
FIG. 7 is a bottom plan view of the embodiment of the corrosion probe of FIG. 6.
Figure 9:
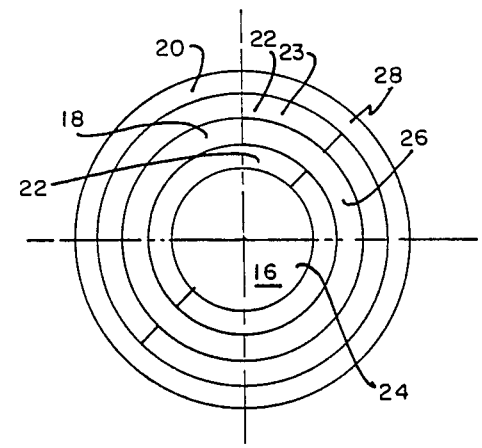
FIG. 9 is a bottom plan view of the embodiment of the corrosion probe of FIG. 8.
Figure 10:
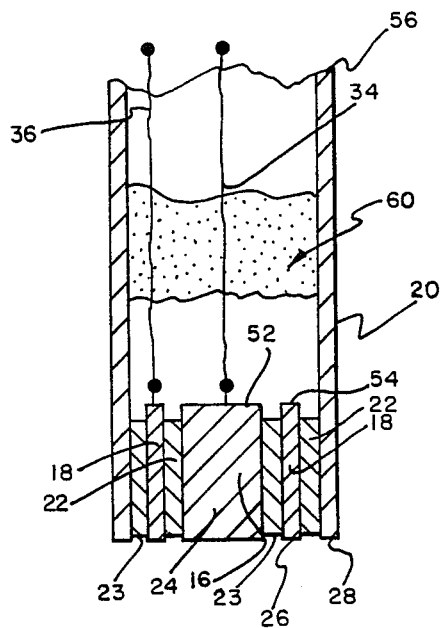
FIG. 10 is another embodiment of the corrosion probe having three cylindrical electrodes with no cylindrical sheath means.
Figure 11:
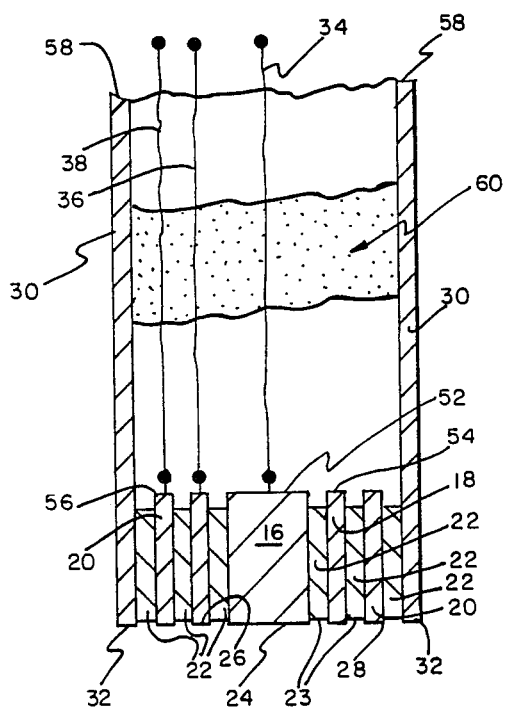
FIG. 11 is yet another embodiment of the corrosion probe having a cylindrical sheath means surrounding three cylindrical electrodes.

In the embodiment of the corrosion probe 12 depicted in FIGS. 6, 7, 8, 9, 10, and 11, working electrode 16 is shaped as a cylinder and reference electrode 18 is essentially a cylindrical ring circumferentially surrounding the working electrode 16 and concentrically positioned with respect thereto. Counter electrode 20 is also essentially a cylindrical ring that circumferentially surrounds the reference electrode 18 and is also concentrically positioned with respect to the working electrode 16 and with respect to the reference electrode 18. In the embodiment of FIGS. 8, 9 and 10, counter electrode 20, in addition to being an electrode, defines a housing means with an open end means, or a sleeve, or the sides of the corrosion probe 12, and has a much greater length than the reference electrode 18 and the working electrode 16. In the embodiment of FIGS. 6, 7 and 11, the counter electrode 20 is approximately the same length or a little longer than reference electrode 18 and working electrode 16, and sheath 30 (which functions as a housing with an open end) has a general structure defining essentially a cylindrical sleeve circumferentially surrounding the counter electrode 20 and concentrically postioned with respect to the working electrode 16, the reference electrode 18, and the counter electrode 20. A washer 21 may be positioned on top of dielectric 22 as depicted in FIGS. 6 and 8.

The working electrode end 24, the reference electrode end 26, and the counter electrode end 28 are respectively structurally opposed to a working electrode opposed end 52, a reference electrode opposed end 54, and to a counter electrode opposed end 56.

The sheath end 32 is structurally opposed to a sheath opposed end 58. In FIG. 6 the reference and counter electrodes 18 and 20 are structurally disfigured such that opposed ends 54 and 56 are essentially normal with respect to the main structure of the reference and counter electrodes 18 and 20. Depending conductors 34, 36 and 38 respectively engage electrically the opposed ends 52, 54 and 56.

In the embodiment for the corrosion probe 12 in FIGS. 8, 9 and 10, opposed end 56 of counter electrode 20 is structurally disposed at a greater distance from the counter electrode end 28 than the opposed ends 54 and 52 are structurally disposed from the reference electrode end 26 and the working electrode end 24, respectively, such as to create a void space within the inner cylindrical wall of the counter electrode 20. In this embodiment, the void space may be defined as the available space from the opposed ends 52 and 54 of the working electrode 16 and the reference electrode 18, respectively, and from the dielectric 22 positioned between the working electrode 16 and the reference electrode 18 and between the reference electrode 18 and counter electrode 20, up to a space extremity that generally registers with the opposed end 56 of the counter electrode 20 (see FIG. 10).

In the preferred embodiment for the corrosion probe 12 in FIGS. 6, 7 and 11, sheath 30 has a greater length than the working, the reference, and the counter electrodes 16, 18 and 20 such that the sheath opposed end 58 is structurally disposed at a greater distance from the sheath end 32 than the opposed ends 52, 54 and 56 are structurally disposed from the working electrode end 24, the reference electrode end 26, and the counter electrode end 28, respectively, such as to create a void space within the inner cylindrical wall of the sheath 30. In this embodiment, this void space may be defined as the available space from the opposed ends 52, 54 and 56 of the working electrode 16, the reference electrode 18, and the counter electrode 20, respectively, and from the dielectric 22 positioned between the working electrode 16 and the reference electrode 18, and between the reference electrode 18 and the counter electrode 20, and between the counter electrode 20 and the sheath 30, up to a space extremity that generally registers with the sheath opposed end 58 of the sheath 30.

A retaining material, generally illustrated as 60, is positioned generally in each of the void spaces for the embodiments of FIGS. 8, 9 and 10 and FIGS. 6, 7 and 11. Depending conductors 34 and 36 extend from the opposed ends 52 and 54, respectively, through and beyond the retaining material 60; and in the preferred embodiment of FIGS. 6, 7 and 11, depending conductor 38 also extends through and beyond the retaining material 60 from the counter electrode opposed end 56.

In the embodiment of the corrosion probe 12 depicted in FIGS. 2 and 3, working electrode 16, reference electrode 18, and counter electrode 20 are essentially rectangular plates parallelly disposed with respect to each other. While only one each of electrodes 16, 18 and 20 is needed with respect to this embodiment, it is more preferred that a plurality of the electrodes 16, 18 and 20 be utilized in the following serial fashion: working electrode 16, reference electrode 18, counter electrode 20, reference electrode 18, working electrode 16, reference electrode 18, counter electrode 20, reference electrode 18 and working electrode 16. All of these electrodes are encased in the dielectric 22 as illustrated in FIGS. 2 and 3, and the electrode ends 24, 26 and 28 of these electrodes define rectangular edges which are parallelly postured with respect to each other and substantially coplanar among and with respect to each other and the ionically conductive dielectric surface 23 therebetween. As was the case for the embodiments of the corrosion probe in FIGS. 6-11, reference electrode 18 is preferably positioned between the working electrode 16 and the counter electrode 20. The plurality of depending conductors 34, 36 and 38 respectively connect to opposed ends 52, 54 and 56 and extend through the dielectric 22 (see FIG. 2) and unite to become unique as conductors 34, 36 and 38 in the respective cases. As also was the case for the embodiments of FIGS. 6-11, conductors 34, 36 and 38 extend through and beyond the retaining material 60 which also, as represented in FIG. 3, surrounds the dielectric 22 on its sides to retain the same including the implanted electrodes 16, 18 and 20 within cylindrical sleeve wall of the sheath 30.

In the embodiment for the corrosion probe 12 in FIGS. 6-11, working electrode 16 has a diameter of less than 0.25 inches, more preferably from about 0.01 inches to about 0.20 inches. Most preferably, the diameter of working electrode 16 is about 0.175 inches. The thickness of cylindrical reference electrode 18 and cylindrical counter electrode 20, especially including their respective cylindrical reference electrode end 26 and cylindrical counter electrode end 28, is preferably less than about 0.25 inches. More preferably, the thickness of these electrodes 18 and 20, and especially including their respective electrode ends 26 and 28, is from about 0.01 to about 0.15 inches; most preferably, the thickness is about 0.05 inches. It is understood that the thickness of electrode ends 26 and 28 may be different than the thickness of the remaining respective structure of electrodes 18 and 20. The important thickness with respect to this invention is the thickness of electrode ends 26 and 28 because these are the locations of current flow and difference in potential.

In the embodiment for the corrosion probe 12 in FIGS. 2 and 3, the width of the rectangular edges of the working electrode end 24, the reference electrode end 26, and the counter electrode end 28 is less than about 0.25 inches; more preferably from about 0.01 to about 0.15 inches; and most preferably, the width of electrode ends 24, 26 and 28 is about 0.05 inches. As was the case for cylindrical electrodes 18 and 20, it is understood that the thickness or width of the rectangular edges of the electrode ends 24, 26 and 28 may be different than the thickness or width of the remaining respective structure of the generally rectangular shaped electrodes 16, 18 and 20. Again the important thickness or width is that of the rectangular edges of the electrode ends 24, 26 and 28.

Also of importance is the width of the ionic conductive surface 23 between electrode ends 24, 26 and 28, or, stated another way, the spacing between electrode ends 24 and 26 and between electrode ends 26 and 28. With respect to the embodiments of the corrosion probe 12 in FIGS. 2-11, the width of the ionic conductive surface 23 between all electrode ends 24, 26 and 28, or, stated the other way, the spacing between electrode ends 24 and 26 and between electrode ends 26 and 28, is preferably about 0.35 inches or less. It is obvious and not of substantial importance that the width of the ionic conductive surface 23 between all electrode ends 24, 26 and 28, or, in other terms, the spacing between electrode end 24 and 26 and between electrode ends 26 and 28, may be different than the width of any dielectric 22 between the remaining respective structure of electrodes 16, 18 and 20, or the spacing between the remaining respective structure of electrodes 16 and 18 and between the remaining respective structure of electrodes 18 and 20. In a more preferred embodiment of the corrosion probe 12 in FIGS. 2-11, the width of the ionic conductive surface 23 between all electrode ends, or the spacing between all electrode ends, is from about 0.01 inches to about 0.20 inches, with the most preferred being about 0.09 inches.

For the embodiment of the corrosion probe 12 in FIGS. 2-11, the dielectric 22 has an ionic conductive surface 23 between all electrodes. As will be explained below in greater detail, when this embodiment of the corrosion probe 12 is inserted into a corrosive liquid environment and a predetermined known current is transmitted by the device 39 through the sample or working electrode 16, over the ionically conductive dielectric surface 23 between the working electrode 16 and the reference electrode 18, and over the ionically conductive dielectric surface 23 between the reference electrode 18 and the counter electrode 20, and through the counter electrode 20 back to the device 39, it is assumed that the ohmic resistance across the surface of the end 26 of the reference electrode 18 is negligible compared to that across the ionic conductive surface 23 of the dielectric 22. As will be discussed hereinafter, ohmic electromotive force does in fact exist across the end 26 of the reference electrode 18 and at times may not be that negligible. This ohmic electromotive force is not measurable by conventional electronic feedback circuitry or conventional ac bridge/conductivity measurements and would therefore be included in the corrosion electromotive force measured by the embodiment of the corrosion probe 12 in FIGS. 2-11, resulting in a loss of accuracy add sensitivity in the value for corrosion current. By interchanging the positions of the working electrode 16 with the reference electrode 18 in the corrosion probe 12 and insuring that the dielectric 22 between the reference electrode 18 and the working electrode 16 has the ionically conductive surface 23, another embodiment of the corrosion probe 12 (see FIGS. 22-27) is produced which eliminates the consequences of ohmic electromotive force across the end 26 of the reference electrode 18. The dielectric 22 between the working electrode 16 and the counter electrode 20 may or may not have the ionically conductive surface 23, although it is preferred. With the embodiment of the corrosion probe 12 in FIGS. 22-27, a more accurate and more sensitive detection of corrosion current can be made.

In one embodiment of the embodiment of the corrosion probe 12 in FIGS. 22-27, the corrosion probe 12 includes the reference electrode 18, the working electrode 16, and the counter electrode 20. The insulation means or dielectric 22 is positioned between the reference electrode 18 and the working electrode 16 and between the working electrode 16 and the counter electrode 20. As was previously mentioned, the dielectric 22 between the reference electrode 18 and the working electrode 16 has the ionically conductive and electronically insulating surface 23, and the dielectric 22 between the working electrode 16 and the counter electrode 20 does not have or have to have, the ionically conductive surface 23. Similar to the embodiment of the corrosion probe 12 in FIGS. 2-11, the ionically conductive surface 23 for this embodiment of the corrosion probe 12, as well as for all other embodiments of the corrosion probe 12, functions as a two dimensional Luggin capillary. The working electrode 16 is positioned preferably between the reference electrode 18 and the counter electrode 20. The reference electrode 18, the working electrode 16, and the counter electrode 20 terminate into the reference electrode end 26, the working electrode end 24, and the counter electrode end 28, respectively. The reference electrode end 26 and the working electrode end 24 are substantially in a coplanar relationship among and with respect to each other. The counter electrode end 28 does not have to be coplanar with respect to the reference electrode end 26, but preferably counter electrode end 28 is substantially coplanar with respect to reference electrode end 26 and the working electrode end 24. The ionically conductive surface 23 of the dielectric 22 between the reference electrode end 26 and the working electrode end 24 is also preferably in a substantially coplanar relationship among and with respect to the reference electrode end 26 and the working electrode and 24. As was seen for the embodiment of the corrosion probe 12 in FIGS. 2-11, the corrosion probe 12 of FIGS. 22-27 may additionally comprise the sheath 30 that terminates into the sheath end 32. The dielectric 22, preferably without the ionically conductive surface 23, may also be positioned between the counter electrode 20 and the sheath 30. The sheath end 32 and the dielectric 22 between the counter electrode 20 and the sheath 30 are preferably, but not necessarily, also substantially coplanar with respect to the counter electrode end 28, the reference electrode end 26, the working electrode end 24, and the ionically conductive surface 23 between the reference electrode end 26 and the working electrode end 24.

Depending conductors 36, 34 and 38 attach electrically to the reference electrode 18, the working electrode 16, and the counter electrode 20, respectively, and interconnect electrically the corrosion probe 12 of FIGS. 22-27 with the device 39 which as previously indicated is capable of delivering, applying, or transmitting to the probe 12, a constant voltage or a constant current. Preferably, device 39 comprises the potentiostat 40 and the signal generator 42. Signal generator 42 functions identically with the corrosion probe 12 of FIGS. 22-27 as it does with the corrosion probe 12 of FIGS. 2-11 in that it engages electrically the potentiostat 40 via conductors 44-44 for instructing or signaling a predetermined known current, or a predetermined known difference in potential, to the potentiostat 40 which transmits as applies respectively the same to the corrosion probe 12 of FIGS. 22-27 through one or more of the conductors 34, 36, and 38, as will be explained hereafter. Also, as was previously stated for the embodiment of the corrosion probe 12 in FIGS. 2-11, the variable resistor 46 is connected in series within the conductor 34, and the meter 48 is electrically attached across resistor 46 to measure the current through conductor 34 by measuring the voltage drop across resistor 46. Voltmeter 50 interconnects conductors 34 and 36 for the embodiment of the corrosion probe 12 in FIGS. 22-27 to measure the difference in potential between these two conductors.

Figure 22:
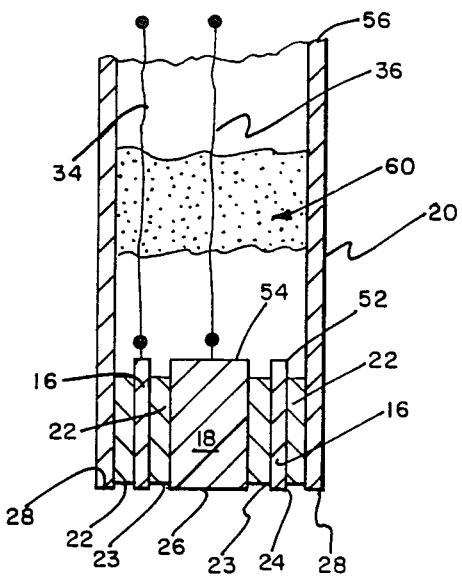
FIG. 22 is a partial vertical sectional view of another embodiment of the corrosion probe having three electrodes with no cylindrical sheath means.
Figure 23:
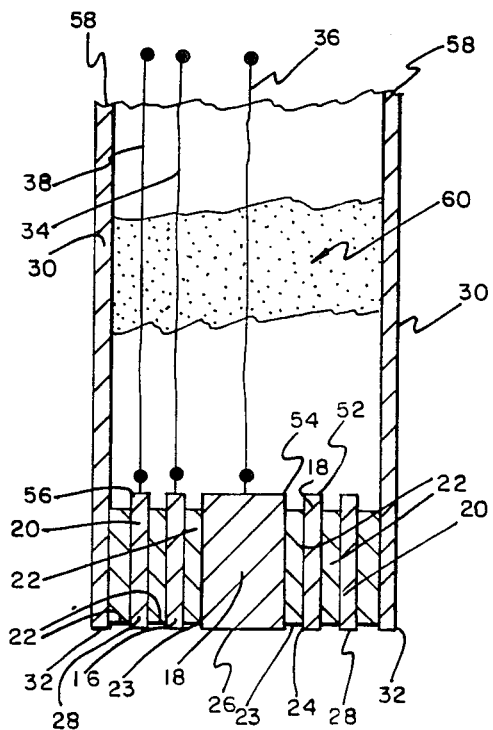
FIG. 23 is a partial vertical sectional view of yet another probe having three electrodes and a cylindrical sheath means.
Figure 24:
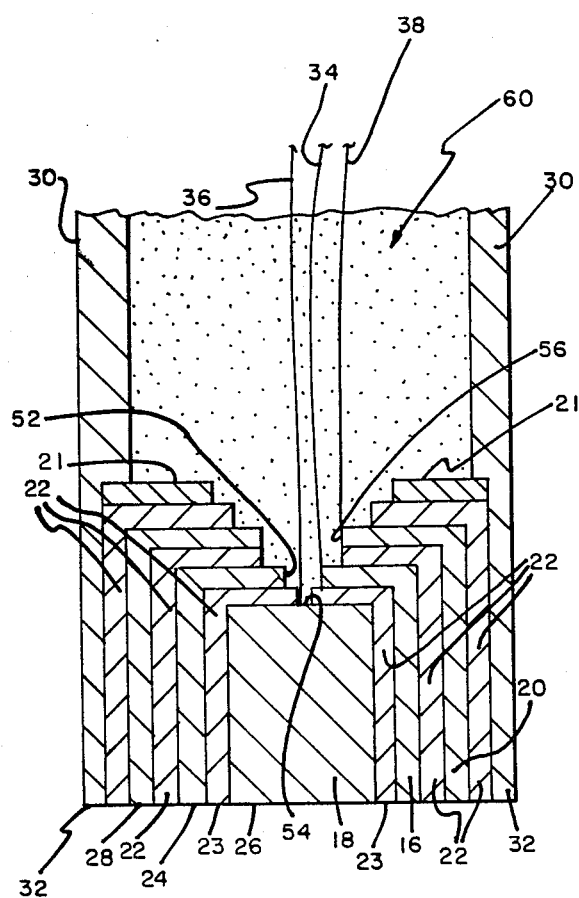
FIG. 24 is a partial vertical sectional view of another embodiment of the corrosion probe having three electrodes with a cylindrical sheath means.
Figure 26:
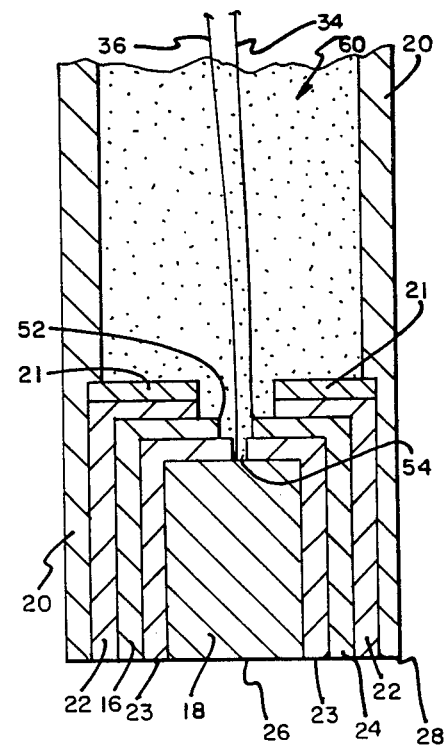
FIG. 26 is a partial vertical sectional view of still yet another embodiment of the corrosion probe having three electrodes with no cylindrical sheath means.
Figure 25:
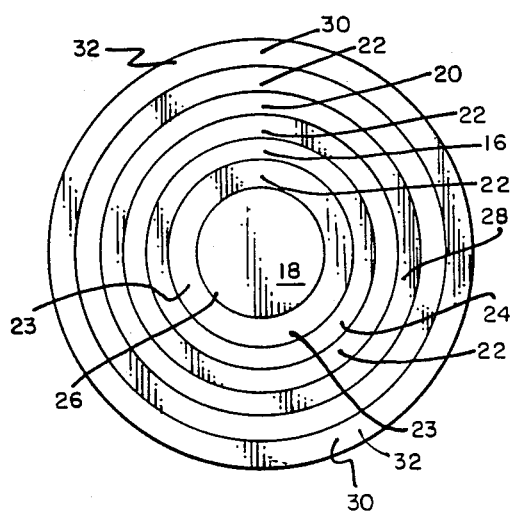
FIG. 25 is a bottom plan view of the embodiment of the corrosion probe of FIG. 24.
Figure 27:
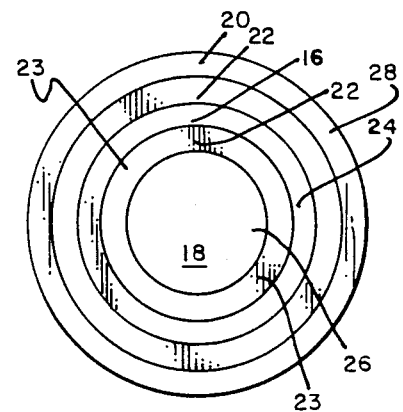
FIG. 27 is a bottom plan view of the embodiment of the corrosion probe of FIG. 26.

In the embodiment of the corrosion probe 12 depicted in FIGS. 22, 23, 24, 25, 26, and 27, reference electrode 18 is shaped as a cylinder and working electrode 16 is essentially a cylindrical ring circumferentially surrounding the reference electrode 18 and concentrically positioned with respect thereto. Counter electrode 20 is also essentially a cylindrical ring that circumferentially surrounds the working electrode 16 and is also concentrically positioned with respect to the reference electrode 18 and with respect to the working electrode 16. In the embodiment of FIGS. 22, 26 and 27, counter electrode 20, in addition to being an electrode, defines a sleeve and has a much greater length than the working electrode 16 and the reference electrode 18. In the embodiment of FIGS. 23, 24 and 25, the counter electrode 20 is approximately the same length or a little longer than working electrode 16 and reference electrode 18, and sheath 30 has a general structure defining essentially a cylindrical sleeve circumferentially surrounding the counter electrode 20 and concentrically positioned with respect to the reference electrode 18, the working electrode 16, and the counter electrode 20. The washer 21 may be positioned on top of dielectric 22 as depicted in FIGS. 24 and 26. It should be understood that for this embodiment of my corrosion probe 12 and for the purposes thereof, my corrosion probe 12 would function just as effectively if the counter electrode 20 was in the position of the reference electrode 18 and shaped and dimensioned accordingly, and if the reference electrode 18 was in the position of the counter electrode 20 and also shaped and dimensioned accordingly.

As illustrated in FIGS. 22-27, the reference electrode end 26, the working electrode end 24, and the counter electrode end 28 are respectively structurally opposed to a reference electrode opposed end 52, a working electrode opposed end 52, and to a counter electrode opposed end 56. Similarly, the sheath end 32 is structurally opposed to a sheath opposed end 58. In FIG. 24 the working and counter electrodes 16 and 20 are structurally disfigured such that opposed ends 52 and 56 are essentially normal with respect to the main structure of the working and counter electrodes 16 and 20. Depending conductors 36, 34, and 38, respectively, engage electrically the opposed ends 54, 52, and 56.

In the embodiment for the corrosion probe 12 in FIGS. 22, 26 and 27, opposed end 56 of counter electrode 20 is structurally disposed at a greater distance from the counter electrode end 28 than the opposed ends 52 and 54 are structurally disposed from the working electrode end 24 and the reference electrode end 26, respectively, such as to create a void space within the inner cylindrical wall of the counter electrode 20. In this embodiment, the void space may be defined as the available space from the opposed ends 54 and 52 of the reference electrode 18 and the positioned between the reference electrode 18 and the working electrode 16 and between the working electrode 16 and counter electrode 20, up to a space extremity that generally registers with the opposed end 56 of the counter electrode 20 (see FIGS. 22 and 26).

In the embodiment for the corrosion probe 12 in FIGS. 23, 24, and 25, the sheath 30 has a greater length than the reference, the working, and the counter electrodes 18, 16, and 20, such that the sheath opposed end 58 is structurally disposed at a greater distance from the sheath end 32 than the opposed ends 54, 52, and 56, are structurally disposed from the reference electrode end 26, the working electrode end 24, and the counter electrode end 28, respectively, such as to create a void space within the inner cylindrical wall of the sheath 30. In this embodiment, this void space may be defined as the available space from the opposed ends 54, 52, and 56, of the reference electrode 18, the working electrode 16, and the counter electrode 20, respectively, and from the dielectric 22 positioned between the reference electrode 18 and the working electrode 16, and between the working electrode 16 and the counter electrode 20, and between the counter electrode 20 and the sheath 30, up to a space extremity that generally registers with the sheath opposed end 58 of the sheath 30.

The retaining material 60 is positioned generally in each of the void spaces for the embodiments of FIGS. 22, 26 and 27 and FIGS. 23, 24 and 25. The depending conductors 36 and 34 extend from the opposed ends 54 and 52, respectively, through and beyond the retaining material 60; and in the embodiment of FIGS. 23, 24 and 25 depending conductor 38 also extends through and beyond the retaining material 60 from the counter electrode opposed end 56.

In another preferred embodiment of the invention, the corrosion probe 12 depicted in FIGS. 16-21, includes only reference electrode 18 and working electrode 16 with the dielectric 22 therebetween having the ionically conductive dielectric surface 23. In addition to the reference electrode 18, the working electrode 16, and the dielectric 22 with the ionically conductive dielectric surface 23 therebetween, corrosion probe 12 of this embodiment of the invention may include the sheath 30 that terminates into the sheath end 32 (see FIGS. 16, 19, 20 and 21). The dielectric 22 or any similar matter or material without the ionically conductive surface 23 may be positioned between the working electrode 16 and the sheath 30. The reference electrode 18 and the working electrode 16 terminate into the reference electrode end 26 and the working electrode end 24, respectively.

Figure 12:
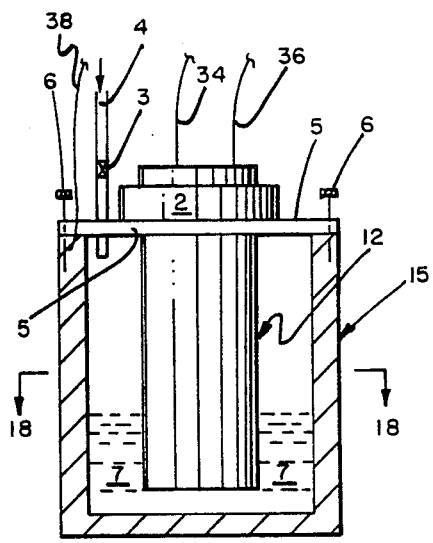
FIG. 12 is a side elevational view of an embodiment of the corrosion probe that has a working and a reference electrode with depending conductors therefrom and a third conductor depending from the side of an autoclave that has been sectionalized.
Figure 13:
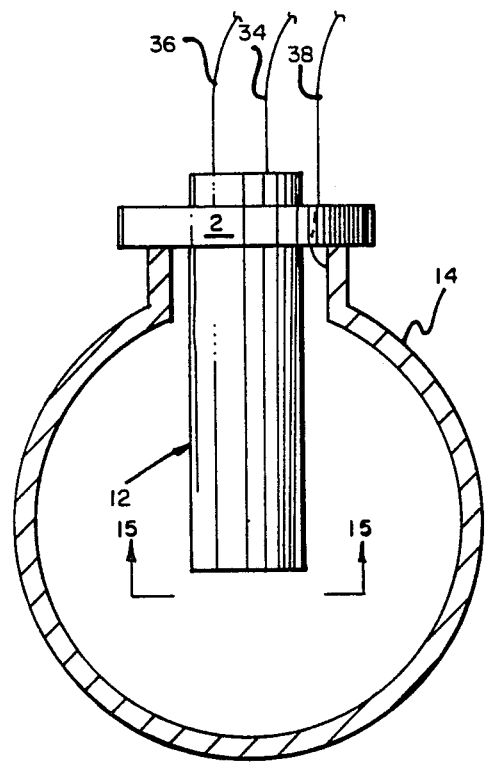
FIG. 13 is a vertical view of an embodiment of the corrosion probe that also has a working and a reference electrode with two depending conductors therefrom and a third conductor depending from a pipe that has been sectioned and which transports a corrosive liquid.
Figure 14:
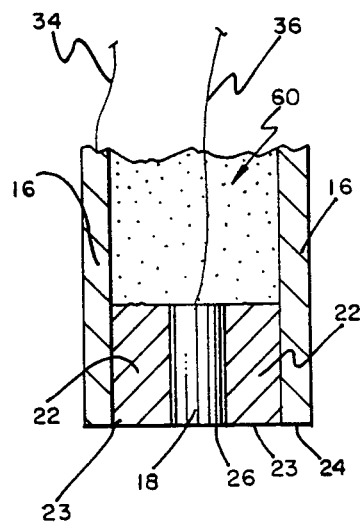
FIG. 14 is a partial vertical sectional view of one embodiment of the improved corrosion probe having a cylindrical working electrode surrounding a reference electrode.
Figure 15:
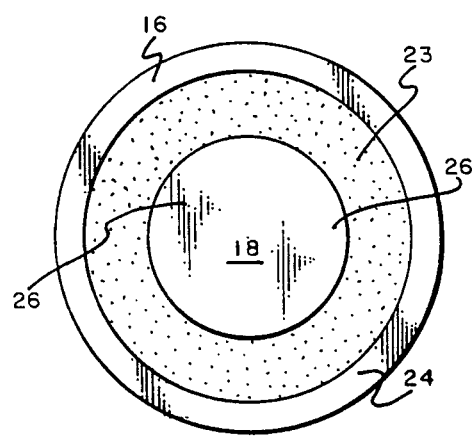
FIG. 15 is a bottom plan view of the embodiment of the corrosion probe of FIG. 14, and is taken in direction of the arrows and along the plane of line 15—15 in FIG. 13.

In this embodiment of the invention, counter electrode 20 is not needed, but is replaced with another current conductive means that is in contact with the corrosive liquid environment. Current conductive means may be any suitable means that is capable of conducting electricity emanating from the corrosive liquid environment, including but not limited to, as illustrated in FIGS. 12 and 13, the side of the autoclave 15 having a corrosive liquid 7, or the side of the pipe 14 which transports the corrosive liquid environment. Current conductive means may be manufactured or constructed of any material that is conductive of electricity such as iron, iron alloy, steel, steel alloys, or copper, copper alloys, etc.

As illustrated in FIGS. 12-21, the depending conductors 36 and 34, respectively, connect to opposed ends 54 and 52, and the depending conductor 38 attaches to the current conductive means, which in FIG. 12 is the side of the autoclave 15 and in FIG. 13 is side of the pipe 14. With respect to this embodiment of the invention, reference electrode 18 is shaped as a cylinder and working electrode 16 is essentially a cylindrical ring circumferentially surrounding the reference electrode 18 and concentrically positioned with respect thereto. Working electrode 16 in addition to being an electrode, defines a sleeve and has a much greater length than the reference electrode 18. In the preferred embodiment of FIGS. 18, 19, 20 and 21, the working electrode 16 is approximately the same length or a little longer than the reference electrode 18, and sheath 30 has a general structure defining essentially a cylindrical sleeve circumferentially surrounding the working electrode 16 and concentrically positioned with respect to the reference electrode 18 and the working electrode 16. The washer 21 may be positioned on top of dielectric 22 as depicted in FIG. 20.

The sheath 30 in FIGS. 16 and 18-21 has a greater length than the reference electrode 18 and the working electrode 16 such that the sheath opposed end 58 is structurally disposed a greater distance from the sheath end 32 than the opposed ends 54 and 52 are structurally disposed from the reference electrode end 26 and the working electrode end 24, respectively, such as to create a void space within the inner cylindrical wall of the sheath 30. In this embodiment, this void space may be defined as the available space from the opposed ends 54 and 52 of the reference electrode 18 and the working electrode 16, respectively, and from the dielectric 22 positioned between the reference electrode 18 and between the working electrode 16 and the sheath 30, up to a space extremity that generally registers with the sheath opposed end 58 of the sheath 30. The retaining material 60 is positioned generally in the void spaces within the walls of the working electrode 16 for the embodiment of FIGS. 14, 15 and 17; and within the walls of the sheath 30 for the embodiment of FIGS. 16, and 18–21. Depending conductor 36 extends from the opposed end 54 through and beyond the retaining material 60 in the embodiment of FIGS. 14, 15 and 17; and depending conductors 36 and 34 in the embodiment of FIGS. 16, 18, and 19 extend from the opposed ends 54 and 52, respectively, through and beyond the retaining material 60.

In the preferred embodiment for the corrosion probe 12 in FIGS. 22–27, reference electrode 18 has a diameter of less than 0.25 inches, more preferably from about 0.01 inches to about 0.20 inches. Most preferably, the diameter of reference electrode 18 is about 0.175 inches. The thickness of cylindrical working electrode 16 and cylindrical counter electrode 20, especially including their respective cylindrical working electrode end 24 and cylindrical counter electrode end 28, is preferably less than about 0.25 inches. More preferably, the thickness of these electrodes 16 and 20, and especially including their respective electrode ends 24 and 28, is from about 0.01 to about 0.15 inches; most preferably, the thickness is about 0.02 inches. It is understood that the thickness of electrode ends 24 and 28 may be different than the thickness of the remaining respective structure of electrodes 16 and 20. The important thickness with respect to this invention is the thickness of electrode ends 24 and 28 because these are the locations of current or amperage and difference in potential transfer.

In the preferred embodiment for the corrosion probe 12 in FIGS. 14–21, the reference electrode 18 also has a diameter of less than 0.25 inches, more preferably from about 0.01 inches to about 0.20 inches as was seen for the corrosion probe 12 embodiment in FIGS. 22–27. Most preferably, the diameter of the reference electrode 18 in FIGS. 14–21 is about 0.175 inches. The thickness of cylindrical working electrode 16, including its cylindrical working electrode end 24, is preferably less than about 0.25 inches. More preferably, the thickness of electrode 16, and especially including its respective electrode end 24, is from about 0.01 to about 0.15 inches; most preferably, the thickness is about 0.02 inches. As was the case for the corrosion probe 12 embodiment of FIGS. 14–21, it is to be understood that the thickness of the electrode end 24 may be different than the thickness of the remaining respective structure of electrode 16. For this embodiment of the corrosion probe 12, as was previously stated for the preferred embodiment for the corrosion probe 12 in FIGS. 22–27, the important thickness is the thickness of electrode end 24 because this is the location of amperage and difference in potential transfer.

The autoclave 15 in FIG. 12 has a top 5 that is bolted by bolts 6 to the top of the side wall of the autoclave 15. Conduit 4 with valve 3 is for dispensing a corrosive liquid 7 (e.g., hydrocarbon fluid plus gas) into the autoclave 15. Fitting 2 removably secures the corrosion probe 12 through the top 5 and into the inside of autoclave 15 such that the end of the corrosion probe 12 contacts the corrosive liquid 7. In FIGS. 1 and 13, fitting 2 removably attaches the corrosion probe 12 to and through the top of the pipe 14 which transports corrosive liquid(s).

As was seen for the embodiment of the corrosion probe 12 of FIGS. 2–11, also of importance is the width of the ionic conductive surface 23 between electrode ends 26 and 24 or, stated another way, the spacing between electrode ends 26 and 24. For all preferred embodiments of the corrosion probe 12, in FIGS. 12–27, the width of the ionic conductive surface 23 between the electrode ends 26 and 24, or, stated the other way, the spacing between electrode ends 26 and 24, is preferably about 0.35 inches or less. It is obvious and not of substantial importance that the width of the ionic conductive surface 23 between electrode ends 26 and 24, or, in other terms, the spacing between electrode ends 26 and 24, may be different than the width of any dielectric 22 between the remaining respective structure of electrodes 18 and 16, or the spacing between the remaining respective structure of electrodes 18 and 16. In a more preferred embodiment of the invention, the width of the ionic conductive surface 23 between the electrode ends 26 and 24 or the spacing between the electrode ends 26 and 24, is from about 0.01 inches to about 0.20 inches, with the most preferred being about 0.02 inches.

In the embodiment of the corrosion probe 12 in FIGS. 22–27, the dielectric 22 between the working electrode 16 and the counter electrode 20 does not have the ionic conductive surface 23 and the distance and/or space between the working electrode 16 and the counter electrode 20 depends on a number of variable factors, such as the amount of power that can be transmitted to the corrosion probe 12 from the device 39 (or the potentiostat 40), the conductivity of the corrosive liquid, etc. As a matter of economics, the distance and/or space between the working electrode 16 and the counter electrode 20 would be any suitable distance and/or space that would be the most cost effective with respect to the manufacturing the corrosion probe 12, such as by way of example, but not limitation, preferably no more than 0.5 inch.

In the embodiment of the corrosion probe 12 in FIGS. 12–21, the distance between the working electrode 16 and the conductive means (e.g., the side wall of the autoclave 15 or the side of the pipe 14) that replaces the counter electrode 20 also more especially depends on the previously mentioned number of variable factors, such as the amount of power that can be transmitted to the corrosion probe 12 and the conductivity of the corrosive liquid, etc. In this embodiment of the invention, there is no counter electrode 20 and economics could therefore not be one of the controlling forces as it is in the case where the probe 12 includes the counter electrode 20. For this embodiment of my invention where the corrosion probe 12 comprises reference electrode 18 and working electrode 16; or reference electrode 18, working electrode 16 and sheath 30; the distance and/or space between the working electrode 16 and the conductive means would be any suitable distance and/or space that would be reasonable and whereby current may be conducted from the working electrode 16, through the corrosive liquid, (e.g. corrosive liquid 7)

and the conductive means. Obviously, the farther the distance is between the working electrode 16 and the conductive means, the more difficult the measurements become with the corrosion probe 12; and there is a greater chance for inaccuracies in measurements with the corrosion probe 12. As a matter of convenience, I prefer that the distance and/or space between the working electrode 16 and the conductive means be preferably less than about 1 foot.

Figure 28:
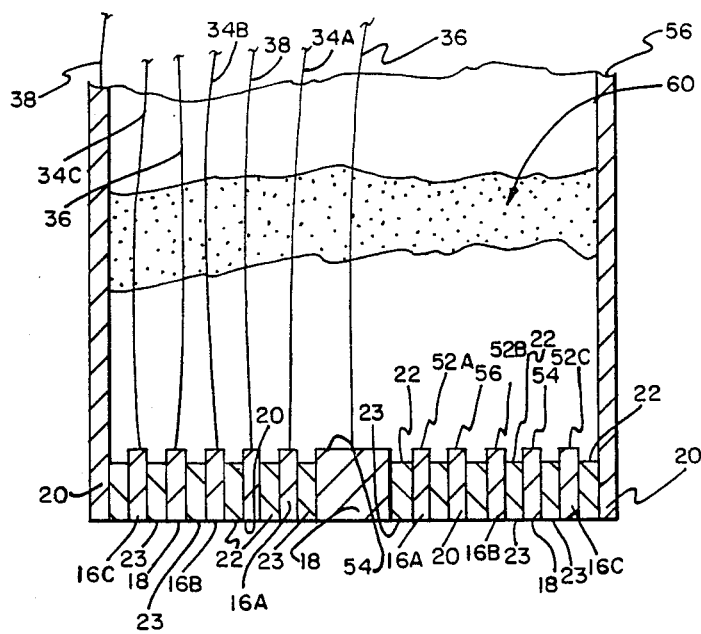
FIG. 28 is a partial vertical sectional view of the corrosion probe with three working electrodes of diverse metals.
Figure 29:
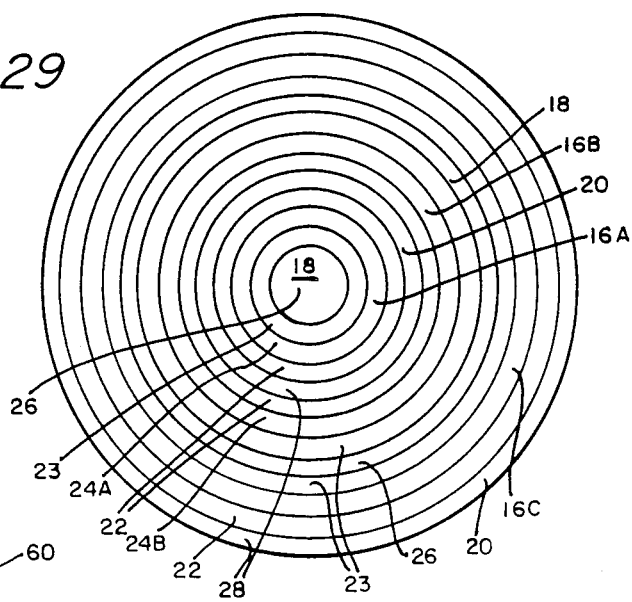
FIG. 29 is a bottom plan view of the embodiment of the corrosion probe of FIG. 28.

In yet another embodiment of the corrosion probe 12 (see FIGS. 28, 29, 30, 31, 32 and 33), the corrosion probe 12 comprises more than one sample or working electrode 16 of different or diverse metals such that the corrosion rate upon each of the diverse metals of the working electrodes 16 in the corrosive liquid environment may be measured either simultaneously or sequentially, as will be explained in greater detail hereinafter. One embodiment of this embodiment of the corrosion probe 12 is illustrated in FIGS. 28 and 29 wherein the corrosion probe 12 comprises working electrodes 16A, 16B, and 16C. Working electrodes 16A, 16B and 16C each comprise a different metal upon which the corrosion rate in the corrosive liquid environment is to be determined. The electrodes in corrosion probe 12 of FIGS. 28 and 29 are serially arranged as follows: reference electrode 18, working electrode 16A, counter electrode 20, working electrode 16B, reference electrode 18, working electrode 16C and counter electrode 20 which may also function as a sleeve to encase or surround the other electrodes. In another embodiment of this embodiment of the corrosion probe (see FIGS. 32 and 33) the corrosion probe 12 also comprises working electrodes 16A, 16B and 16C but the serial arrangement is counter electrode 20, working electrode 16A, reference electrode 18, working electrode 16B, counter electrode 20, working electrode 16C and reference electrode 18 which, like the last counter electrode 20 of FIGS. 28 and 29, may also function as a sleeve to encase or surround the other electrodes. Dielectric 22 is positioned between each of the working electrodes 16 (i.e. 16A, 16B and 16C) and the respective counter electrodes 20 and between the working electrodes 16A, 16B and 16C and the respective reference electrodes 18. As illustrated in FIGS. 28, 29, 32 and 33 ionically conductive and electronically insulating surface 23 is on the surface of the dielectric 22 between the working electrodes 16A, 16B and 16C and the respective reference electrodes 18. The surface of the dielectric 22 between the respective counter electrodes 20 and the working electrodes 16A, 16B and 16C does not have or have to have the ionically conductive surface 23. Working electrodes 16A, 16B and 16C terminate into working electrode ends 24A, 24B and 24C, respectively, which are substantially in a coplanar relationship among and with respect to any contiguous reference electrode end 26 of any of the respective reference electrodes 18. As was seen for the embodiment of the corrosion probe 12 in FIGS. 22-27, the counter electrode ends 28 of the respective counter electrodes 20 in FIGS. 28 and 29 do not have to be coplanar with respect to any of the electrode ends 26 of the respective reference electrodes 18, but preferably, respective counter electrode ends 28 are substantially coplanar with respect to respective reference electrode ends 26 and working electrode ends 24A, 24B, and 24C. The ionically conductive surface 23 of the dielectric 22 between the respective reference electrode ends 26 and the working electrode ends 24A, 24B and 24C is also preferably in a substantially coplanar relationship among and with respect to the respective reference electrode ends 26 and the working electrode ends 24A, 24B and 24C. As was seen for the embodiment of the corrosion probe 12 in FIGS. 2-11 and FIGS. 22-27 but not shown in FIGS. 28, 29, 32 and 33, the corrosion probe 12 (of FIGS. 28, 29, 32 and 33) may additionally comprise the sheath 30 that terminates into the sheath end 32. The dielectric 22, preferably without the ionically conductive surface 23, may also be positioned between the outer counter electrode 20 in FIGS. 28 and 29, or between the outer reference electrode 18 in FIGS. 32 and 33, and the sheath 30. If the sheath 30 was included in the embodiment of the corrosion probe 12 in FIGS. 28, 29, 32 and 33, the sheath end 32 and the dielectric 22 between the outer counter electrode 20 and the sheath 30 in FIGS. 28 and 29, or between the outer reference electrode 18 and the sheath 30, in FIGS. 32 and 33, would be preferably, but not necessarily, also substantially coplanar with respect to the counter electrode ends 28, the reference electrode ends 26, the working electrode ends 24A, 24B and 24C, and the ionically conductive surface 23 between the respective reference electrode ends 26 and the working electrode ends 24A, 24B, and 24C.

Figure 30:
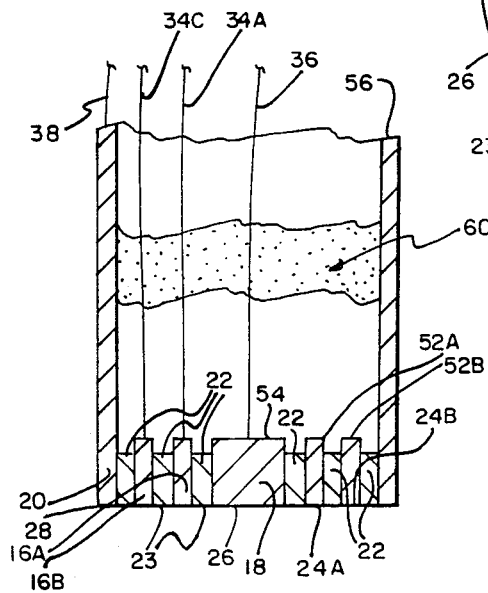
FIG. 30 is a partial vertical sectional view of the corrosion probe with two working electrodes of diverse metals between a reference electrode and a counter electrode.

In a third embodiment (illustrated in FIGS. 30 and 31) of the embodiment of the corrosion probe 12 having more than one working electrode 16 of different metals, the corrosion probe 12 comprises only one reference electrode 18, only one counter electrode 20, and a plurality of working electrodes 16 of different or diverse metals such that the corrosion rate upon each of the diverse metals of the working electrodes 16 in the corrosive liquid environment may be measured sequentially as will be explained below in greater detail. In FIG. 30 the corrosion probe 12 comprises in seriatim reference electrode 18, working electrode 16A, working electrode 16B and counter electrode 20 which also functions as a sleeve. In FIG. 31 the corrosion probe 12 has an additional working electrode 16, and the position of the reference electrode 18 has been interchanged with the position of the counter electrode 20. More specifically, the electrodes of the corrosion probe 12 are arranged serially as follows: counter electrode 20, working electrode 16A, working electrode 16B, working electrode 16C, and reference electrode 18 which also functions as a sleeve. As illustrated in FIGS. 30 and 31, the dielectric 22 is positioned between all electrodes to separate them, and the ionically conductive surface 23 is on the surface of the dielectric 22 in FIG. 30 between the reference electrode 18 and the working electrode 16A and between the working electrodes 16A and 16B. In FIG. 31 the ionically conductive surface 23 is on the surface of the dielectric 22 between working electrodes 16A and 16B, between working electrodes 16B and 16C, and between working electrode 16C and its reference electrode 18. The surface of the dielectric 22 in FIG. 30 between the working electrode 16 and the counter electrode 20, and the surface of the dielectric 22 in FIG. 31 between the counter electrode 20 and the working electrode 16A, do not have or have to have the ionically conductive surface 23. Working electrodes 16A, 16B (in FIGS. 30 and 31) and 16C (in FIG. 31) terminate into working electrode ends 24A, 24B, and 24C, respectively, which are substantially in a coplanar relationship among and with respect to the reference electrode end 26 of the reference electrode 18. As was seen for the embodiment of the corrosion probe 12 in FIGS. 22-27, and FIGS. 28, 29, 32 and 33, the counter electrode end 28 of the counter electrode 20 in FIGS. 30 and 31 does not have to be coplanar with respect to the electrode ends 26 of the reference electrodes 18, but preferably, counter electrode end 28 is substantially coplanar with respect to the reference electrode end 26 and working electrode ends 24A, 24B (in FIGS. 30 and 31) and 24C (in FIG. 31). The ionically conductive surface 23 of the dielectric 22 in FIG. 30 between the reference electrode end 26 and working electrode end 24A and between the working electrodes end 24A and 24B, and the ionically conductive surface 23 of the dielectric 22 in FIG. 31 between the reference electrode end 26 and working electrode end 24C, between working electrode ends 24C and 24B, and between working electrode ends 24B and 24A, are also preferably in a substantially coplanar relationship among and with respect to the reference electrode end 26 and the working electrode ends 24A, 24B (in FIGS. 30 and 31) and 24C (in FIG. 31). .As was seen for the embodiment of the corrosion probe 12 FIGS. 2-11 and FIGS. 22-27 but not shown in FIGS. 30 and 31, the corrosion probe 12 (of FIGS. 30 and 31) may additionally comprise the sheath 30 that terminates into the sheath end 32. The dielectric 22, preferably without the ionically conductive surface 23, may also be positioned between the counter electrode 20 in FIG. 30, or between the reference electrode 18 in FIG. 31, and the sheath 30. If the sheath 30 was included in the embodiment of the corrosion probe 12 in FIGS. 30 and 31, the sheath end 32 and the dielectric 22 between the counter electrode 20 and the sheath 30 in FIG. 30, or between the reference electrode 18 and the sheath 30 in FIG. 31, would be preferably, but not necessarily, also substantially coplanar with respect to the counter electrode end 28, the reference electrode end 26, and the working electrode ends 24A, 24B (in FIGS. 30 and 31) and 24C (in FIG. 31), and the ionically conductive surface 23 between any of the electrodes that have ionically conductive surface 23 therebetween.

In the corrosion probe 12 of FIGS. 28-33, depending conductors 36 and 38 attach electrically to the or any reference electrode(s) 18 and the or any counter electrode(s) 20, respectively. Also, depending conductors 34A and 34B attach electrically to the working electrodes 16A and 16B, respectively. In the embodiment of the corrosion probe 12 of FIGS. 28-33 having a third working electrode 16C (see FIGS. 28, 29, 31-33), depending conductor 34C attaches to working electrode 34C.

For the embodiment of the corrosion probe 12 in FIGS. 28, 29, 32 and 33, one or more device(s) 39 interconnect electrically with at least three (or a set) of the depending conductors respectively extending from one of the working electrodes 16 (i.e. 16A or 16B or 16C), from one of the reference electrodes 18, and from one of the counter electrodes 20, depending upon whether or not the corrosion rate upon each of the diverse metals of the working electrodes 16 in the corrosive liquid environment is to be measured simultaneously or sequentially. If the corrosion rate upon each of the diverse metals of the working electrodes 16 is to be measured simultaneously, more than one device 39 comprising the potentiostat 40 and the signal generator 42 is employed. More specifically for the corrosion probe 12 in FIGS. 28 and 29, one potentiostat 40 would electrically connect to one set of depending conductors comprising depending conductors 36, 34A and 38 and extending respectively from the center reference electrode 18, from the working electrode 16A, and from the counter electrode 20 that is positioned between working electrodes 16A and 16B. A second potentiostat 40 would electrically connect to a second set of depending conductors consisting of depending conductors 38, 34B and 36 and extending respectively from the counter electrode 20 that is situated between working electrodes 16A and 16B, from the working electrode 16B, and from the reference electrode 18 that is positioned between working electrodes 16B and 16C. A third potentiostat 40 would electrically connect to a third set of depending conductors consisting of depending conductors 36, 34C and 38 and extending respectively from the reference electrode 18 that is located between working electrodes 16B and 16C, from the working electrode 16C, and from the outer counter electrode 20. Three signal generators 42—42—42 would respectively engage electrically the three potentiostats 40—40—40 for instructing or signaling a predetermined known current or known difference in potential to the three potentiostats 40—40—40 which would transmit the same through certain of the previously mentioned sets of the depending conductors as will be explained hereafter.

If the corrosion rate upon each of the diverse metals of the working electrodes 16A, 16B and 16C in the corrosion probe 12 in FIGS. 32 and 33 is to be measured simultaneously, three potentiostats 40—40—40 (electrically engaged respectively to three signal generators 42—42—42) would also be employed. One potentiostat 40 would electrically connect to a set of depending conductors comprising depending conductors 38, 34A, and 36 and extending respectively from the center counter electrode 20, from the working electrode 16A, and from the reference electrode 18 that is located between working electrodes 16A and 16B. The second potentiostat 40 would electrically connect to a second set of depending conductors consisting of depending conductors 36, 34B and 38 and extending respectively from the reference electrode 18 that is positioned between working electrodes 16A and 16B, from the working electrode 16B, and from the counter electrode 20 that is placed between working electrodes 16B and 16C. The third potentiostat 40 would electrically connect to a third set of depending conductors consisting of depending conductors 38, 34C and 36 and extending respectively from the counter electrode 20 that is situated between working electrodes 16B and 16C, from the working electrode 16C, and from the outer reference electrode 18. Identical to the embodiment of the corrosion probe 12 in FIGS. 28 and 29, the three signal generators 42—42—42 would instruct or signal a predetermined known current or known difference in potential to the three potentiostats 40—40—40 which would respectively transmit or apply the same through or between certain of the previously mentioned sets of the depending conductors as will be explained hereafter.

If the corrosion rate upon each of the diverse metals of the working electrodes 16A, 16B, and 16C in the corrosion probe 12 in FIGS. 28, 29, 32 and 33 is to be measured sequentially, only one device 39 (or one potentiostat 40 and one signal generator 42) is employed. More particularly with respect to the corrosion probe 12 in FIGS. 28 and 29 for sequentially measuring the corrosion rate upon the diverse metals of the working electrodes 16A, 16B and 16C, a potentiostat 40 would be electrically connected to one set of depending conductors, such as by way of example only: the set of depending conductors 36, 34A and 38 extending respectively from the center reference electrode 18, from the working electrode 16A, and from the counter electrode 20 that is located between working electrodes 16A and 16B. After the corrosion rate from the corrosive liquid environment has been determined on working electrode 16A as will be explained in greater detail below, the potentiostat 40 is disconnected from depending conductor 36, 34A and 38, and electrically connected to another set of depending conductors to determine the corrosion rate upon another working electrode 16, such as by way of example again: the set of depending conductors 38, 34B and 36 extending respectively from the counter electrode 20 that is located between working electrodes 16A and 16B, from the working electrode 16B (whose corrosion rate in the corrosive liquid environment is to be determined), and from the reference electrode 18 that is situated between working electrodes 16B and 16C; or the set of depending conductors 36, 34C and 38 extending respectively from the reference electrode 18 that is positioned between working electrodes 16B and 16C, from the working electrode 16C (whose corrosion rate in the corrosive liquid environment is to the determined), and from the outer counter electrode 20. A signal generator 42 would instruct or signal a predetermined known current or known difference in potential to the potentiostat 40 which would respectively transmit or apply the same through or between the particular set of depending conductors electrically engaged to the potentiostat 40 as will be explained hereafter.

Similarly, if the corrosion rate upon the diverse metals of the working electrodes 16A, 16B and 16C in the corrosion probe 12 of FIGS. 32 and 33 is to be measured sequentially, a potentiostat 40 would be connected initially to one of the following sets of depending conductors: depending conductors 38, 34A and 36 extending respectively from the center counter electrode 20, from the working electrode 16A (whose corrosion rate in the corrosive liquid environment is to be determined), and from the reference electrode 18 that is located between working electrodes 16A and 16B; depending conductors 36, 34B and 38 extending respectively from the reference electrode 18 that is placed between working electrodes 16A and 16B, from the working electrode 16B (whose corrosion rate in the corrosive liquid environment is to be determined), and from the counter electrode 20 that is situated between working electrodes 16B and 16C; and depending conductors 38, 34C and 36 extending respectively from the counter electrode 20 that is positioned between working electrodes 16B and 16C, from the working electrode 16C (whose corrosion rate in the corrosive liquid environment is to be determined), and from the outer reference electrode 18. After the corrosion rate from the corrosive liquid environment has been determined on the particular working electrode 16 (i.e. 16A, 16B or 16C) secured to one of the depending conductors (i.e. 34A, 34B or 34C) within a set of depending conductors, the potentiostat 40 is disconnected and connected electrically to another set of depending conductors to determine the corrosion rate upon another working electrode 16 (i.e. 16A, 16B or 16C) secured to one of the depending conductors (i.e. 34A, 34B. or 34C) within said another set of depending conductors. The process or method is continued until the corrosion rate from the corrosive liquid environment upon all working electrodes 16A, 16B and 16C have been determined.

In the embodiment of the corrosion probe 12 in FIGS. 30 and 31, the corrosion rate upon each of the diverse metals of the working electrodes 16A, 16B (in FIGS. 30 and 31) and 16C (in FIG. 31) is measured sequentially and only one potentiostat 40 and one signal generator 42 is utilized. More specifically with respect to the corrosion probe 12 in FIG. 30, the potentiostat 40 would be electrically connected to one set of depending conductors, such as depending conductors 36, 34A and 38 extending respectively from reference electrode 18, working electrode 16A (whose corrosion rate in the corrosive liquid environment is to be determined) and counter electrode 20; or depending conductors 34A, 34B and 38 extending respectively from working electrode 16A (which now functions as a reference electrode 18 as will be explained in greater detail below), working electrode 16B whose corrosion rate in the corrosive liquid environment is to be determined), and counter electrode 20. After the corrosion rate from the corrosive liquid environment has been determined on one of the particular working electrodes 16A or 16B, the potentiostat 40 is disconnected and connected electrically to the other set of depending conductors to determine the corrosion rate upon the other working electrode 16A or 16B. With respect to the corrosion probe 12 in FIG. 31, a potentiostat 40 would be electrically connected to one of the following sets of depending conductors: depending conductors 38, 34A and 34B extending respectively from counter electrode 20, working electrode 16A (whose corrosion rate in the corrosive liquid environment is to be determined), and working electrode 16B (which now functions as a reference electrode 18 as will be explained in greater detail hereinafter); depending conductors 38, 34B and 34C extending respectively from counter electrode 20, working electrode 16B (whose corrosion rate in the corrosive liquid environment is to be determined) and working electrode 16C (which now functions as a reference electrode 18 as will also be explained in greater detail hereinafter); and depending conductors 38, 34C and 36 extending respectively from counter electrode 20, working electrode 16C (whose corrosion rate in the corrosive liquid environment is to be determined), and reference electrode 18. After the corrosion rate from the corrosive liquid environment has been determined on one of the particular working electrodes 16A, 16B, or 16C (e.g. working electrode 16A) in the corrosion probe 12 of FIG. 31, the potentiostat 40 is disconnected and electrically connected to another set of depending conductors to determine the corrosion rate upon another working electrode 16A, 16B or 16C (e.g. either working electrode 16B or 16C if the corrosion rate was initially determined on working electrode 16A).

In the embodiment of the corrosion probe 12 in FIGS. 28-33, if the corrosion rate upon each of the diverse metals of the working electrodes 16A, 16B (in FIGS. 30 and 31) and 16C (in FIG. 31) is to be measured sequentially with one potentiostat 40 and one signal generator 42, then the period of time between the taking of readings, measurements, and determining the corrosion rate upon the diverse metal of one working electrode 16 and the taking of readings, measurements, and determining the corrosion rate upon the diverse metal of another working electrode 16 should be as short as possible; preferably less than about one (1) minute, more preferably less than about ten (10) seconds. With a short time frame such as about ten (10) seconds between determining the corrosion rate upon any particular two working electrodes 16 (e.g. 16A and 16B), the environment of the corroding working electrodes 16 will not be artificially changed, such as from excess negative current evolving hydrogen bubbles which will stir the thin film of aqueous phase on the metal surface of the corroding working electrode 16. The stirring action will change the concentrations of the corroding acid. Similarly, excess positive current can artificially thicken the insoluble oxidized metal phase on the metal surface of the corroding working electrode 16, and/or excess positive current can artificially generate pits and crevices on the same.

The remaining features of the embodiment of the corrosion probe 12 in FIGS. 28–33 are generally identical or similar to the features of the corrosion probe 12 in FIGS. 10, 11 and FIGS. 22, 23. More specifically with respect to the remaining features of the corrosion probe 12 in FIGS. 28–33, all reference electrode ends 26 and all counter electrode ends 28 have a reference electrode opposed end 54 and a counter electrode opposed end 56, respectively. All working electrode ends 24A, 24B and 24C have a working electrode opposed ends 52A, 52B and 52C, respectively. In the embodiment df the corrosion probe 12 depicted in FIGS. 28–30, the center reference electrode 18 is shaped as a cylinder and all remaining reference electrodes 18 and all working electrodes (i.e. 16A, 16B, and 16C) are essentially cylindrical rings circumferentially surrounding the center reference electrode 18 and concentrically positioned with respect thereto. All counter electrodes 20 are also essentially cylindrical rings that circumferentially surrounds the center reference electrode 18 and are also concentrically positioned with respect to the same. The outer counter electrode 20, in addition to being an electrode, defines a sleeve with an inner cylindrical wall and has a much greater length than the other electrodes. In the embodiment of the corrosion probe 12 depicted in FIGS. 31–33, the center counter electrode 20 is shaped as a cylinder and all remaining counter electrodes 20 and all working electrodes (i.e. 16A, 16B, and 16C) are essentially cylindrical rings circumferentially surrounding the center counter electrode 20 and concentrically positioned with respect thereto. All reference electrodes 18 are also essentially cylindrical rings that circumferentially surround the center counter electrode 20 and are also concentrically positioned with respect to the same. The outer reference electrode 18, in addition to being an electrode in FIGS. 31–33, defines a sleeve with an inner cylindrical wall and has a much greater length than the other electrodes. The void space within the inner cylindrical wall of the outer counter electrode 20 in FIGS. 28, 29 and 30 and within the inner cylindrical wall of the outer reference electrode 18 in FIGS. 31, 32 and 33 may be defined (as it was for the embodiment of the corrosion probe 12 in FIGS. 22, 26, and 27) as the available space from any of the opposed ends (i.e. 52A, 52B, 52C, 54 and 56) of any of the electrodes (i.e. 16A, 16B, 16C, 18, and 20) within the inner cylindrical wall of the outer counter electrode 20 or the outer reference electrode 18 up to a space extremity that generally registers with the opposed end 56 of the outer counter electrode 20 or the opposed end 54 of the outer reference electrode 18, respectively. The retaining material 60 is positioned generally in each of the void spaces for the embodiments of FIGS. 28–33. All depending conductors (i.e. 34A, 4B, 34C, 36 and 38) extend from any of the opposed dnds (i.e. 52A, 52B, 52C, 54, and 56) of any of the electrodes within the inner cylindrical wall of the outer counter electrode 20 or the outer reference electrode 18 through and beyond the retaining material 60.

Dimensional features for the embodiment of the corrosion probe 12 in FIGS. 28–33 are essentially identical to the dimensional features of the corrosion probe 12 in FIGS. 6–11 with the center counter electrode 20 or the center reference electrode 18 having a diameter of less than 0.25 inches (more preferably from about 0.01 inches to about 0.20 inches), and the thickness of any and all cylindrical electrodes, especially including their respective cylindrical electrode ends, is less than about 0.25 inches (more preferably from about 0.01 to about 0.15 inches). Similarly, the width of the ionic conductive surface 23 between any electrode ends is preferably about 0.35 inches or less (more preferably from about 0.01 inches to about 0.20 inches). The width of the dielectric 22 between any electrode ends (such as between working electrode 16A and counter electrode 20 in FIG. 28) and not possessing the ionic conductive surface 23, as was seen for the embodiment of the corrosion probe 12 in FIGS. 22–27, depends on the amount of power that can be transmitted to the corrosion probe 12 from the device 39, the conductivity of the corrosive liquid, etc., but as a matter of economics is no more than about 0.5 inches.

The variable resistor 46, meter 48 and voltmeter 50 (see FIG. 1) would also be employed in the embodiment of the corrosion probe 12 in FIGS. 28–33 to function similarly to the way they functioned for the embodiment of the corrosion probe 12 in FIGS. 2–11, as will be explained in greater detail below.

While the embodiment of the corrosion probe 12 in FIGS. 28–33 comprises two (i.e. 16A and 16B) or three working electrodes (i.e. 16A, 16B and 16C) of diverse metals, it should be understood that the spirit and the scope of this invention would include a corrosion probe 12 comprising four (4) or more working electrodes. For example, a six (6) working electrode probe of the embodiment of the corrosion probe 12 in FIGS. 28 and 29 would have the following sequence of electrodes starting at the center of the probe 12 (with R=reference, W=working, and C=counter): R W C W R W C W R W C W R ... The surface of the dielectric 22 between any working electrode 16 and any reference electrode 18 would possess the ionic conductive surface 23. Likewise, while the embodiment of the corrosion probe 12 in FIGS. 28–33 comprises a cylinder and cylindrical electrodes, it should be understood that the spirit and the scope of this invention would comprise a corrosion probe 12 having all electrodes in the form of rectangular plates, similar to the corrosion probe 12 illustrated in FIGS. 2 and 3. In such corrosion probe 12 the rectangular electrodes would be serially arranged in accordance with the serial arrangement and/or proper sequence of the electrodes of the corrosion probe 12 in FIGS. 28–33, and the ionic conductive surface 23 would be appropriately positioned on the dielectric 22 between any working electrode 16 and any reference electrode 18.

The working electrode 16 (as well as 16A, 16B and 16C) may be fabricated of any metal, the corrosion rate of which in the corrosive liquid environment is to be determined. Preferably, working electrodes 16A, 16B, or 16C are manufactured of different or diverse metals, but any one of the working electrodes 16A, 16B, or 16C may be manufactured to comprise the same or identical metal that one or more of the other or remaining working electrode comprises. If any of the working electrodes 16, 16A, 16B or 16C is not manufactured of the same metal whose corrosion rate in the corrosive liquid environment is to be determined, then the corrosion rate relationship between the actual metal of the working electrode 16 (or 16A, 16B, or 16C) and the metal whose corrosion rate in the corrosive liquid environment is desired, should be known. For example, a certain class of low alloy steel would include a number of specific steel materials that would corrode at different absolute rates, which may well be different by a factor (e.g. 2, 3, or etc.) depending on the exact alloy, but the relative change in corrosion rate with the change in fluid environment (e.g., temperature, pressure, salt composition, etc.) would be generally identical. Preferably, working electrode 16 or at least one of the working electrodes 16A, 16B, or 16C is made from ferrous metal such as steel or a low alloy carbon steel.

In the embodiment of the corrosion probe 12 in FIGS. 2-11, counter electrode 20 is provided to permit the completion of a power circuit between working electrode 16 and counter electrode 20, whereby a current may be applied as follows: through the working electrode 16, over the ionically conductive dielectric surface 23 between the working electrode end 24 and the reference electrode end 26, over the ionically conductive dielectric surface 23 between the reference electrode end 26 and the counter electrode end 28, and through the counter electrode 20.

With respect to the embodiment of the corrosion probe 12 in FIGS. 12-27, the counter electrode 20 (or conductive means) is provided to permit the completion of a power circuit between working electrode 16 and counter electrode 20 (or conductive means), whereby a current may be applied as follows: through the working electrode 16, through the corrosive liquid environment (e.g. corrosive liquid 7), and through the counter electrode 20 (or through the conductive means).

In FIGS. 28 and 29 two counter electrodes 20—20 are provided to permit the completion of a power circuit between working electrodes 16A and 16B and one counter electrode 20, and between working electrode 16C and the second (or outer) counter electrode 20, whereby current may be applied as follows: through working electrodes 16A, 16B and 16C, through the corrosive liquid environment, and through both counter electrodes 20—20. The current that flows through working electrodes 16A and 16B returns through the counter electrode 20 that is between them, and the current that flows through working electrode 16C returns through the outer counter electrode 20. Two counter electrodes 20—20 are also provided in FIGS. 32 and 33 to permit the completion of a power circuit between working electrode 16A and the center counter electrode 20, and between working electrodes 16B and 16C and the second counter electrode 20, whereby current may be applied as follows: through working electrodes 16A, 16B and 16C, through the corrosive liquid environment, and through both counter electrodes 20—20. The current that flows through working electrode 16A returns through the center counter electrode 20, and the current that flows through working electrodes 16B and 16C returns through the counter electrode 20 that is positioned between electrodes 16B and 16C. In FIGS. 30 and 31 only one counter electrode 20 is provided for the sequential measurement of the corrosion rate from the corrosive liquid environment upon working electrodes 16A and 16B (in FIGS. 30 and 31) and 16C (in FIG. 31). In FIG. 30 current may be applied as follows: through working electrode 16B, through the corrosive liquid environment, and through the counter electrode 20. Current may also be applied in FIG. 30 through the working electrode 16A, over the ionically conductive dielectric surface 23 between the working electrodes 16A and 16B, through the corrosive liquid environment, and through the counter electrode 20.

In FIG. 31 current may be applied as follows: through working electrode 16A, through the corrosive liquid environment, and through the center counter electrode 20. Current may also be applied in FIG. 31 in the following two other manners: through the working electrode 16B, over the ionically conductive dielectric surface 23 between the working electrodes 16B and 16A, through the corrosive liquid environment, and through the counter electrode 20; and through the working electrode 16C, over the ionically conductive dielectric surface 23 between the working electrodes 16C and 16B, over the working electrode end 24B and across the ionically conductive dielectric surface 23 between the working electrodes 16B and 16A, through the corrosive liquid environment, and through the counter electrode 20.

While counter electrode 20 may be fabricated of any material such as a ferrous metal (e.g. steel), it is preferably inert; that is, fabricated of a material such as carbon, graphite, or platinum which undergoes no reaction under the application of an electric potential when exposed to the corrosive liquid environment. In this manner, contamination of the corrosive liquid environment with undesired reaction products is avoided.

Reference electrode 18 may also be fabricated of any conductive material, but is preferably a reversible electrode in that more accurate measurements are made possible, since a fixed potential between a reference electrode end 26 and an area in a surrounding fluid means (i.e. the corrosive liquid environment such as an oil/brine mixture) in general microscopic proximity thereto is not altered by the passage of minute currents to or from the reference electrode end 26. Although low alloy carbon steel has been proved suitable for use as a reference electrode 18 in the corrosion probe 12 of the present invention, the theory of the technique indicates that other metals and metal alloys, e.g. calomel, hydrogen, copper-copper sulfate, silver-silver chloride, and aluminum, copper, brass, lead, nickel, titanium, zirconium, chromium, and alloys thereof, may be used under similar conditions. The use of a reference electrode 18 that is of the same metal as the sample or working electrode is advantageous s in that it permits a short test period, permits use of high temperatures and pressure, and permits the use of the most sensitive range of meter 50. In a preferred embodiment for the corrosion probe 12, working electrode 16, reference electrode 18 and counter electrode 20 are manufactured of the same material to overcome any other possible difficulties normally encountered when taking potential measurements utilizing the reference electrode 18.

The sheath 30 may be fabricated of any suitable material which would be protective of the dielectric 22, the electrodes 16, 18 and electrode 20 (if employed) affixed within the dielectric 22, and the retaining material 60 which holds and retains the dielectric 22 (including the electrodes 16, 18 and 20) in place. In a preferred embodiment of the corrosion probe 12, sheath 30 is manufactured of a highly corrosion resistant material, say stainless steel or the like.

In the preferred embodiments of the corrosion probe 12 depicted in FIGS. 6, 7 and 11, 23, 24 and 25, the spacing of the sheath 30 from the counter electrode 20, or the thickness of the dielectric 22 between the sheath 30 and the counter electrode 20, may be any suitable reasonable spacing or thickness, such as from about 0.01 to about 1.00 inch. This is not critical because the surface of the dielectric 22 between the counter electrode 20 and the sheath 30, or between the counter electrode end 28 and the sheath end 32, can be an inactive surface and not ionically conductive, such as the ionic conductive surface 23 between the electrode ends 24 and 26. There is no need for the surface of the dielectric 22 between the counter electrode 20 and the sheath 30 to be ionically conductive.

Likewise, in the preferred embodiments of the corrosion probe 12 depicted in FIGS. 2 and 3, the distance that any of electrodes 16, 18 and 20 are from the sheath 30 is not critical or important and may be any suitable reasonable distance, such as from about 0.01 to about 1.00 inch. The surface of the dielectric 22 from any of the electrode ends 24, 26 and 28, across the retaining material 60, to the sheath end 32 of sheath 30 is inactive and not ionically conductive such as the ionic conductive surface 23 positioned between any two contiguous electrode ends i.e. either electrode ends 24 and 26 or electrode ends 26 and 28.

Similarly, in the preferred embodiments of the corrosion probe 12 depicted in FIGS. 16, 18, 19, 20 and 21, the distance that any of electrodes 16, 18 are from the sheath 30 is not critical or important and may be any suitable reasonable distance, such as from about 0.01 to about 1.00 inch. The surface of the dielectric 22 from any of the electrode ends 24 and 26 across the retaining material 60, to the sheath end 32 of sheath 30 is inactive and not ionically conductive such as the ionic conductive surface 23 positioned between the two contiguous electrode ends (i.e. between electrode ends 24 and 26).

The material of the dielectric 22 for this invention may be any suitable insulation, such as Teflon, glass, fiber, plastic (e.g. polystyrene), resins (e.g. phenolics), fluorocarbons, polymers, or combinations of two or more polymers which are formulated to provide particular properties or characteristics (e.g. interpenetrating polymer networks) or mixtures of the same, which by structure, formulation and/or processing have, or can be made to have an ionic conductive surface 23; and can or can be made to withstand the temperatures, pressure, solvency, and other conditions experienced during the corrosion measurement. By way of example only, the dielectric 22 may be a phenolic resin. Formulation of the dielectric 22 for the purposes of this invention would include changes made in the polymerization process to produce the polymer, and/or addition of material(s) to the polymer to produce a modified polymer or a polymer composite.

The material of the dielectric 22 separating the electrodes within all embodiments of the corrosion probe 12 of the invention may be the same throughout the entire structure of the corrosion probe 12, or the material of the dielectric 22 separating one pair of electrodes may be different from the material separating another pair of electrodes. The material of the dielectric 22 separating a particular pair or pairs of electrodes may also be of differing composition at the electrode ends and the opposing ends with the compositions and fractions of length for each material based on desired properties including properties of the ionic conducting surface 23.

For example, the material of the dielectric 22 separating the working electrode 16 from the reference electrode 18 may be or comprise polystyrene plastic, and the material of the dielectric 22 separating the reference electrode 18 from the counter electrode 20 may be or comprise phenolic resin.

For the embodiments of the corrosion probe 12 in FIGS. 2-11, the high resistances of the dielectric 22 between all electrode ends 24, 26 and 28 are lowered by imbedding or chemically generating ionic functions on the surface of the dielectric 22 that separates the electrodes 16, 18 and 20, including their respective electrode ends 24, 26 and 28, in order to define the ionic conductive surface 23.

Similarly, for the embodiments of the corrosion probe 12 in FIGS. 12-27, the high resistances of the dielectric 22 between all electrode ends 24 and 26 are lowered by imbedding or chemically generating ionic functions on the surface of the dielectric 22 that separates the electrode ends 24 and 26 in order to define the ionic conductive surface 23. FIGS. 4 and 16 illustrate a plurality of ionically conductive negative charged ions chemically bound to the surface of the dielectric 22; and FIGS. 5 and 17 depict a plurality of alternating negative and positive charged ions imbedded in the dielectric surface 23.

In one embodiment, the required "artificial" charge carriers are induced by chemical modification of the surface of the dielectric 22 by caustic or acidic etching (e.g. with KOH or a mixture of 40% by wt. KOH and 30% by wt. $H_2O_2$, or the like) of the phenolic based resins or oxidative sulfonation (e.g. a mixture of $H_2O_2$ in H of the polystyrene resins. Some polymers, copolymers, and/or polymer composites and other such compositions known in the art, may contain such ionically conductive charged ions as a result of their structure, formulation, and/or processing and do not require any additional chemical treatment. Chemical etching treatments function to decrease resistivity of the dielectric 22 to obtain the ionic conductive surface 23 by generating nominally a monolayer of permanently bound surface ion exchange groups and/or generating a water-wettable surface which may, or may not, have permanent surface ions, but which would absorb or adsorb water and ions from the corrosive liquid environment (e.g. an oil and brine mixture).

In another embodiment of this invention, any surface of the dielectric 22 may be made ionically conductive by initially contacting the surface of the dielectric 22 of the corrosion probe 12 with a surfactant, and subsequently inserting the corrosion probe 12 into a corrosive liquid environment. The corrosive liquid environment or media is preferably not conductive but contains a disperse phase which consists of an ionically conductive solution. A suitable corrosive liquid environment containing an ionically conductive solution has been determined to be, by way of illustration only, brine-in-liquid hydrocarbon mixtures such as a brine-in-motor oil, brine-in-crude oil, etc. For such corrosive liquid environments, it is believed that the surfactant is adsorbed on, or adheres to (or the like) the dielectric surface, and causes the dielectric surface to become preferentially water wettable; and water contained in the disperse phase (e.g. brine) droplets, which are suspended in the hydrocarbon phase, donates ions (e.g. salt) to the water-surfactant-dielectric surface, making it ionically conductive. This now ionically conductive surface allows corrosion rates to be measured by the previously described electrochemical means.

In order to prepare a surface of the dielectric 22 of any of the embodiments of the corrosion probe 12 to become ionically conductive when the probe 12 is inserted into a corrosive liquid environment, such surface of the dielectric 22 has to be contacted with a surfactant which is capable of rendering the surface of the dielectric 22 ionically conductive when the probe 12 is inserted or placed into the corrosive liquid environment. The surface of the dielectric 22 to be prepared may be contacted with the surfactant through or by any suitable means, such as, by way of example only, painting or wiping the surfactant onto the substantially planar end of the corrosion probe 12, or by dipping or immersing the substantially planar end of the corrosion probe 12 into the surfactant. The surface of the dielectric 22 should be contacted with the surfactant for a sufficient period of time, preferably from about one (1) sec. to about one (1) minute. After the surfactant has contacted the surface of the dielectric 22 to be prepared, excess surfactant fluid is wiped or rinsed off, and the corrosion probe 12 is now ready to be inserted into the corrosive liquid environment.

The surfactant, or mixtures of surfactants, that are capable of rendering any surface of the dielectric 22 ionically conductive when exposed to an ionically conductive solution within a corrosive liquid environment may be either ionic or nonionic.

Suitable nonionic surfactants may be ethoxylated alkyl phenols possessing the general formula:

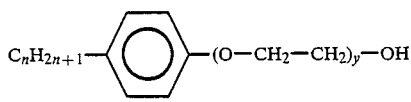

wherein n is from about 8 to about 12 any y is from about 3 to about 100. Other suitable nonionic surfactants are bifunctional any may be ethoxylated dialkyl phenols possessing the general formula:

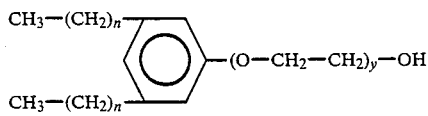

wherein n is from about 4 to about 11 and y is from about 3 to about 100.

A particular suitable ethoxylated alkylphenol surfactant of the nonylphenol family has been determined to be one sold under the trademark IGEPAL CO-170 of General Aniline & Film Corp.

Suitable ionic surfactants may be sodium alkyl aryl sulfonates having the general formula:

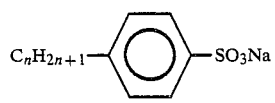

wherein n is from 1 to about 15. The suitable ionic surfactant may possess no alkyl group and be sodium benzene sulfonate with the general formula:

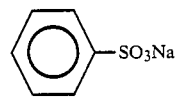

The suitable ionic may be bifunctional and have the general formula:

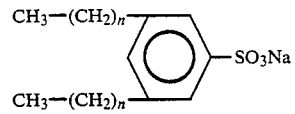

where n is from 1 to bout 15, or n may be zero (0) wherein the suitable bifunctional ionic surfactant is sodium m-xylene sulfonate having the formula:

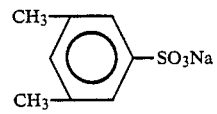

A particular suitable ionic surfactant has been discovered to be the one sold under the trademark Witconate P-10-59 of Witco Chemical Corp.

It is believed that the effectiveness of a particular surfactant may be related to the type or kind of dielectric 22 employed. For example, certain surfactants may activate the surface of an epoxy dielectric 22 and others may not, or may not be as effective. Similarly, if the dielectric 22 is made from another insulator, such as Teflon, glass, fiber, or plastic (e.g. polystyrene), some surfactants are more effective than others. It should be understood that while a surfactant, or a mixture of surfactants, has been disclosed as a means for activating the surface of the dielectric 22 in order to make or render it ionically conductive when immersed into a corrosive liquid environment, other means (e.g. radiation exposure, ion exposure, electrical charge, chemical exposure, absorption into the dielectric 22, adsorption on, adherence to, or coating of the surface of the dielectric 22, or the like for such other means) for activating the surface of the dielectric 22 are encompassed within the spirit and scope of this invention.

The corrosive liquid environment in the present invention may be any corrosive liquid environment such as, but not by way of limitation, carbon dioxide-saturated brine, carbon dioxide-saturated oil/brine, ordinary brine containing mixed chlorides such as calcium and magnesium, oil well brines, water for use in secondary recovery of oil, recirculating cooling water, any hydrocarbon/brine mixture, or any corrosive liquid environment containing not only chlorides such as calcium and magnesium, but also other ions such as sulfide, ferrous, ferric, cuprous or other readily oxidized or reduced ions. The present invention is particularly suited for measuring corrosion of steel in mixtures of brine suspended in oil (as opposed to mixtures of oil suspended in brine) since no present state of the art electrochemical probes can accomplish this.

With continuing reference to the drawings for operation of the invention and the process for measuring the corrosion rates of metals, or the like, in a corrosive liquid environment, such as a brine/oil mixture, the particular desired embodiment of the corrosion probe 12 is initially prepared. Working electrodes 16, 16A, 16B, and 16C are the sample electrodes upon which the effects of the corrosive liquid environment are to be determined. All reference electrodes 18, preferably reversible, maintain a fixed potential for use in measuring the potential difference of any of the working electrodes during current flow. The counter electrode 20, or the current conductive means, carries the small test currents between it and any particular working electrode (i.e. 16, 16A, 16B, or 16C). The corrosion current is computed from the current/potential profile of the working electrode 16, 16A, 16B or 16C.

The electrodes 16, 18 and 20 in FIGS. 2-11 and FIGS. 22-27, and electrodes 16 and 18 for the embodiment of FIGS. 12-20, are positioned at a preferred spacing of about 1.5 mm or a little less than about 0.05 inches. For the embodiment of the corrosion probe 12 in FIGS. 28-33 all working electrodes (i.e. 16A, 16B, and 16C), all reference electrodes 18, and all counter electrodes 20 are separated from each other at the preferred spacinq of about 1.5 mm. For the embodiment of the corrosion probe 12 in FIGS. 2-11, the magnitude of the interelectrode resistance is reduced by decreasing the interelectrode spacing and/or increasing the ionic conductivity of the dielectric surface material 23 between the electrodes 16, 18 and 20. For the embodiment of the corrosion probe 12 in FIGS. 12-27, the magnitude of the interelectrode resistance between the working electrode 16 and the reference electrode 18 is also reduced by decreasing the interelectrode spacing and/or increasing the ionic conductivity of the dielectric surface material 23 between the electrodes 16 and 18. Similarly, in FIGS. 28-33 the magnitude of the interelectrode resistance between working electrodes 16A, 16B, and 16C, and between any of the working electrodes 16A, 16B, and 16C and any reference electrodes 18 is reduced with decreased interelectrode spacing and/or increasing the ionic conductivity of the dielectric surface 23 between any of these electrodes.

Reducing the magnitude of the interelectrode resistance, brings the interelectrode resistance into a regime addressable by commercial ac conductivity bridges. Ohmic interelectrode resistance can therefore be measured with, for example, a Beckman Instrument Model RC-16C, battery powered conductivity bridge, or the like, operating at 1 KHz. The normal dynamic range of this ac bridge is about 0 to 1 megohm, with calibration via standard resistors above 0.2 megohm.

The resistance measuring range of this Beckman Bridge, or any similar bridge, can be extended into the megohm region (and any potential error in measurement reduced) by use of a shunt technique as described by L. Niedrach in the Journal of Electrochemical Soc. 127,2122 (1980). The high, unknown interelectrode resistance is placed in parallel with a smaller, known resistance, within the dynamic range and Rx is computed from the measurement by the standard formula for resistances in parallel. Values accurate to nominally ±10% are obtained in this manner up to 5 megohms.

In the embodiment of the corrosion probe 12 in FIGS. 6-11 and FIGS. 22-27, the electrodes 16, 18 and 20 are manufactured, for purposes of illustrating the operation of this invention, of N80 steel comprising iron and alloying elements. One such N80 steel has the following chemical composition in the accompanying stated by wt. basis: Si 0.26, Mn 1.42, Cr 0.54, Mo 0.016, Ni 0.08, Cu 0.14, V 0.111, Sn 0.006, Al 0.02, B 0.0002, Mg 0.003, P 0.009, S 0.012, and C 0.36. In FIGS. 6-11, the electrodes are arranged as a disc for working electrodes 16 with a diameter of about 0.175 inches, and rings having a uniform thickness of about 0.05 inches for reference electrodes 18 and counter electrode 20. In FIGS. 22-27 the shape and dimensions of the working electrode 16 and the reference electrode 18 are reversed.

In the preferred embodiment of the corrosion probe 12 in FIGS. 2 and 3, the electrodes 16, 18 and 20 are manufactured, for the purpose of illustrating the operation of the invention, with a low alloy steel. This low alloy steel has a corrosion rate per unit area in pure brine that is approximately three times larger than that of the N80 steel described above. The electrodes are arranged as parallel metal strips, as illustrated in FIG. 3, with identical electrodes connected internally in parallel. The width of these electrodes 16, 18 and 20 possessing a parallel relationship is uniform and is about 0.05 inches. In this parallel electrode design, minute droplets of the corrosive liquid environment bridging small sectors of any electrodes 16, 18 and 20 combination would produce a measurable corrosion current. There is no need for the corrosive liquid environment to bridge all of the electrode ends 24, 26 and 28 as would be necessitated for the preferred embodiment of FIGS. 6-11 assuming that the electrode surface area involved in the corrosion process is known if the corrosion current density is to be determined qualitatively as explained below in greater detail.

In the embodiment of the corrosion probe 12 in FIGS. 14-21, the electrodes 16 and 18 are also manufactured, for purposes of illustration, of N80 steel. The electrodes are also arranged such that the reference electrode 18 is a cylindrical disc with a diameter of about 0.175 inches, and the working electrode 16 is a ring having a uniform thickness of about 0.05 inches.

In the corrosion probe 12 of FIGS. 28-33 comprising a plurality of multi-metal working electrodes 16A, 16B, and 16C, all reference electrodes 18 and counter electrodes 20 are fabricated of N80 steel or 316 stainless steel, with certain dimensions as will be described in greater detail hereafter in the examples for purposes of illustrating this embodiment of the corrosion probe 12.

Oil/brine mixtures are prepared as the corrosive liquid environment in illustrating this invention. The crude oils used to make oil/brine mixtures are: Crude A, Crude B, Crude C, Crude D, and Crude E. Six hundred and forty (640) ml of each crude oil are combined with a predetermined desired volume (percentage) of NaCl solution in a 2-liter autoclave. The mixtures are respectively deaerated by pressurizing/depressurizing to 700 psig. with argon, while stirring. The addition of $Na_2SO_3$ removes the last traces of dissolved oxygen. Since the mixtures would separate into sludge-fluid layers on cooling and after venting the carbon dioxide, the mixtures are kept warm, stirred and under $CO_2$ pressure when not in use.

Corrosion probes 12 are prepared for each of the embodiments of the probe 12 using one of the following three dielectrics for each embodiment: Teflon, polystyrene, and phenolic-filled linen. Retaining material 60 (a cured epoxy resin) was used to retain the dielectric 22 including the implanted electrodes 16, 18 and 20 within a stainless steel sheath 30 for the embodiment of FIGS. 2, 3, 6, 7 and 11, and for the embodiment of the probe 12 illustrated in FIGS. 23, 24, and 25. Also within the stainless steel sheath 30 of the probe 12 illustrated in FIGS. 16, 18, 20 and 21, the retaining material 60 was also used to retain the dielectric 22 and the implanted electrodes 16 and 18. In FIGS. 8, 9, 10, 22, 26, and 27, a cured epoxy resin was also used as a retaining material 60 for holding the dielectric 22 having implanted electrodes 16 and 18 within the cylindrical wall of the counter electrode 20.

Also within the cylindrical wall of the counter electrode 20 as illustrated in FIGS. 28, 29 and 30, as well as within the cylindrical wall of the reference electrode 18 as illustrated in FIGS. 31, 32 and 33, the retaining material 60 is used to retain other counter electrodes 20 and other reference electrodes 18 along with the plurality of working electrodes such as 16A, 16B, and 16C. For the embodiment of the corrosion probe 12 in FIGS. 14, 15 and 17, the cured epoxy resin is further used as the retaining material 60 within the cylindrical wall of the working electrode 16.

The surface of the dielectric 22 between electrodes 16 and 18 and between electrodes 18 and 20 for the embodiment of the corrosion probe 12 in FIGS. 2-11 has to be ionically charged to define the ionic conductive surface 23 and lower the interelectrode resistance. The proximal disposition alone of the electrodes 16, 18 and 20 with respect to each other in FIGS. 2-11 will not provide the necessary low interelectrode resistance in order to detect corrosion on the working electrode 16. For the embodiment of the corrosion probe 12 in FIGS. 12-27, the surface of the dielectric 22 between only the working electrode 16 and the reference electrode 18 has to be ionically charged to define the ionic conductive surface 23 and lower the interelectrode resistance. Similarly for the corrosion probe 12 in FIGS. 28-33 comprising a plurality of working electrodes (i.e. working electrodes 16A, 16B, and 16C), the surface of the dielectric 22 between only the working electrodes 16A, 16B, and 16C, and between any of the working electrodes 16A, 16B, and 16C and any of the reference electrodes 18, has to possess the ionic conductive surface 23. The surface of the dielectric 22 between any of the working electrodes 16, 16A, 16B and 16C and any of the counter electrodes 20 does not have to be ionically charged. The proximal disposition along of any of the working electrodes 16, 16A, 16B, and 16C and any of the reference electrodes 18 (including their electrode ends 24, 24A, 24B, 24C and 26) with respect to each other will not provide the necessary low interelectrode resistance in order to detect corrosion on any of the working electrodes 16, 16A, 16B and 16C.

A large number of ionic charges can be generated on the interelectrode surface of the dielectric 22 by either permanently imbedding predetermined minute sized (smaller than 200 mesh) ionic materials, such as glass, $BaSO_4$, and other insoluble, electronically insulating salts on and/or within the interelectrode surface of the dielectric 22 (see FIGS. 5 and 17) in an alternating negative/positive charged ions fashion in order to increase surface ionic conductivity; and/or by reacting the interelectrode surface of the dielectric 22 with an appropriate chemical, an etchant, in order to chemically bind a plurality of negative charged ions thereon (see FIGS. 4 and 16) in order to increase surface ionic conductivity. The particular etchant used depends on the dielectric. As was previously mentioned, suitable etchants for phenolic resin have been determined to be KOH, a mixture of KOH and $H_2O_2$ and, for polystyrene, a mixture of $H_2O_2$ and $H_2SO_4$. Other etchants will be presented below. When predetermined minute sized ionic materials are permanently imbedded on and/or within the interelectrode surface of the dielectric 22 to define the ionically conductive surface 23, the ionically conductive surface 23 per se must be electrostatically neutral; that is, it must have the same number of positive charges as negative charges and vice versa. Since this dielectric material 22 exists dry to start, it is likely that the total negative charges and the total positive charges are present within the solid dielectric surface 22, as illustrated in the drawings, especially FIG. 5. The means for imbedding may be any suitable means such as by pressure or driving the ionic materials into the interelectrode surface of the dielectric 22. When the ionically charged surface is produced by chemical etching one type of charge (+ or −) is permanently fixed to the surface while the opposite charge (− or +) is electrostatically held to the surface.

The data in following Table I are ohmic interelectrode resistances (reference to working electrode 16) in a 15% brine in Crude B crude mixture for the two corrosion probes (FIGS. 6, 7 and 11, and FIGS. 2 and 3) having a phenolic resin dielectric 22, before and after immersion in various etchants:

TABLE I

Effect of Etchants on Interelectrode Resistance in Crude B, 15% Brine, 760 psig. $CO_2$, 180° F., for Phenolic Resin Dielectric Probe (Probe Configuration FIGS. 6, 7 & 11 and FIGS. 2 & 3, after Etchant Treatment Probe De-scaled in 1/1 HCL at 60° C.)

| Etchant Treatment | Interelectrode Resistance, Megohms | |
|---|---|---|
| | FIGS. 6, 7 & 11 Probe | FIGS. 2 & 3, Parallel Electrode Probe |
| None | >5 | 0.05–1.1 |
| 10 M KOH, 80° C.* (60 min) | 1.9 | |
| 10 M KOH, 80° C.* (2 hr) | 0.3–0.64 | 0.003 |
| 1/1 HCl, 60° C. (1 min) | >5 | |
| Conc. $H_2SO_4$, 84° C. (20 min) | >5 | |
| $H_2SO_4/H_2O_2$, 75° C. (2 min) | >5 | |
| NaCl/16% HCl, 60° C. (2 min) | >5 | |

*Electrodes distorted at temperatures above 95° C.

Table I illustrates that the ohmic interelectrode resistances for the corrosion probe 12 in FIGS. 6, 7 and 11 measured under the indicated experimental conditions were in excess of 55 megohms. The corrosion probe 12 of FIGS. 2 and 3 produces a lower resistance which was due in part to the geometrical arrangement of the counter electrodes 20. Soaking in the 10M KOH etchant at 80° C. for 2 hours substantially lowered the interelectrode resistance for both corrosion probes 12. Higher temperatures (above 95° C.) destroyed the electrodes 16, 18 and 20 of the corrosion probes 12, and shorter soaking time did not provide for persistent ionic conductive activity in order to lower the interelectrode resistance.

The data in following Table II are ohmic interelectrode resistance (reference to working electrode 16) in a 15% brine in Crude B crude mixture for the two corrosion probes (FIGS. 24 and 25, and FIGS. 20 and 21) having a phenolic resin dielectric 22, before and after immersion in various etchants:

TABLE II

Effect of Etchants on Interelectrode Resistance in Crude B, 15% Brine, 760 psig. $CO_2$, 180° F., for Phenolic Resin Dielectric Probe (Probe Configuration FIGS. 24 & 25 and FIGS. 20 & 21, after Etchant Treatment Probe De-scaled in 1/1 HCL at 60° C.)

| Etchant Treatment | Interelectrode Resistance, Megohms | |
|---|---|---|
| | FIGS. 24, & 25 Probe | FIGS. 20, & 21 Probe |
| None | >5 | >5 |
| 10 M KOH, 80° C.* (60 min) | 1.9 | 1.9 |
| 10 M KOH, 80° C.* (2 hr) | 0.3–0.64 | 0.3–0.64 |
| 1/1 HCl (1 mn) | >5 | >5 |
| Conc. $H_2SO_4$ (20 min) | >5 | >5 |
| $H_2SO_4/H_2O_2$, 75° C. (2 min) | >5 | >5 |
| NaCl/16% HCl, (2 min) | >5 | >5 |

*Electrode distorted at temperatures above 95° C.

The foregoing Table II illustrates that the ohmic interelectrode resistances for the corrosion probe 12 in FIGS. 24 and 25 and FIGS. 20 and 21 measured under the indicated experimental conditions were in excess of 5 megohms. Soaking in the 10M KOH etchant at 80° C. for 2 hours substantially lowered the interelectrode resistance of the dielectric surface 22 between electrodes 16 and 18 for both corrosion probes 12. As was previously seen in Table I, higher temperatures destroyed the electrodes of the corrosion probes 12, and shorter soaking time did not provide for persistent ionic conductive activity in order to lower the interelectrode resistance.

Table III below lists ohmic interelectrode resistances (reference to working electrode 16) in a 40% brine in Crude B crude mixture for the corrosion probe 12 depicted in FIGS. 6, 7 and 11, and/or for the corrosion probe 12 depicted in FIGS. 24 and 25, with a polystyrene dielectric 22 before and after treatment with various etchants, and shows that the oxidative sulfonation decreased interelectrode resistance.

TABLE III

Effect of Etchants on Interelectrode Resistance in Crude B, 15% Brine, 760 psig. $CO_2$, 180° F., for Polystyrene Dielectric Probe (Probe Configuration FIGS. 6, 7 & 11 and FIGS. 24 & 25, after Etchant Treatment Probe De-scaled in 1/1 HCL at 60° C.)

| Etchant Treatment | Interelectrode Resistance, Megohms FIGS. 6, 7 & 11 and/or FIGS. 24 & 25 |
|---|---|
| None, 80° C. | >5 |
| 10 M KOH, 80° C. (2 hr) | >5 |
| 1/1 $H_2SO_4$, 80° C. (90 min) | >5 |
| $H_2SO_4/15\%$ $H_2O_2$, 25° C. (2 min) | 0.2 |

After the embodiments of the corrosion probes 12 have been prepared with an ionically conductive surface 23 in the previously mentioned appropriate places, the resistance between the working electrode 16 and the reference electrode 18 must be determined for the embodiment of the corrosion probe 12 in FIGS. 2-11. Also to be determined, not only for the embodiment of the corrosion probe 12 in FIGS. 2-11 but for all embodiments of the corrosion probe 12 of this invention, is the difference in potential between a reference electrode 18 (or any electrode functioning as a reference electrode 18 during the sequential measurement of the corrosion rates upon more than one working electrode 16 of different metals (such as working electrodes 16C and/or 16B in FIG. 31)) and an area in a surrounding corrosive liquid environment in general microscopic proximity thereto (about $10^{-6}$ cm or less).

To determine the resistance between the working electrode 16 and the reference electrode 18 for the embodiment of the corrosion probe 12 FIGS. 2-11, a low voltage alternating current at high frequency (e.g., 0.4V at 1000 Hz) is applied to the particular working electrode 16. This and the particular reference electrode 18 are also made one arm of a four arm bridge circuit, identical in concept to a standard Wheatstone Bridge. The resistances of two of the other three arms are fixed. The resistance of the third arm is adjusted until the current passing across the bridge is a minimum. The value for this adjusted resistance is directly proportional to the unknown resistance between the working electrode 16 and the reference electrode 18. The proportionality constant is provided by the manufacturer of the bridge and/or can be determined by direct calibration with known resistances in place of the electrochemical probe.

If the value for this adjusted resistance is multiplied by the proportionality constant, the resistance between the working electrode 16 and the reference electrode 18 is determined or found for the embodiment of the corrosion probe 12 in FIGS. 2-11.

The difference in potential between a reference electrode 18, or any electrode (e.g. working electrodes 16C and/or 16B in FIG. 31) functioning as a reference electrode 18 during sequential measurements of corrosion rates upon more than one working electrode of diverse metals, and an area in a surrounding corrosive liquid environment in general microscopic proximity thereto (about $10^{-6}$ cm or less) is take as that difference in potential measured between the particular electrode that is the working electrode 16 and the particular reference electrode functioning as a reference electrode 18 when no current is flowing from the particular electrode that is the working electrode 16 to the particular counter electrode 20. Stated alternatively, it is the difference in potential measured when no current is flowing into or out of the particular electrode that is the working electrode 16. This reduces the corrosion rate measurement to the determination of the overvoltage necessary to perform the corrosion rate measurement. More specifically, this reduces the corrosion rate measurement to the additional voltage necessary to pass current in order to perform the corrosion rate measurement. It is to be understood that the difference in potential between a reference electrode 18 and area in a surrounding corrosive liquid environment in general microscopic proximity thereto (about $10^{-6}$ cm or less), although not known with respect to a standard reference electrode (such as a calomel electrode), remains essentially constant during the period of time (e.g. about 10 seconds) when a single current density/overpotential measurement is being obtained for each particular electrode that is the working electrode as will also be explained hereafter.

In operation of the embodiment of the corrosion probe 12 of FIGS. 2-11, corrosion probe 12 of FIGS. 2-11 is subsequently inserted into and attached onto the pipe 14 or autoclave 15 containing the corrosive liquid environment 7, which as was previously mentioned, is one of the prepared brine/oil mixtures and is the corrosive liquid environment in which the difference in potential between the reference electrode and an area in a surrounding corrosive liquid environment in general microscopic proximity thereto was determined.

A known applied current (e.g. in amps) or current density [i.e. current (e.g. amps) per unit area (e.g. sq. inches) of working electrode 16], or a known difference in potential, is transmitted or applied to the probe 12 by device 39. As was previously mentioned, this is preferably accomplished through the use of the potentiostat 40 and the signal generator 42. The known current or current density, or the known difference in potential, is dialed into the signal generator 42 which transmits or applies the same to the potentiostat 40. If a current is applied and transmitted to the probe 12 instead of current density, an adjustment has to be made for the area of the working electrode 18 in the final calculation of corrosion rate (e.g. in units of mils per year) which is explained below. In describing the operation of the embodiment of the corrosion probe 12 of FIGS. 2-11 and all other embodiments of the corrosion probe 12 of this invention, a current density will be applied and transmitted, or measured (e.g. with meter 48), instead of a current.

If a known applied current density is dialed into the signal generator 42, the potentiostat 40 transmits this current density as direct current through the depending conductor 34 including the variable resistor 46, through the working electrode 16, over the ionically conductive dielectric surface 23 between the working electrode 16 and the counter electrode 20 and through the counter electrode 20 and back to the potentiostat 40 through depending conductor 38. For this embodiment of the corrosion probe 12, it is assumed that the ohmic resistance across the surface of the reference electrode end 26 is negligible compared to that across the ionic conductive surface 23 of the dielectric 22. The variable resistor 46 may be any suitable value (e.g. 0.1 meg ohm to 1.5 meg ohm). The resistor 46 assists in measuring current, but is not necessary when potentiostat 40 is used. The electromotive force between the working electrode 16 and the reference electrode 18 is measured with the voltmeter 50. From the known applied current density and the previously determined resistance between the working electrode 16 and the reference electrode 18, an electromotive force is found by multiplying the applied current density by the resistance. This electromotive force represents the difference in potential between an area in the corrosive liquid environment in general microscopic proximity to the working electrode 16 (about $10^{-6}$ cm or less) and an area in the corrosive liquid environment in general microscopic proximity to the 25 reference electrode 18 (about $10^{-6}$ cm or less again). The overpotential between the working electrode 16 and an area in the corrosive liquid environment in general microscopic proximity thereto (about $10^{-6}$ cm or less) is subsequently calculated by subtracting from the electromotive force read by the voltmeter 50, the electromotive force found by multiplying the current density by the known resistance between the working electrode 16 and the reference electrode 18, and the predetermined known difference in potential between the reference electrode 18 and the area in the corrosive liquid environment in general microscopic proximity thereto.

The corrosion current on the working electrode 16 of the corrosion probe 12 in FIGS. 2-11 can now be calculated from the Stern-Geary equation:

$$IA = IC[10^{\frac{-P}{BC}} - 10^{\frac{P}{BA}}]$$

where IA is the known applied current density; IC is the corrosion rate expressed as current density; BA and BC are the anodic and cathodic Tafel (or "beta") constants, respectively; and P is the known (measured) overpotential. The equation is applicable to any corroding system with one oxidation process (e.g. metal dissolution) and one reduction process. The Stern-Geary equation describes the behavior of activation controlled corrosion (BA and BC values usually between 30 and 200 mv), diffusion controlled corrosion (BC=∞), or the corrosion of metals in the passive state (BA=∞). The units of the two Tafel constants are to be the same units as the unit which is used for the Overpotential, and is customarily mv.

If only one of the two Tafel constants is known, or one is not known with sufficient accuracy, a second known applied current density is dialed into the signal generator 42 to repeat the process again to obtain a second overpotential. With two known current densities and two known overpotentials for each applied current density, two Stern-Geary equations may be solved simultaneously to obtain the one unknown Tafel constant and the corrosion rate expressed as current density.

Likewise, if two Tafel constants are not known, or not known with sufficient accuracy, a second and subsequently a third known applied current density is dialed into the signal generator 42 to repeat the entire process for each dialed in applied current density to obtain a second and a third overpotential. With three known applied current densities and three known overpotentials for each applied current density, three Stern-Geary ecuations may be solved simultaneously to obtain the two Tafel constants and the corrosion rate expressed as current density.

Calculating corrosion rates from electrochemical data is difficult due to the form of the Stern-Geary equation which can be solved easily by numerical methods. Because of the iterative nature of numerical methods, such analyses are most conveniently performed with a computer. Large mainframe computer systems typically contain programs and/or subroutine libraries capable of numerically solving the Stern-Geary equation.

The corrosion rate is expressed as current density and is a measure of relative corrosion rate, but if desired it can be converted to corrosion rate units by an appropriate conversion factor (microamp/cm$^2$)× factor=mils per year. The factors are listed below for various metals.

| Metal | Factor |
| --- | --- |
| Brass | 0.47 |
| Stainless Steel (304) | 0.43 |
| Hastelloy C | 0.39 |
| Aluminum (AA 7075) | 0.52 |
| Copper | 0.46 |
| Iron (or N80 or Low alloy steel) | 0.46 |
| Nickel | 0.42 |

Continuing to reference the embodiment of the corrosion probe 12 in FIGS. 2-11, if a known difference in potential is dialed into the signal generator 42, the potentiostat 40 applies the difference in potential between the depending conductor 34 and the depending conductor 36. As was previously indicated, depending conductor 34 is connected to working electrode 16 and depending conductor 36 is connected to reference electrode 18; thus the difference in potential is being applied between working electrode 16 and reference electrode 18. As a result of this difference in potential, current density as direct current is being conducted through the conductor 34 including the variable resistor 46, through the working electrode 16, over the ionically conductive dielectric surface 23 between the working electrode 16 and the counter electrode 20, and through the counter electrode 16 and back to the potentiostat 40 through the conductor 38. This current density between the working electrode 16 and counter electrode 20 is measured by the meter 48/resistor 46. From the measured current density and the previously determined resistance between the working electrode 16 and the reference electrode 18, an electromotive force is found by multiplying the measured current density by the resistance, and this electromotive force represents the difference in potential between an area in the corrosive liquid environment in general microscopic proximity to the working electrode 16 (about $10^{-6}$ cm or less) and an area in the corrosive liquid environment in general microscopic proximity to the reference electrode 18 (about $10^{-6}$ cm or less again). The overpotential between the working electrode 16 and an area in the corrosive liquid environment in general microscopic proximity thereto (about $10^{-6}$ cm or less) is subsequently calculated by subtracting from the known difference in potential that was dialed into the signal generator 42, the electromotive force found by multiplying the measured current density by the known resistance between the working electrode 16 and the reference electrode 18 and the predetermined known difference in potential between the reference electrode 18 and the area in the corrosive liquid environment in general microscopic proximity thereto.

As was the case when a known current density was signaled to the potentiostat 40 by the signal generator 42, the corrosion rate (expressed as current density) on the working electrode 16 of the corrosion probe 12 in FIGS. 2-11 can now be calculated from the Stern-Geary equation. Again, if only one of the two Tafel constants is known, or one is not known with sufficient accuracy, a second known difference in potential is dialed into the signal generator 42 to repeat the process again to obtain a second overpotential. With two known measured current densities and two known overpotentials for each applied difference in potential, two Stern-Geary equations may be solved simultaneously to obtain the one unknown Tafel constant and the corrosion rate expressed as current density. Likewise again, if two Tafel constants in the Stern-Geary equation are not known or not known with sufficient accuracy, a second and subsequently a third known difference in potential is dialed into the signal generator 42 to repeat the entire process again for each dialed-in known difference in potential to obtain a second and a third overpotential. With the three known measured current densities and the three known overpotentials for each applied difference in potential, three Stern-Geary equations may be solved simultaneously to obtain the two Tafel constants and the corrosion rate expressed as current density. This corrosion rate, as was the situation for the known applied current densities that were signaled to the potentiostat 40 by the signal generator 42, is a measure of the relative corrosion rate and can be converted to common units of corrosion rate by one of the previously mentioned conversion factors, depending on the type of metal that comprises the working electrode 16.

In operation of the embodiment of the corrosion probe 12 of FIGS. 12-27, corrosion probe 12 of FIGS. 12-27 is subsequently inserted into and attached by fitting 2 onto the pipe 14 or autoclave 15 containing the corrosive liquid environment 7, which as was previously mentioned, is one of the prepared brine/oil mixtures, and is the corrosive liquid environment in which the difference in potential between the reference electrode and an area in a surrounding corrosive liquid environment in general microscopic proximity thereto was determined.

A known applied current density, or a known difference in potential, is transmitted or applied respectively to the probe 12 by device 39. As was previously mentioned, this is preferably accomplished through the use of the potentiostat 40 and the signal generator 42. The known current density, or the known difference in potential, is dialed into the signal generator 42 which transmits or applied respectively the same to the potentiostat 40.

If a known applied current density is dialed into the signal generator 42, the potentiostat 40 transmits this current density as direct current through the depending conductor 34 including the variable resistor 46, through the working electrode 16, through the corrosive liquid environment, and through the counter electrode 20 (or through the conductive means) and back to the potentiostat 40 through the depending conductor 38.

For the embodiment of the corrosion probe 12 in FIGS. 2-11, it was assumed that the ohmic resistance across the surface of the reference electrode end 26 in the corrosion probe 12 of FIGS. 2-11 is negligible compared to that across the ionic conductive surface 23 of the dielectric 22. However, the ohmic resistance across the surface of the reference electrode end 26 does effect the current flow, and the embodiment of the corrosion probe 12 in FIGS. 12-27 overcomes this problem since the current flows through the corrosive liquid environment and not over the surface of the reference electrode end 26.

The variable resistor 46 may be any suitable value (e.g., 0.1 megohm to 1 megohm ) as was previously mentioned. The resistor 46 assists in measuring current, but is not necessary when potentiostat 40 is used. The electromotive force between the reference electrode 18 and the working electrode 16 is measured with the voltmeter 50.

For the embodiment of the corrosion probe 12 in FIGS. 2-11, from the known applied current density and the previously determined resistance between the working electrode 16 and the reference electrode 18, an electromotive force is found by multiplying the applied current density by the resistance. This electromotive force represents the difference in potential between an area in the corrosive liquid environment in general microscopic proximity to the working electrode 16 (about $10^{-6}$ cm or less) and an area in the corrosive liquid environment in general microscopic proximity to the reference electrode 18 (about $10^{-6}$ cm or less again). This step, along with determining the resistance between the reference electrode 18 and the working electrode 16, may now be omitted in the embodiment of the corrosion probe 12 in FIGS. 12-27.

The overpotential between the working electrode 16 and an area in the corrosive liquid environment in general microscopic proximity thereto (about $10^{-6}$ cm or less) is subsequently calculated by subtracting from the electromotive force read by the voltmeter 50, the predetermined known difference in potential between the reference electrode 18 and the area in the corrosive liquid environment in general microscopic proximity thereto.

The corrosion current on the working electrode 16 of the corrosion probe 12 in FIGS. 12-27 can now be calculated from the Stern-Geary equation:

$$I_A = I_C [10^{\frac{-P}{BC}} - 10^{\frac{P}{BA}}]$$

where $I_A$ is the known or measured applied current density; $I_C$ is the corrosion rate expressed as current density; BA and BC are the anodic and cathodic Tafel (or "beta") constants respectively; and P is the known or measured overpotential. As was previously mentioned, the equation is applicable to any corroding system with one oxidation process (e.g., metal dissolution) and one reduction process; and describes the behavior of activation controlled corrosion (BA and BC values usually between 30 and 200 mv), diffusion controlled corrosion (BC=∞), or the corrosion of metals in the passive state (BA=∞).

As was seen for the embodiment of the corrosion probe 12 in FIGS. 2-11, if any one of the two Tafel constants is known, or one is not known with sufficient accuracy, a second known applied current density is dialed into the signal generator 42 to repeat the process again to obtain a second overpotential. With two known current densities and two known overpotentials for each applied current density, two Stern-Geary equations may be solved simultaneously to obtain the one known Tafel constant and the corrosion rate expressed as current density on the metal of the working electrode 16 in the corrosion probe 12 of FIGS. 12-27.

Likewise, if two Tafel constants are not known, or not known with sufficient accuracy, a second and subsequently a third known applied current density is dialed into the signal generator 42 to repeat the entire process for each dialed in applied current density to obtain a second and a third overpotential. With three known applied current densities and three known overpotentials for each applied current density, three Stern-Geary equations may be solved simultaneously to obtain the two Tafel constants and the corrosion rate expressed as current density on the metal of the working electrode 16 in the corrosion probe 12 of FIGS. 12-27.

As was previously mentioned for the embodiment of the corrosion probe 12 in FIGS. 2-11, the corrosion rate is expressed as current density and is a measure of relative corrosion rate, but if desired, it can be converted to corrosion rate units by an appropriate conversion factor (microamp/cm²)× factor=mils per year. The factors for various metals were previously listed.

Continuing to reference the embodiment of the corrosion probe 12 in FIGS. 12-27, if a known difference in potential is dialed into the signal generator 42, the potentiostat 40 applies the difference in potential between the depending conductor 34 which is attached to the working electrode 16 and the depending conductor 36 which is attached to the reference electrode 18. As a result of this difference in potential between the working electrode 16 and the reference electrode 18, a current density (as direct current) is being conducted through the conductor 34 including the variable resistor 46, through the working electrode 16, and through the counter electrode 20 or the current conductive means (e.g., the side of the autoclave 15), and back to the potentiostat 40 through the conductor 38. In the embodiment of the corrosion probe 12 in FIGS. 2-11, the reference electrode 18 is positioned between the working electrode 16 and the counter electrode 20 and all dielectric surfaces 22 between the working and counter electrodes 16 and 20 respectively, are ionically conductive dielectric surfaces 23 in order to conduct the current density from the working electrode 16, over the ionically conductive dielectric surfaces 23 between the working electrode 16 and counter electrode 20, including the surface of the reference electrode end 26, to the counter electrode 20. In a preferred embodiment of the corrosion probe 12 in FIGS. 12-27, there is no ionically conductive dielectric surface 23 between the working electrode 16 and the counter electrode 20. The current density cannot be conducted over any ionically conductive dielectric surface 23 between the working electrode 16 and the counter electrode 20. With embodiment of the corrosion probe 12 in FIGS. 12-27, the current density between the working electrode 16 and the counter electrode 20 (or the current conductive means) is being conducted through the corrosive liquid environment, as was previously mentioned, and is measured by the meter 48. This measured current density is IA in the Stern-Geary equation.

The overpotential between the working electrode 16 and an area in the corrosive liquid environment in general microscopic proximity thereto (about $10^{-6}$ cm or less) is subsequently calculated by subtracting from the known difference in potential that was dialed into the signal generator 42 as measured by voltmeter 50, the predetermined known difference in potential between the reference electrode 18 and the area in the corrosive liquid environment in general microscopic proximity thereto. This calculated overpotential is P in the Stern-Geary equation.

As was the case when a known current density was signaled to the potentiostat 40 by the signal generator 42, with P (the overpotential), $I_A$ (the measured current density) and two known Tafel constants, the corrosion rate (expressed as current density) on the working electrode 16 of the corrosion probe 12 in FIGS. 12-27 can now be calculated from the Stern-Geary equation.

Again, if only one of the two Tafel constants is known, or one is not known with sufficient accuracy, a second known difference in potential is dialed into the signal generator 42 to repeat the process again to obtain a second overpotential. With two known measured current densities and two known overpotentials for each applied difference in potential, two Stern-Geary equations may be solved simultaneously to obtain the one unknown Tafel constant with the corrosion rate expressed as current density on the metal of the working electrode 16 in the corrosion probe 12 of FIGS. 12-27.

Likewise again, if two Tafel constants in the Stern-Geary equation are not known, or not known with sufficient accuracy, a second and subsequently a third known difference in potential is dialed into the signal generator 42 to repeat the entire process again for each dialed-in known difference in potential to obtain a second and a third overpotential. With the three known measured current densities and the three known overpotentials for each applied difference in potential, three Stern-Geary equations may be solved simultaneously to obtain the two Tafel constants and the corrosion rate expressed as current density. This corrosion rate, as was the situation for the known applied current densities that were signaled to the potentiostat 40 by the signal generator 42, is a measure of the relative corrosion rate and can be converted to common units of corrosion rate by one of the previously mentioned conversion factors, depending on the type of metal that comprises the working electrode 16.

It is important to understand that for the preferred embodiment of the corrosion probe 12 in FIGS. 22-27, if the counter electrode 20 and the reference electrode 18 are interchanged with each other and the ionically conductive dielectric surface 23 is between the working electrode 16 and the outside reference electrode 18, the corrosion probe 12 would achieve the same results and generally function identically with the preferred embodiment of the corrosion probe 12 having the reference electrode 18 concentrically positioned with respect to the working electrode 16 and the counter electrode 20. The current density between the working electrode 16 and the counter electrode 20 could still be conducted through the corrosive liquid environment, and the dialed-in difference in potential would be transmitted through the working electrode 16, over the ionically conductive dielectric surface 23 between the working electrode 16 and the outside positioned reference electrode 18, and through the reference electrode 18. For the embodiment of the corrosion probe 12 in FIGS. 22-27, it is important to have the working electrode 16 between the reference and counter electrodes 18 and 20, respectively, because by positioning the working electrode 16 as such, the resistance between the working electrode 16 and the reference electrode 18 does not have to be determined, the dielectric surface 22 between the working electrode 16 and the counter electrode 20 does not have to be made ionically conductive, and the current density no longer need be conducted over any ionically conductive dielectric surface 23 between the working electrode 16 and the counter electrode 20.

In operation of the embodiment of the corrosion probe 12 of FIGS. 28 and 29, for simultaneous measurement of the corrosion rates upon each of the diverse metals of working electrodes 16A, 16B and 16C, the corrosion probe 12 of FIGS. 28 and 29, is inserted into and attached on the pipe 14 or autoclave 15 containing the corrosive liquid environment (i.e. one of the brine/oil mixtures) which is the corrosive liquid environment where the difference in potential between the reference electrode and an area in a surrounding corrosive liquid environment in general microscopic proximity thereto was determined. A first, a second, and a third potentiostat 40, 40 and 40, respectively, are employed along with a first, a second, and a third signal generator 42, 42, and 42, respectively, to transmit to the corrosion probe 12 of FIGS. 28 and 29 three known applied current densities or three known differences in potential.

A first potentiostat 40 connects electrically to a first set of depending conductors consisting of depending conductors 36, 34A and 38 and extending respectively from the center reference electrode 18, from the working electrode 16A, and from the counter electrode 20 that is located between working electrodes 16A and 16B. A second potentiostat 40 connects electrically to a second set of depending conductors consisting of depending conductors 38, 34B and 36 and extending respectively from the counter electrode 20 that is situated between working electrodes 16A and 16B, from the working electrode 16B, and from the reference electrode 18 that has been positioned between working electrodes 16B and 16C. A third potentiostat 40 connects electrically to a third set of depending conductors comprising depending conductors 36, 34C and 38 and extending respectively from the reference electrode 1 that is located between working electrodes 16B and 16C, from the working electrode 16C, and from the outer counter electrode 20. The first, the second and the third signal generators 42, 42 and 42 would respectively engage electrically the first, the second, and the third potentiostats 40, 40 and 40 for instructing or signaling a predetermined known amperage or known difference in potential to the first, the second, and the third potentiostat 40, 40 and 40 respectively.

A first known applied current density may be dialed into the first signal generator 42 wherein it is transmitted to the first potentiostat 40. Simultaneously, a second known applied current density and a third known applied current density may be dialed into the second and the third signal generator 42 and 42, respectively, wherein each respective generator 42 transmits its dialed-in current density to its respective potentiostat 40 (i.e. either the second or the third potentiostat).

The first potentiostat 40 transmits the first current density as direct current through the depending conductor 34A, through the working electrode 16A, through the corrosive liquid environment, and through the counter electrode 20 that is located between working electrodes 16A and 16B, and back to the first potentiostat 40 through the depending conductor 38 connected to the counter electrode 20 that is located between working electrodes 16A and 16B. A first electromotive force between the center reference electrode 18 and the working electrode 16A is measured with the voltmeter 50, which connects from depending conductor 34A to the conductor 36 attaching to the center reference electrode 18.

The second potentiostat 40 transmits the second current density as direct current through the depending conductor 34B, through the working electrode 16B, through the corrosive liquid environment, and through the counter electrode 20 that is positioned between working electrodes 16A and 16B, and back to the second potentiostat 40 through the depending conductor 38 connected to the counter electrode 20 that is positioned between working electrodes 16A and 16B. A second electromotive force between the reference electrode 18 (located between working electrodes 16B and 16C) and working electrode 16B is measured with the voltmeter 50, which connects from depending conductor 34B to the conductor 36 attaching to the reference electrode 18 that is positioned between working electrodes 16B and 16C.

The third potentiostat 40 transmits the third current density as direct current through the depending conductors 34C, through the working electrode 16C, through the corrosive liquid environment, and through the outer counter electrode 20, and back to the third potentiostat 40 through the depending conductor 38 that connects to the outer counter electrode 20. A third electromotive force between the reference electrode 18

(located between working electrodes 16B and 16C) and working electrode 16C is measured with the voltmeter 50, which connects from depending conductor 34C to the conductor 36 attaching to the reference electrode 18 that is positioned between working electrodes 16B and 16C.

The overpotential between the working electrode 16A and an area in the corrosive liquid environment in general microscopic proximity thereto (about $10^{-6}$ cm or less) is subsequently calculated by subtracting from the first electromotive force read by the voltmeter 50, the predetermined known difference in potential between the center reference electrode 18 and the area in the corrosive liquid environment in general microscopic proximity thereto. Similarly, the second overpotential between the working electrode 16B and an area in the corrosive liquid environment in general microscopic proximity thereto (about $10^{-6}$ or less) is subsequently calculated by subtracting from the second electromotive force read by the voltmeter 50, the predetermined known difference in potential between the reference electrode 18 (situated between working electrodes 16B and 16C) and the area in the corrosive liquid environment in general microscopic proximity thereto. Likewise, the third overpotential between the working electrode 16C and an area in the corrosive liquid environment in 20 general microscopic proximity thereto (about $10^{-6}$ cm or less) is also subsequently calculated by subtracting from the third electromotive force read by the voltmeter 50, the predetermined known difference in potential between the reference electrode 18 (situated between working electrodes 16B and 16C) and the area in the corrosive liquid environment in general microscopic proximity thereto.

The corrosion current simultaneously made on each of the metals of the working electrodes 16A, 16B, and 16C for the corrosion probe 12 in FIGS. 28 and 29 may now be calculated from the Stern-Geary equation in accordance with the procedure previously set forth for the embodiment of the corrosion probe 12 in FIGS. 2-11 and FIGS. 12-27. If only one of the two Tafel constants is known for any of the working electrodes 16A, 16B, and 16C, then another applied current density is dialed into each of the particular signal generators 42 whose electrically attached potentiostat 40 is electrically engaged to the particular working electrode (i.e. 16A, or 16B or 16C) having only one of the two Tafel constants known to repeat the process again to obtain another overpotential for any of the working electrodes 16A, 16B and 16C having only one of the two Tafel constants known. With two known current densities and two known overpotentials for each applied current density, two Stern-Geary equations may be solved simultaneously to obtain the one unknown Tafel constant and the corrosion rate expressed as current density on the metal of any of the working electrodes 16A, 16B and 16C having only one of the two Tafel constants known. The procedure may be repeated for any of the working electrodes 16A, 16B and 16C having two Tafel constants unknown. With three known applied current densities and three known overpotentials for each applied current density, three Stern-Geary equations may be solved simultaneously to obtain the two Tafel constants and the corrosion rate expressed as current density on the metal of any of the working electrodes 16A, 16B and 16C having two Tafel constants unknown.

Continuing to reference the embodiment of the corrosion probe 12 in FIGS. 28 and 29, for applying to the corrosion probe 12 of FIGS. 28 and 29 three known difference in potentials (instead of three known applied current densities) for simultaneous measurement of the corrosion rates upon each of the diverse metals of working electrodes 16A, 16B and 16C, a first known difference in potential may be dialed into the first signal generator 42 wherein it is transmitted to the first potentiostat 40. Simultaneously, a second known difference in potential and a third known difference in potential may be dialed into the second and the third signal generator 42 and 42 respectively wherein each generator 42 transmits and/or applies its dialed-in difference in potential to its respective potentiostat 40 (i.e. either the second or the third potentiostat).

The first potentiostat 40 applies the first difference in potential between the depending conductor 4A connected to the working electrode 16A and the depending conductor 36A attached to the center reference electrode 18. As a result of this first difference in potential, a first current density (as direct current) is being conducted through the conductor 34A including the variable resistor 46, through the working electrode 16A, and through the counter electrode 20 that is located between the working electrodes 16A and 16B, an back to the first potentiostat 40 through the conductor 38 secured to the counter electrode 20 that is positioned between the working electrodes 16A and 16B. The first current density is measured by a meter 48 that is electrically engaged to and within the conductor 34A.

The second potentiostat 40 applies the second difference in potential between the depending conductor 34B connected to the working electrode 16B and the depending conductor 36 secured to the reference electrode 18 that is positioned between working electrodes 16B and 16C. As a result of this second difference in potential, a second current density (as direct current) is being conducted through the conductor 34B including the variable resistor 46, through the working electrode 16B, and through the counter electrode 20 that is positioned between the working electrodes 16A and 16B, and back to the second potentiostat 40 through the conductor 38 secured to the counter electrode 20 that is positioned between the working electrodes 16A and 16B. The second current density is measured by another meter 48 that is electrically engaged to and within the conductor 34B.

The third potentiostat 40 transmits and/or applies the third difference in potential between the depending conductor 34C connected to the working electrode 16C and the depending conductor 36 secured to the reference electrode 18 that is positioned between working electrodes 16B and 16C. As a result of this third difference in potential, a third current density (as direct current) is being conducted through the conductor 34C including the variable resistor 46, through the working electrode 16C, and through the outer counter electrode 20 and back to the third potentiostat 40 through the conductor 38 that is connected to the outer counter electrode 20. The third current density is measured by yet another meter 48 that is electrically engaged to and within the conductor 34C.

The overpotential between the working electrode 16A and an area in the corrosive liquid environment in general microscopic proximity thereto (about $10^{-6}$ cm or less) is subsequently calculated by subtracting from the first known difference in potential that was dialed into the first signal generator 42 as measured by voltmeter 50 (which connects from depending conductor 34A to the conductor 36 attaching to the counter reference electrode 18), the predetermined known difference in potential between the center reference electrode 18 and the area in the corrosive liquid environment in general microscopic proximity thereto. This calculated overpotential is P for working electrode 16A in the Stern-Geary equation.

Similarly, the overpotential between the working electrode 16B and an area in the corrosive liquid environment in general microscopic proximity thereto (about $10^{-6}$ cm or less) is subsequently calculated by subtracting from the second known difference in potential that was dialed into the second signal generator 42 as measured by voltmeter 50 (which connects from depending conductor 34B to the conductor 36 attaching to the reference electrode 18 that is positioned between working electrodes 16B and 16C), the predetermined known difference in potential between the reference electrode 18 (positioned between working electrodes 16B and 16C) and the area in the corrosive liquid environment in general microscopic proximitythereto. This calculated overpotential is P for working electrode 16B in the Stern-Geary equation.

The overpotential between the working electrode 16C and an area in the corrosive liquid environment in general microscopic proximity thereto (about $10^{-6}$ cm or less) is also subsequently calculated by subtracting from the third known difference in potential that was dialed into the third signal generator 42 as measured by voltmeter 50 (which connects from depending conductor 34C to the conductor 36 attaching to the reference electrode 18 that is positioned between working electrodes 16B and 16C), the predetermined known difference in potential between the reference electrode 18 (positioned between working electrodes 16B and 16C) and the are in the corrosive liquid environment in general microscopic proximity thereto. This calculated overpotential is P for working electrode 16C in the Stern-Geary equation.

As was the case when a known current density was signaled to the potentiostat 40 by the signal generator 42, with P (the overpotential), $I_A$ (the measured current density) and two known Tafel constants, the corrosion rate (expressed as current density) simultaneously made on each of the metals of the working electrode 16A, 16B and 16C for the corrosion probe 12 in FIGS. 28 and 29 can now be calculated from the Stern-Geary equation in accordance with the procedures previously set forth for the embodiment of the corrosion probe 12 in FIGS. 12–27.

Again, if only one of the two Tafel constants is known, or one is not known with sufficient accuracy, for any of the working electrodes 16A, 16B and 16C, then another known difference in potential is dialed into each of the particular signal generators 42 whose electrically attached potentiostat 40 is electrically engaged to the particular working electrode (i.e. 16A or 168 or 16C) having only one of the two Tafel constants known to repeat the process again to obtain another overpotential for any of the working electrodes 16A, 16B and 16C having only one of the two Tafel constants known. With two known measured current densities and two known overpotentials for each applied difference in potential, two Stern-Geary equations may be solved simultaneously to obtain the one unknown Tafel and the corrosion rate expressed as current density on the metal of any of the working electrodes 16A, 16B and 16C having only one of the two Tafel constants known. The procedure may be repeated for any of the working electrodes 16A, 16B or 16C having two Tafel constants unknown. With three known measured current densities and the .known overpotentials for each applied difference in potential, three Stern-Geary equations may be solved simultaneously to obtain the two Tafel constants and the corrosion rate expressed as current density on the metal of any of the working electrodes 16A, 16B, and 16C having two Tafel constants unknown.

In comparing the embodiment of the corrosion probe 12 in FIGS. 32 and 33, with the embodiment of the corrosion probe 12 in FIGS. 28 and 29, all counter electrodes 20 have been interchanged with all reference electrodes 18, and vice versa, and all ionic conductive surfaces 23 are between particular working electrodes 16A, 16B and 16C and particular reference electrodes 18. More specifically, in .the corrosion probe 12 of FIGS. 28 and 29, the center electrode is a reference electrode 18 and the outer electrode is a counter electrode 20, whereas in the corrosion probe 12 of FIGS. 32 and 33, the center electrode is a counter electrode 20 and the outer electrode is a reference electrode 20. Similarly, in the corrosion probe 12 of FIGS. 28 and 29 a counter electrode 20 is positioned between working electrodes 16A and 16B and a reference electrode 18 is positioned between working electrodes 16B and 16C, whereas in the corrosion probe 12 of FIGS. 32 and 33, the electrodes between working electrodes 16A an 16B and between working electrodes 16B and 16C are a reference electrode 18 and a counter electrode 20, respectively. With such an interchange of electrodes and interchange of ionic conductive surfaces 23, the corrosion probe 12 of FIGS. 32 and 33 would achieve the same results and generally function identically with the preferred embodiment of the corrosion probe 12 in FIGS. 28 and 29. The current densities between particular working electrodes 16A, 16B and 16C and particular counter electrodes 20 would still be conducted through the corrosive liquid environment, and the dialed-in difference in potential would still be applied between particular working electrodes 16A, 16B and 16C, and the particular contiguous reference electrodes 18. Corrosion rates (expressed as current density) simultaneously made upon each of the working electrodes 16A, 16B and 16C can be calculated from the Stern-Geary equation with P (the overpotential on any particular working electrode 16A, 16B, or 16C), $I_A$ (the known or measured applied current density through any particular working electrode 16A, 16B or 16C), and two known Tafel constants.

If the corrosion rate upon each of the diverse metals of the working electrodes 16A, 16B and 16C in the corrosion probe 12 in FIGS. 28, 29 and 32 and 33 is to be measured sequentially (rather than simultaneously) with one potentiostat 40 and one signal generator 42, then the single potentiostat 40 is initially connected electrically to a first set of depending conductors, for example: depending conductors 36, 34A and 38 (in FIGS. 28 and 29) extending respectively from the center reference electrode 18, from the working electrode 16A, and from the counter electrode 20 that is positioned between the working electrodes 16A and 16B; or depending conductors 38, 34A and 36 (in FIGS. 32 and 33) extending respectively from the center counter electrode 20, from the working electrode 16A, and from the reference electrode 18 that is positioned between the working electrodes 16A and 16B. After the appropriate signal (i.e. either a known applied current density or a known difference in potential) has been transmitted and/or applied to the particular set of depending conductors by the potentiostat 40, and after the appropriate measurements have been made, the corrosion rates (expressed as current density) upon the working electrode 16A may be calculated from the Stern-Geary equation as previously discussed. After the corrosion rate upon working electrode 16A has been determined, the single potentiostat 40 is subsequently disconnected from the first set of depending conductors and connected electrically to a second set of depending conductors, by way of example only: depending conductors 36, 34C and 38 (in FIGS. 28 and 29) extending respectively from the reference electrode 18 positioned between working electrodes 16B and 16C, from the working electrode 16C, and from the outer counter electrode 20; or depending conductors 36, 34C and 38 (in FIGS. 32 and 33) extending respectively from the outer reference electrode 18, from working electrode 16C, and from the counter electrode 20 that is positioned between the working electrodes 16B and 16C. The appropriate signal is again transmitted and/or applied to the particular set of depending conductors by the potentiostat 40, and the entire procedure is again repeated to find the corrosion rate upon the working electrode 16C from the Stern-Geary equation. The single potentiostat 40 is subsequently disconnected from the second set of depending conductors and connected electrically to a third set of depending conductors to repeat the entire process again to find the corrosion rate upon the working electrode 16B.

In the operation of the embodiment of the corrosion probe 12 of FIG. 31 for sequential measurement of the corrosion rates upon each of the diverse metals of the working electrodes 16A, 16B and 16C, the corrosion probe 12 of FIG. 31 is inserted into and on the pipe 14 or autoclave 15 containing the corrosive liquid environment (i.e. one of the brine/oil mixtures). A single potentiostat 40 and a single signal generator 42 is employed. The potentiostat 40 is connected electrically to a first set of depending conductors consisting of depending conductors 38, 34A, and 34B and extending respectively from counter electrode 20, working electrode 16A whose corrosion rate is to be determined, and working electrode 16B which is functioning as a reference electrode 18. A known current density, or a known difference in potential, is dialed into the signal generator 42 which transmits the same to the potentiostat 40.

If a known applied current density is dialed into the signal generator 42, the potentiostat 40 transmits and/or applies this current density as direct current through the depending conductor 34A (including the variable resistor 46), through the working electrode 16A, through the corrosive liquid environment, and through the counter electrode 20 and back to the potentiostat 40 through the depending conductor 38. The electromotive force between the working electrode 16B (functioning as a reference electrode 18) and the working electrode 16A is measured by the voltmeter 50 which is connected from depending conductor 34B to depending conductor 34A.

The overpotential between the working electrode 16A and an area in the corrosive liquid environment in general microscopic proximity thereto (about $10^{-6}$ cm or less) is subsequently calculated by subtracting from the electromotive force read by the voltmeter 50, the predetermined known difference in potential between the working electrode 16B (functioning as a reference electrode 18) and the area in the corrosive liquid environment in general microscopic proximity thereto. The corrosion current on the working electrode 16A of the corrosion probe 12 in FIG. 31 can now be calculated from the Stern-Geary equation in accordance with the procedure previously set forth.

The potentiostat 40 is disconnected from the first set of depending conductors and is subsequently attached to a second set of depending conductors consisting of depending conductors 38, 34B and 34C extending respectively from counter electrode 20, working electrode 16B whose corrosion rate is to be determined, and working electrode 16C which is functioning as a reference electrode 18.

Another known applied current density is dialed into the signal generator 42, and the potentiostat 40 transmits and/or applies this current density as direct current through the depending conductor 34B (including the variable resistor 46), through the working electrode 16B, through the corrosive liquid environment, and through the counter electrode 20 and back to the potentiostat 40 through the depending conductor 38. The electromotive force between the working electrode 16C (functioning as a reference electrode 18) and the working electrode 16B is measured by the voltmeter 50 which is connected from depending conductor 34C to depending conductor 34B.

The overpotential between the working electrode 16B and an area in the corrosive liquid environment in general microscopic proximity thereto (about $10^{-6}$ cm or less) is subsequently calculated by subtracting from the electromotive force read by the voltmeter 50, the predetermined known difference in potential between the working electrode 16C (functioning as a reference electrode 18) and the area in the corrosive liquid environment in general microscopic proximity thereto. The corrosion current on the working electrode 16B of the corrosion probe 12 in FIG. 31 can now be calculated from the Stern-Geary equation in accordance with the procedure previously setforth.

The potentiostat 40 is disconnected from the second set of depending conductors and is subsequently attached to a third set of depending conductors consisting of depending conductors 38, 34C and 36 extending respectively from counter electrode 20, working electrode 16C whose corrosion rate is to be determined, and the reference electrode 18.

A third known applied current density is dialed into the signal generator 42, and the potentiostat 40 transmits this current density as direct current through the depending conductor 34C (including the variable resistor 46), through the working electrode 16C, through the corrosive liquid environment, and through the counter electrode 20 and back to the potentiostat 40 through the depending conductor 38. The electromotive force between the working electrode 16C and reference electrode 18 is measured by the voltmeter 50 which is connected from depending conductor 34C to depending conductor 36.

The overpotential between the working electrode 16C and an area in the corrosive liquid environment in general microscopic proximity thereto (about $10^{-6}$ cm or less) is subsequently calculated by subtracting from the electromotive force read by the voltmeter 50, the predetermined known difference in potential between the reference electrode 18 and the area in the corrosive liquid environment in general microscopic proximity thereto. The corrosion current on the working electrode 16C can now be calculated from the Stern-Geary equation in accordance with the procedure previously set forth.

Continuing to reference the embodiment of the corrosion probe 12 in FIG. 31, if a known difference in potential is dialed into the signal generator 42, the potentiostat 40 (secured electrically to the first set of depending conductors) applies the difference in potential between the depending conductor 34A secured to the working electrode 16A and the depending conductor 34B secured to the working electrode 16B (which is functioning as a reference electrode 18). As a result of this difference in potential, a current. density (as direct current) is being conducted through the conductor 34A (including the variable resistor 46), through the working electrode 34A, and through the counter electrode 20, and back to the potentiostat 40 through the conductor 38. This current density is measured by the meter 48 that is connected to and/or within conductor 34A.

The overpotential between the working electrode 16A and an area in the corrosive liquid environment in general microscopic proximity thereto (about $10^{-6}$ cm or less) is subsequently calculated by subtracting from the known difference in potential that was dialed into the signal generator 42 as measured by voltmeter 50, the predetermined known difference in potential between the working electrode 16B (which is functioning as a reference electrode 18) and the area in the corrosive liquid environment in general microscopic proximity thereto. This calculated overpotential is P in the Stern-Geary equation.

As was the case when a known current density was signaled to the potentiostat 40 by the signal generator 42, with P (the overpotential), $I_A$ (the measured current density) and two known Tafel constants, the corrosion rate (expressed as current density) on the working electrode 16A of the corrosion probe 12 in FIG. 31. can now be calculated from the Stern-Geary equation.

After the potentiostat 40 has been disconnected from the first set of depending conductors and is connected to the second set of depending conductors, another known difference in potential is dialed into the signal generator 42 and the potentiostat 40 applies the difference in potential between the depending conductor 34B connected to the working electrode 16B and the depending conductor 34C connected to the working electrode 16C (which is functioning as a reference electrode 18). As a result of this difference in potential, a current density (as direct current) is being conducted through the conductor 34B (including the variable resistor 46), through the working electrode 16B, over the ionically conductive dielectric surface between the working electrodes 16B and 16A, through the corrosive liquid environment, and through the counter electrode 20 and back to the potentiostat 40 through the conductor 38. This current density is measured by the meter 48 that is connected to and/or within conductor 34B.

The overpotential between the working electrode 16B and an area in the corrosive liquid environment in general microscopic proximity thereto (about $10^{-6}$ cm or less) is subsequently calculated by subtracting from the known difference in potential that was dialed into the signal generator 42 as measured by voltmeter 50, the predetermined known difference in potential between the working electrode 16C (which is functioning as a reference electrode 18) and the area in the corrosive liquid environment in general microscopic proximity thereto. This calculated overpotential is P in the Stern-Geary equation.

As was the case when a known current density was signaled to the potentiostat 40 by the signal generator 42, with P (the overpotential), $I_A$ (the measured current density) and two known Tafel constants, the corrosion rate (expressed as current density) on the working electrode 16B of the corrosion probe 12 in FIG. 31 can now be calculated from the Stern-Geary equation.

The potentiostat 40 is now disconnected from the second set of depending conductors and is subsequently connected to the third set of depending conductors, and if another known difference in potential is dialed into the signal generator 42, the potentiostat 40 applies this difference in potential between the depending conductor 34C connected to the working electrode 16C, and the depending conductor 36 connected to reference electrode 18, As a result of this difference in potential, a current density (as direct current) is being conducted through the conductor 34C (including the variable resistor 46), through the working electrode 16C over the ionically conductive dielectric surface 23 between the working electrodes 16C and 16B, over the working electrode end 24B and across the ionically conductive dielectric surface 23 between the working electrodes 16B and 16A, through the corrosive liquid environment, and through the counter electrode 20 and back to the potentiostat 40 through the conductor 38. This current density is measured by the meter 48 connected to and/or within conductor 34C.

The overpotential between the working electrode 16C and an area in the corrosive liquid environment in general microscopic proximity thereto (about $10^{-6}$ cm or less) is subsequently calculated by subtracting from the known difference in potential that was dialed into the signal generator 42 as measured by volt-meter 50, the predetermined known difference in potential between the reference electrode 18 and the area in the corrrosive liquid environment in general microscopic proximity thereto. This calculated overpotential is P in the Stern-Geary equation.

As was the case when a known current density was signaled to the potentiostat 40 by the signal generator 42, with P (the overpotential), $I_A$ (the measured current density) and two known Tafel constants, the corrosion rate (expressed as current density) on the working electrode 16C of the corrosion probe 12 in FIG. 31, can now be calculated from the Stern-Geary equation as was previously set forth.

The operation of the embodiment of the corrosion probe 12 in FIG. 30 (with only working electrodes 16A and 16B) for sequential measurement of the corrosion rates upon each of the diverse metals of the working electrodes 16A and 16B is identical with the procedure for operating the corrosion probe 12 of FIG. 31, with the exception that no third or working electrode 16C is involved to determine the corrosion rate upon. Therefore, no third known applied current or third known difference of potential will have to be dialed into the signal generator 42 to obtain the appropriate measurements to calculate the corrosion rate on working electrode 16C from the Stern-Geary equation.

It should be understood that for any of the sequential measurements utilizing the corrosion probe 12 of FIGS. 28–33 to obtain sequentially the corrosion rates upon working electrodes 16A, 16B and 16C, and wherein only one of the two Tafel constants is known for any particular working electrode (i.e. 16A or 16B or 16C), or wherein two Tafel constants are unknown for any particular working electrode 16A or 16B or 16C, then a second or a third applied current density or known difference in potential will have to be dialed into the signal generator 42, for each particular working electrode 16A or 16B or 16C to repeat the process in order to obtain the necessary unknown to solve simultaneously the Stern-Geary equation to determine the corrosion rate upon the particular working electrode(s) 16A and/or 16B and/or 16C having one or both Tafel constants unknown.

It should also be understood that for any of the embodiments of the corrosion probe 12 in FIGS. 28-33, if the corrosion rate upon each of the diverse metals of the working electrodes 16A, 16B (in FIGS. 30 and 31) and 16C (in FIG. 31) is to be measured sequentially with one potentiostat 40 and one signal generator 42, then the period of time between the taking of readings, measurements, and determining the corrosion rate upon the diverse metal of one working electrode 16 (i.e. 16A or 16B or 16C), and the taking of readings, measurements, and determining the corrosion rate upon the diverse metal of another working electrode 16 (i.e. 16A or 16B or 16C) should be as short as possible, preferably less than about one (1) minute. As has been previously mentioned, the period of time is more preferably less than about ten (10) seconds. With such a short period of time, between determining the corrosion rate upon any particular two working electrodes 16(e.g. 16A and 16B), the environment of the corroding working electrodes will not be artificially changed, such as from any excess negative current evolving hydrogen bubbles, which will stir the thin film of aqueous phase on the metal surface of any of the corroding working electrode(s). The stirring action can change the concentrations of the corroding acid. Similarly, excess positive current can artificially thicken the insoluble oxidized metal phase on the metal surface of any of the corroding working electrode(s), and/or excess positive current can artificially generate pits and crevices on the same.

In still yet another embodiment of this invention, the corrosion probe 12 (preferably the embodiment of FIGS. 12-27) with electrodes [i.e. working electrode 16, reference electrode 18, and counter electrode 20 (if employed)] fabricated of an electrochemically inert material, or material whose surface is or has been made electrochemically inert (e.g. black platinum plating), may be used to perform electroanalytical measurements on highly resistive fluids. More specifically, the corrosion probe 12 whose electrodes or electrodes' surfaces are electrochemically inert may be used to measure electrochemically active constituents, components, or materials in a generally nonionic conductive fluid. The measurements may be accomplished on individual batches of the fluids, or on continuously flowing fluids. The corrosion probe 12 would also be of value as a process stream monitor during the synthesis and/or handling of non-conductive fluids.

The electrochemically inert material which is contained within or on the surface of the working electrode 16, the reference electrode 18, and the counter electrode 20 (if utilized) may be any electrochemically inert material which, when exposed to the generally nonionic conductive fluids, is not substantially oxidizable or reducible within the electrical potential range to be employed in the electroanalytical measurements. Preferably, the electrochemically inert material used in the corrosion probe 12 is selected from the group consisting of gold, platinum, graphite, carbon, etc., or mixtures thereof. More preferably, the electrochemically inert material is platinum.

The generally nonionic conductive fluid may be any liquid medium of high ohmic resistance (i.e. a liquid medium essentially devoid of ionic charge carriers). The generally nonionic conductive fluid comprises at least one phase. Suitable one phase generally nonionic conducting fluids have been found to be, by way of example only, pure water, pure tetrahydrofuran (THF), pure acetic acid, etc. Also by way of example only, suitable two phase generally nonionic conductive fluids have been determined to be water and liquid hydrocarbon (e.g. oil) etc. Three phase generally nonionic conductive fluids in which to conduct electroanalytical measurements with the corrosion probe 12 of this invention would be, by way of example only, gas and water and liquid hydrocarbon (e.g. oil), etc.

The generally nonionic conductive fluid may be a mixture of one or more components wherein at least one of the components is electroactive but not necessarily ionically conductive. The entire mixture, as well as its individual components, should be electrically insulating which may be taken as an electrically insulating fluid having a resistance nominally of 2 megohms or more between the working electrode 16 and the counter electrode 20 in FIGS. 22-27 and wherein the separation between the working electrode 16 and the counter electrode 20 not having the ionic conductive surface 23 is nominally 0.025 inches. An electrically insulating fluid may be taken as the inverse of ionically conductive fluids.

The entire mixture may or may not be ionically conductive. Prior art devices (as well as the corrosion probe 12 of this invention) can perform electrochemical measurements in ionically conductive fluids and/or mixtures, but electrochemical measurements in non-ionic conductive fluids and/or mixtures (as measurements on generally nonionic conducting fluids and/or mixtures as defined above may only be performed with the corrosion probe 12 of this invention. Thus, the corrosion probe 12 of this invention, which may be the two electrode embodiment of FIGS. 14 and 15 or the three electrode embodiment of FIGS. 22-27, may be used to measure both qualitatively and quantitatively, electrochemically active component(s) in an electrically insulating mixture comprising at least one electroactive component.

Typical electrically insulating fluids and/or generally nonionically conductive fluids, by way of illustration only, are tetrahydrofuran (THF), 100% acetic acid, pure ethyl alcohol, pure hydrocarbons, lube oil, etc. Typical ionically conductive fluids, also by way of illustration only, are sea water, THF plus lithium perchlorate, any salt (e.g. NaCl, KCl, etc) dissolved in a solvent, such as water, etc.

To conduct electrochemical measurements in an electrically insulating or generally nonionic conductive compound, fluid, mixture, or the like (hereinafter referred to only as compound(s))to determine the purity or quality of any of the same, a set of calibration points, a calibration table, calibration data, or a calibration curve, or the like, (hereinafter referred to only as calibration curve) is initially generated. The corrosion probe 12 of embodiments 12-27 with platinum electrodes would be inserted into the compound(s), and a series of incremental increasing or decreasing known differences in potential, or a series of incremental increasing or decreasing known applied current densities would be signaled to the corrosion probe 12. In response to each known difference in potential or each known applied current density, a current or a difference in potential would be measured, depending upon if the known difference in potential or the known current was initially signaled.

For the purposes of describing the operation of the corrosion probe 12 to generate a calibration curve or the like and/or to measure electrochemically active compounds in generally nonionic conductive fluids, a known difference in potential will be signaled to the corrosion probe 12 to obtain a measured current in response to the signaled known difference in potential. It should be understood that the generation of the calibration curve or the like may also be accomplished by signaling or transmitting known applied currents(or current densities) instead of known differences in potential. Also for purposes of describing the invention, a calibration curve will be generated, but it should be understood that a set of calibration points, a calibration table, or the like, may likewise be generated.

With a series of voltage/current points plotted on a voltage vs. current graph, a calibration curve or line (e.g. the a.r. (as received) THF line in FIG. 42) is generated which may be used in combination with the corrosion probe 12 to electrochemically test the purity or quality of an electrically insulating, or generally nonionic conductive, compound(s), or the like, of the type with which the calibration or line curve was generated. Thus, to electrochemically test the purity or quality of the particular compound(s), for whose type the calibration curve was generated, the corrosion probe 12 would be inserted into the compound(s), to be tested electrochemically, and a known difference in potential would be transmitted to the probe 12 and a current in response to the transmitted known difference in potential would be measured. The known difference in potential and the measured current in response to the known difference in potential would be compared with the calibration curve that was generated. If the measured current in response to the known difference in potential is larger than the current on the calibration curve or line corresponding to the same known difference in potential, then the particular compound(s) being tested would contain an electroactive material (or more electroactive material) since more current was conducted through the particular compound(s), for the same known difference in potential.

The corrosion probe 12 may be used to quantitatively determine the electroactive component within a generally nonionic conductive fluid. Initially, a family of calibration curves is generated with various quantities of the electroactive component within the generally nonionic conductive fluid. For each quantity of electroactive component within the generally nonionic conductive fluid, a series of voltage/measured current points would be obtained and plotted on a graph whose horizontal axis represents electroactive component quantity and whose vertical axis represents current. A family of constant voltage curves would be constructed on the graph of electroactive component quantity vs current, such as in FIG. 43. With the use of the family of constant voltage curves and the corrosion probe 12, a generally nonionic conductive fluid of the type for which the family of constant voltage curves was generated may be electrochemically tested and analyzed to determine the quantity of the electroactive component within the generally nonionic conductive fluid.

To perform such a test, one of the voltages from the family of constant voltage curves would be applied to the probe 12 after the same was inserted into the generally nonionic conductive fluid to be tested. The current signal in response to the applied voltage is measured, is found on the vertical axis, and is subsequently located or placed therefrom along the constant voltage curve whose voltage was applied to the corrosion probe 12. The particular quantity of the electroactive component on the horizontal axis corresponding to the current signal measured and located on the constant voltage curve is the quantity of the electroactive component within the generally nonionic conductive fluid. This quantity may be verified for accuracy by applying to the corrosion probe 12 one or more voltages represented by other constant voltage curves. The respective currents in response from these applied voltages are measured, are located on the vertical axis, and are subsequently plotted therefrom on the respective constant voltage curves whose voltages were applied to the corrosion probe 12. If the quantity of the electroactive component found on the horizontal axis corresponding to the point of the measured current along a particular constant voltage curve is identical to the initial quantity of the electroactive component determined, then the initial quantity of electroactive component has at least one verification for accuracy. The more voltages applied to the corrosion probe 12 and the more currents measured and plotted on the constant voltage curve in response to the voltage of same, the greater the accuracy of the verification, assuming that each quantity of the electroactive component corresponding to each of the measured currents plotted along the respective constant voltage curves is identical to the initial quantity of the electroactive component determined.

Alternatively to generating a family of constant voltage curves to quantitatively determine the electroactive component within a generally nonionic conductive fluid, a family of constant concentration of electroactive component (within the generally nonionic conductive fluid) curves may be generated on a graph whose horizontal axis represents applied voltage and whose vertical axis represents measured current. To generate such a family of curves, a first certain quantity of the electroactive component would be added to a given quantity of the generally nonionic conductive fluid. A series of known difference in potentials and a series of respective measured current in response to the series of known differences in potentials would be obtained and plotted on the graph to obtain a first constant concentration curve whose points along the curve define a series of measured currents in response to a known applied differences in potential for the first certain quantity of the electroactive component within the generally nonionic conductive fluid. A second certain quantity of the electroactive component would be added to the given quantity of the generally nonionic conductive fluid and the entire process is repeated to obtain a second constant concentration curve whose points along the curve define a series of measured currents in response to a series of known applied differences in potential for the second certain quantity of the electroactive component within the generally nonionic conductive fluid. A whole series of such curves may be generated for any particular quantity or concentration of the electroactive component within the generally nonionic conductive fluid.

Such a series of curves may be employed along with the corrosion probe 12 to determine the amount of the electroactive component in a given solution consisting of the generally nonionic conductive fluid and the electroactive component. If the corrosion probe 12 is inserted into a generally nonionic conductive fluid whose electroactive component is to be determined, and a known difference in potential is applied to the corrosion probe 12, a signal current may be measured in response to this known applied difference in potential. If the known applied potential/measured signal current is located or plotted as a point on the graph of the family of curves for various amounts or concentration of the electroactive component, the particular curve upon which the point is plotted represents the amount or concentration of the electroactive component within the generally nonionic conductive fluid.

It should be understood that while the procedure to generate calibration data has been described (and will be further described in the Examples below) with respect to a generally nonionic conductive fluid (i.e. THF) alone, or an electroactive component within a generally nonionic conductive fluid, calibration data may be generated for a generally nonionic conductive fluid having two or more electroactive components. A series of increasing voltages would be applied to a given generally nonionic conductive fluid with, by way of example only, two electroactive components. The applied voltage vs measured current curve would initially rise with increasing voltage and then plateau (or level off) for a period of increasing voltage, and then rise again with increasing voltage. If there were three or more electroactive components present there would be a whole series of plateaus and increasing measured currents with increasing applied voltages. The measured current associated with the second electroactive component would be the difference between the total measured current and the current measured at the first plateau where current remained constant with respect to increasing voltages for the first electroactive component. The reason for plateaus is that every electroactive molecule for a particular electroactive component is electrochemically converted (i.e. reacted) at the face of the probe 12. At the plateaus, the increase in voltage does not accelerate the rate at which the first electroactive component or any other electroactive component arrives at the face of the electrode 12. Therefore, the current is relatively constant.

It should be understood that while only one method for electrochemical analysis of electroactive component(s) in a generally nonionic conductive fluid using the corrosion probe 12 has been disclosed, other means (e.g. polarography, voltammetry, or the like, etc.) using the corrosion probe 12 in any of its configurations for electrochemical analysis of electroactive component(s) in a nonionic conductive fluid are encompassed within the spirit and scope of this invention.

My invention will be illustrated by the following set forth examples which are given by way of illustration and not by any limitation. All parameters such as distances,, concentrations, compounds, temperatures, rates, times, etc., submitted in these examples are not to be construed to unduly limit the scope of my invention. The potentials and currents were respectively read with a Keithly 616 Digital Electrometer, voltmeter 50, and a Keithly battery powered electrometer Model 600B, meter 48. The current readings were achieved with the resistor 46 set at 1 meg ohm. To further reduce noise so that small (of the order of 0.004 microaps) corrosion currents could be measured, all of the electronics, pumps and the autoclave in these examples were put to a common ground. This reduced ground loop currents to nominally 0.4 microamps in 40% brine/oil mixture. In a 2% brine/oil mixture the ground loop currents were reduced to even a smaller order of magnitude. Glass liners were used to further reduce these residual currents by a factor of nominally two. Any residual currents remaining were then nulled to zero by adjusting the output potential to zero current as read by meter 48, the Keithly electrometer. Ground loop currents can also be reduced to zero by using a potentiostat which does not internally ground the working (sample) electrode. Corrosion currents in these examples were calculated from the Stern-Geary equation with a computer using a computer curve fitting procedure as described by N. Greene and R. Gandhi in Materials Perf. 21,34 (July 1982). Typical Tafel constants were BA=70 mv/decade and BC=110 mv/decade. These were independent of probe design as indeed they should have been, being constants related to the corrosion mechanism per se.

For the embodiment of the corrosion probe 2 in FIGS. 2-11, the interelectrode resistances were a function of the particular crude, brine content, stirring rate and probe configuration, which again they should be since they are related to the arrival of brine at the electrode-mixture interface. Certain interelectrode resistances, by way of illustration only, between the working electrode 16 and the reference electrode 20 were as follows:

| Mixture | Resistance, (megohms) | |
|---|---|---|
| | Ring/Disc Probe (FIGS. 6-11) | Parallel Electrode (FIGS. 2 & 3) |
| Crude A | 1.0 | 0.14 |
| Crude A + 2% Brine | 0.65 | 0.11 |
| Crude B | 0.83 | 0.04 |
| Crude B + 2% Brine | 0.005 | 0.004 |
| Crude B + 15% Brine | 0.2 | * |
| Crude B + 40% Brine | 0.21 | 0.04 |
| Crude C + .2% Brine | 1.0 | .14 |
| Crude C + 2% Brine | .65 | .112 |
| Crude C + 5% Brine | .256 | .027 |
| Crude C + 10% Brine | .28 | .0018 |
| Crude C + 15% Brine | .24 | .0054 |
| Crude C + 20% Brine | .292 | .022 |
| Crude D | .825 | .06 |
| Crude D + 2% Brine | .249 | .053 |
| Crude D + 5% Brine | .0057 | * |

*Not measured

The predetermined differences in potential between reference electrode 18 and an area in the surrounding corrosive liquid in general microscopic proximity thereto were taken to be that potential measured between the working electrode 16 and the reference electrode 18 when the amperage was zero or at zero current flow, as was previously mentioned. As was also previously mentioned, it is necessary only that the additional e.m.f. (overvoltage) to pass current be determined. The predetermined differences in potential, by was of illustration only, between the reference electrode 18 and certain particular crudes and certain crude/brine mixtures for the various embodiments of the probe 12 in FIGS. 2-11 were was follows:

| Mixtures | Difference in Potential, (volts) | |
|---|---|---|
| | Ring/Disc Probe (FIGS. 6–11) | Parallel Electrode Probe (FIGS. 2 & 3) |
| Crude B + 40% Brine | * | −.0140 |
| Crude C + 0.2% Brine | +0.1136 | −.01308 |
| Crude C + 2% Brine | +.0750 | −.0414 |
| Crude C + 5% Brine | +.0683 | −.0368 |
| Crude C + 10% Brine | +.0220 | −.0104 |
| Crude C + 15% Brine | −.01370 | −.00738 |
| Crude C + 20% Brine | +.0125 | −.0291 |
| Crude D | +.0403 | −.01322 |
| Crude D + 2 % Brine | +.0195 | −.0032 |
| Crude D + 5% Brine | +.01463 | * |

*Not measured

The predetermined differences in potential between the reference electrode 18 and certain particular crudes and certain crude/brine mixtures for the various embodiments of the probe 12 in FIGS. 12–27 were, by way of illustration only, as follows:

| Mixtures | Difference in Potential, (volts) | |
|---|---|---|
| | Ring/Disc Probe (FIGS. 24 & 25) | Parallel Electrode Probe (FIGS. 20 & 21) |
| Crude B + 40% Brine | * | * |
| Crude C + 0.2% Brine | +0.1136 | +.01136 |
| Crude C + 2% Brine | +.0750 | +.0750 |
| Crude C + 5% Brine | +.0683 | +.0683 |
| Crude C + 10% Brine | +.0220 | +.0220 |
| Crude C + 15% Brine | −.01370 | −.01370 |
| Crude C + 20% Brine | +.0125 | +.0125 |
| Crude D | +.0403 | +.0403 |
| Crude D + 2% Brine | +.0195 | +.0195 |
| Crude D + 5% Brine | +.01463 | +.01463 |

*Not measured

High pressure measurements in these following examples were made in a standard Autoclave Engineering 2-liter, 316 stainless steel autoclave. Electrode probes were passed through the autoclave lid with standard Swagelok fittings to within 1 ⅜" of the autoclave base. Pressure was monitored with an Autoclave Engineering digital meter with a solid state sensor, Model T 5106-05-B10. The $CO_2$ pressure was held at 760±20 psig. Temperature control was via an Autoclave Engineering temperature controller "Solid State Controller #520." This particular unit cycled between 19° F. and 174° F. over a nominally 90 minute period when set for 185° F. This had a negligible effect on corrosion rate. Measurements of the corrosion rate parameter were at 186° ± 3° F. This variation was reduced to about half by manual adjustment of the power to the heater while successive measurements were being made.

EXAMPLE I

Figure 34:
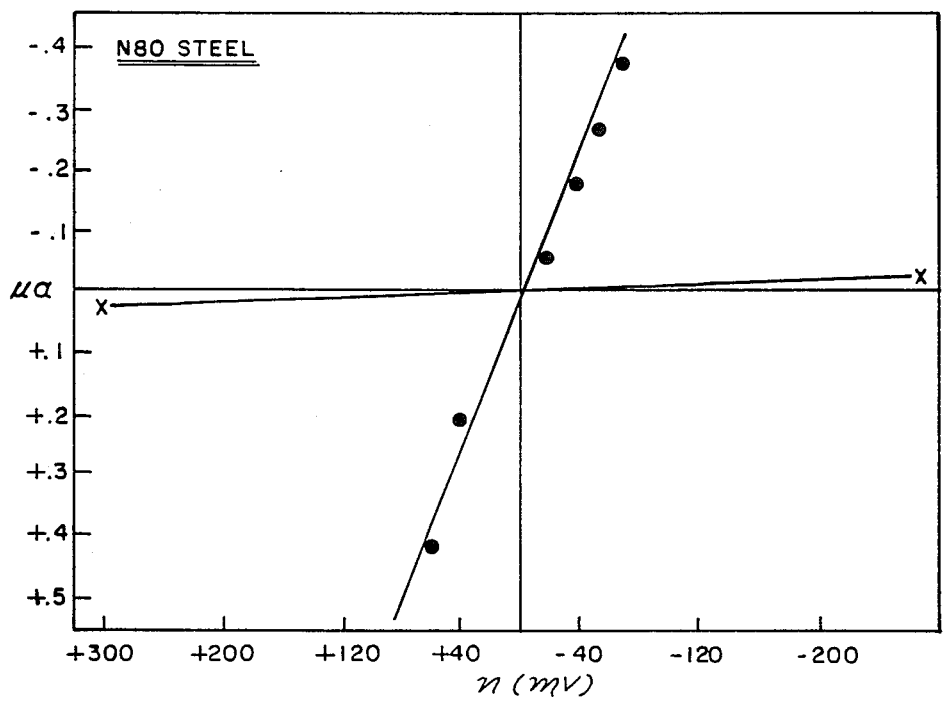
FIG. 34 is a corrosion current/potential curve for the probe of FIGS. 6, 7, and 11 before and after the surface is rendered ionically conductive, in this case by treatment with hot KOH.

Current-potential curves measured in the 40% brine in Crude B crude oil are shown in FIG. 34 for the probe 12 embodiment of FIGS. 6, 7 and 11, before and after activation with 10M KOH, 80° C. (2 hrs.). The measured current (microamps) for before and after activation was −0.002 and −0.1, respectively at e.m.f. (volts) between reference electrode 18 and the working electrode 16 for before and after activation of −0.732 and −0.401, respectively. The resistance (megohms) between reference electrode 18 and working electrode 16 in each case was 0.8 and 0.095, respectively. The e.m.f. (volts) between the reference electrode 18 and a point in the crude in the immediate vicinity of the reference electrode 18 was −0.266 for before activation and −0.017 for after activation. The corrosion currents calculated were 0.0002 μa and 0.25 μa before and after activation, respectively. Clearly, the treatment with KOH generated a current response to the brine/oil mixture.

EXAMPLE II

Corrosion currents were measured with the KOH treated parallel electrode probe 12 (the embodiment of FIGS. 2 and 3) in Crude B crude oil that was deliberately made more corrosive by adding brine, increasing temperature and increasing carbon dioxide pressure. The following Table IV shows that the FIGS. 2 and 3 probe 12 responds to increasing corrosivity of brine/oil mixtures:

TABLE IV

Corrosion Currents Measured with Parallel Electrode Probe*
(30 minutes after admitting $CO_2$ to probe 12)

| Liquid | Temp. | $CO_2$ Pressure (psig) | Corrosion Current (microamps) | Applied Current (microamps) | Measured e.m.f. (volts) between R and W | Determined e.m.f. (volts) between R and pt in liquid |
|---|---|---|---|---|---|---|
| Crude B + 40% Brine | 75° F. | 15 | .0008 | −.02 | −.590 | −.540 |
| | 150° F. | 15 | .02 | −.02 | −.130 | −.024 |
| | 185° F. | 15 | .12 | +.20 | +.0321 | +.035 |
| | 185° F. | 775 | .53 | +.20 | +.016 | +.008 |
| Pure Brine | 185° F. | 775 | 206. | +98 | +0055 | +0.10 |

*Sheets in sequence
R - W - C - W - R - W - C - W - R (where R = reference, W = working, C = counter).
All like electrodes are electrically in parallel.

The oil/40% brine mixtures increase in corrosivity with increasing $CO_2$ pressure and/or brine cut and/or temperature. The measured corrosion current increases as the corrosivity of the mixture increases.

EXAMPLE III

Example II was repeated but with Crude D and with a KOH treated probe 12 having the embodiment of FIGS. 6, 7 and 11 and the results found are in the following Table V:

TABLE V

Corrosion Currents Measured with FIGS. 6, 7 and 11 Probe

| Liquid | Temp. | CO₂ Pressure (psig) | Applied Current (microamps) | Measured e.m.f. (volts) between R and W | Determined e.m.f. (volts) between R and pt. in liquid | Corrosion Current (microamps) |
|---|---|---|---|---|---|---|
| Crude D as received | 185° F. | 760 | +.01 | −.0232 | +.00885 | .023 |
| Crude D/brine mixture 2% brine | | 760 | +.02 | +.0323 | +.00782 | .053 |
| 5% brine | | 760 | −.2 | +.01780 | −.0153 | .30 |

EXAMPLE IV

Figure 35:
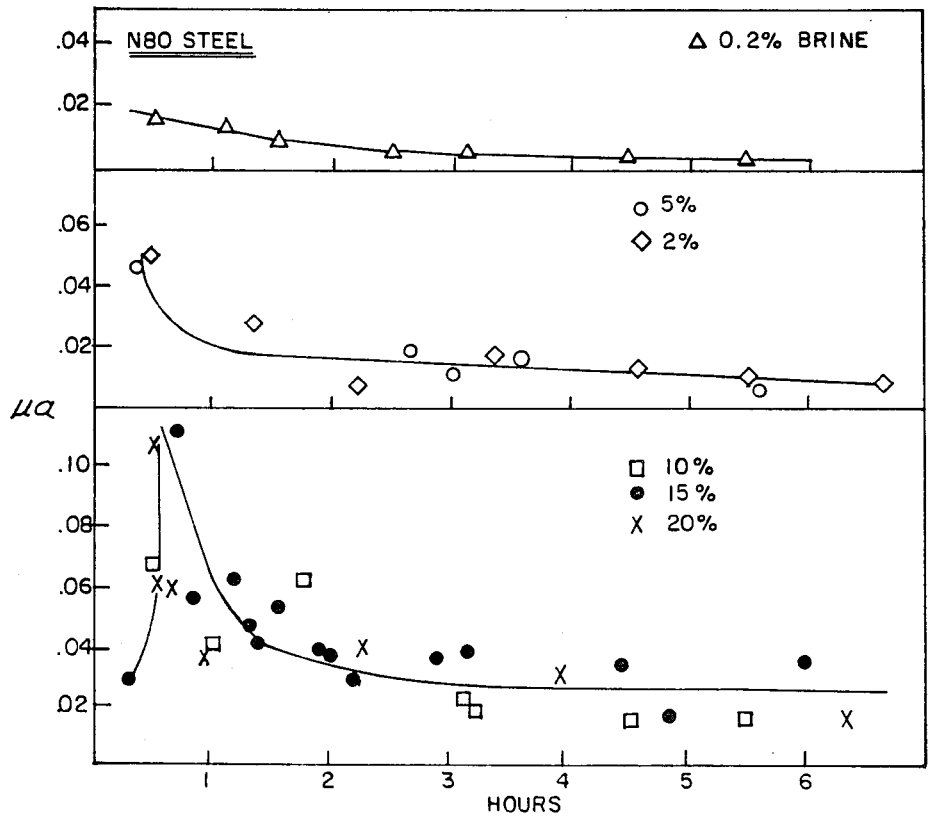
FIG. 35 is a corrosion current/time profile for varying % brine in a crude at 185° F. with 760 psig. carbon dioxide.

Corrosion current-time profiles for N80 steel at different quantities of the 4 percent (%) brine in Crude C crude are shown in FIG. 35, measured with the probe 12 embodiment of FIGS. 6, 7 and 11 in the autoclave at nominally 760 psig. $CO_2$, 185° F. under the following conditions:

| Liquid | Applied current (microamps) | Measured e.m.f. (volts) between R and W | Determined e.m.f. (volts) between R and pt. in liquid | $I_c$, corrosion current (microamps) |
|---|---|---|---|---|
| Crude C + 0.2% Brine | −.01 | +.0919 | −.0336 | .006 |
| Crude C + 2% Brine | −.006 | +.0639 | −.0069 | .018 |
| Crude C + 5% Brine | −.01 | +.1627 | −.00554 | .037 |
| Crude C + 10% Brine | −.002 | +.01176 | −.00064 | .035 |
| Crude C + 15% Brine | −.02 | −.0257 | −.00724 | .058 |
| Crude C + 20% Brine | −.04 | −.0227 | −.019 | .044 |

Figure 38:
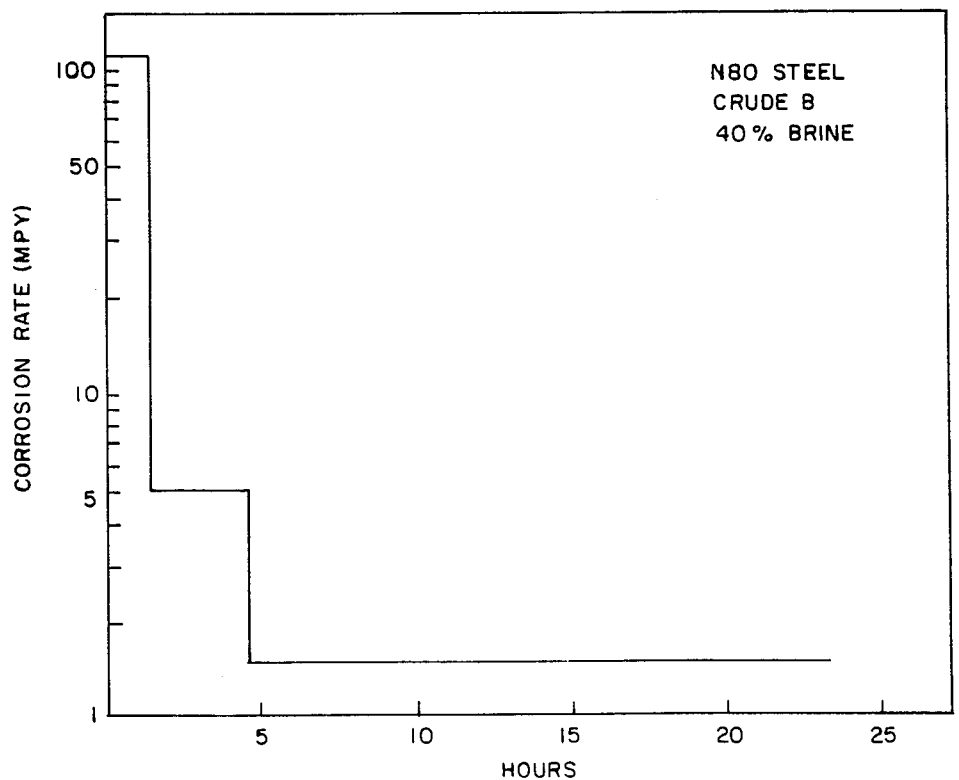
FIG. 38 is a corrosion rate (weight loss) vs. time for N80 steel in a 40% brine crude, 760 psig. $CO_2$, 185° F.

In all cases there generally appears to be a more rapid corrosion process at the beginning, dropping off with time a lower steady-state rate. The same conclusion is found in FIG. 38 with the conventional coupon weight-loss technique (see for example, at 5 hours, the data for Crude B, 40% Brine, 760 psig. $CO_2$, 185° F. with an applied current ($\mu$a) of 0.1, a measured e.m.f. (volts) between R and W of −0.331, a determined e.m.f. (volts) between R and a pt. in liquid of 0.007). In both cases the steel surface of the working electrode 16 was coated with $FeCO_3$. The corrosion currents at about 5 to 10 hours, after initiation of $CO_2$ induced corrosion at 760 psig $CO_2$ and 185° F., are a weak function of brine count, as also evidenced in Table V.

EXAMPLE V

Figure 36:
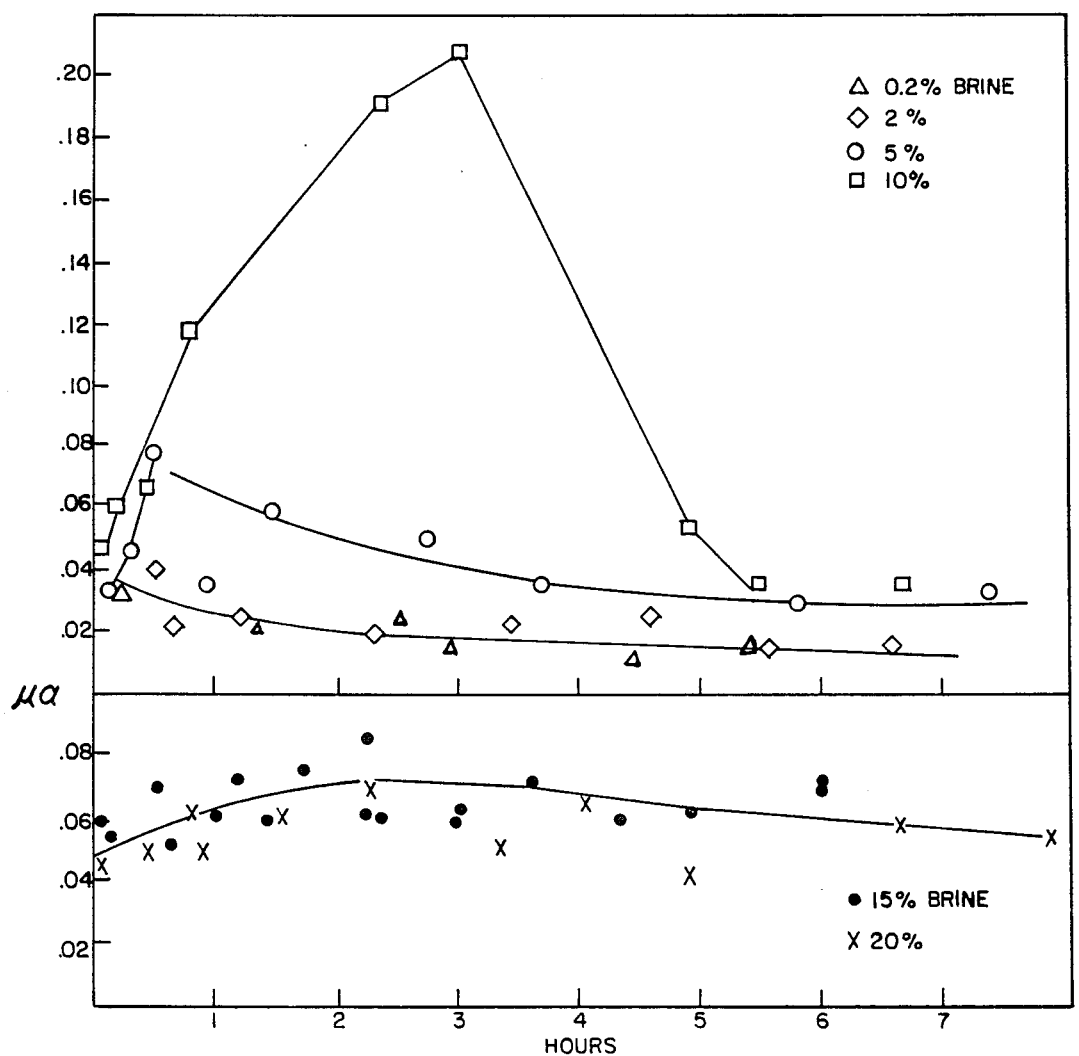
FIG. 36 is a corrosion current/time profile for varying % brine for a parallel electrode probe in a crude at 185° F. with 760 psig. carbon dioxide.

Corrosion current-time profiles for the low alloy steel at different quantities of the 4 percent (%) brine in Crude C crude are shown in FIG. 36, measured with the probe 12 embodiment of FIGS. 2 and 3 in the autoclave at nominally 760 psig. $CO_2$, 185° F. under the following conditions:

| Liquid | Applied current, (microamps) | Measured e.m.f. between R and W, (volts) | Determined e.m.f. between R and pt in liquid, (volts) | $I_c$ corrosion current, (microamps) |
|---|---|---|---|---|
| Crude C + .2% Brine | −.01 | −.0219 | −.0077 | .027 |
| Crude C + 2% Brine | −.01 | −.0430 | −.006 | .035 |
| Crude C + 5% Brine | −.01 | −.0354 | −.0044 | .047 |
| Crude C + 10% Brine | −.01 | −.01740 | −.00345 | .06 |
| Crude C + 15% Brine | −.01 | −.0316 | −.00383 | .054 |
| Crude C + 20% Brine | −.01 | −.0349 | −.00479 | .044 |

There again appears to be a rapid corrosion process at the beginning followed by a slower corrosion process.

EXAMPLE VI

Figure 37:
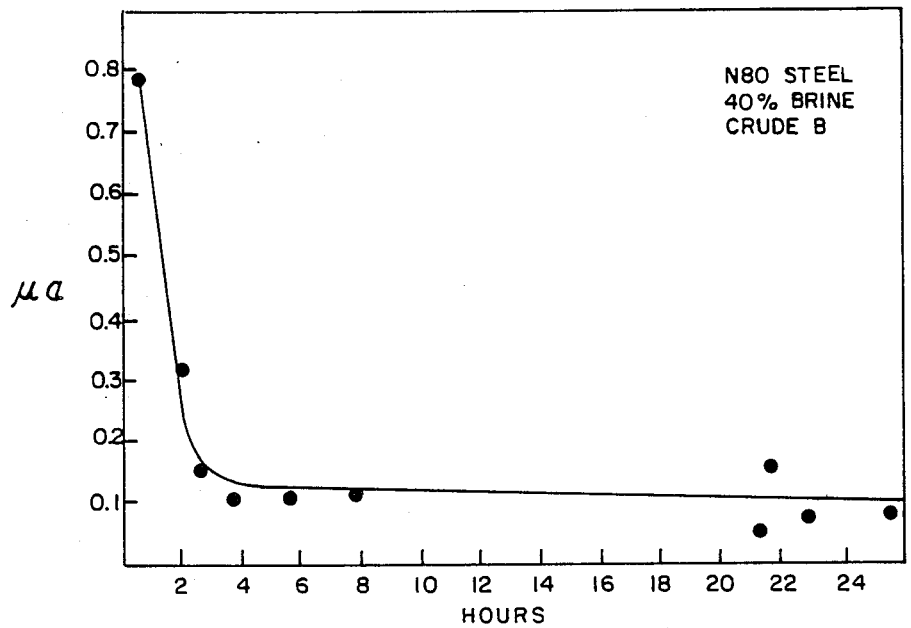
FIG. 37 is a corrosion current vs. time for N80 steel in a 40% brine crude at 185° F. with 760 psig. carbon dioxide.

A corrosion current-time profile for N80 steel in 40% brine in Crude B crude is shown in FIG. 37, measured with the probe 12 embodiment of FIG. 6, 7 and 11 in the autoclave at nominally 760 psig. $CO_2$, 185° F. The data at 22 hours was calculated from an applied current ($\mu$a) of +0.1, a measured e.m.f. (volts) between R and W of −0.289, a determined e.m.f. (volts) between R and pt. in liquid of +0.009. Again, there was rapid corrosion initially, followed by passivation to a slower steady-state corrosion rate.

EXAMPLE VII

The following is a comparison of the corrosion rates (which are multiplied by a factor of 11) obtained by the embodiment of the probe 12 in FIGS. 2–11 and those obtained by conventional weight loss measurements:

Comparison of Corrosion Rate Measurements in Oil and Brine, averaged over 24 hrs, (mpy)

| System | Gas | Temp. | Corrosion rat measurements, (mpy) | |
|---|---|---|---|---|
| | | | Coupon | Prob |
| 95% Crude C | 760 psig $CO_2$ | 185° F. | 5.2 | 6.2 |
| 95% Crude S | 760 psig $CO_2$ | 185° F. | .71 | .7 |
| 60% Crude D | 760 psig $CO_2$ | 185° F. | 1.0 | 1.1 |

The corrosion rates measured by the embodiment of the probe in FIGS. 2–11 are proportional to the corrosion rates as measured by the coupon weight loss.

EXAMPLE VIII

Figure 39:
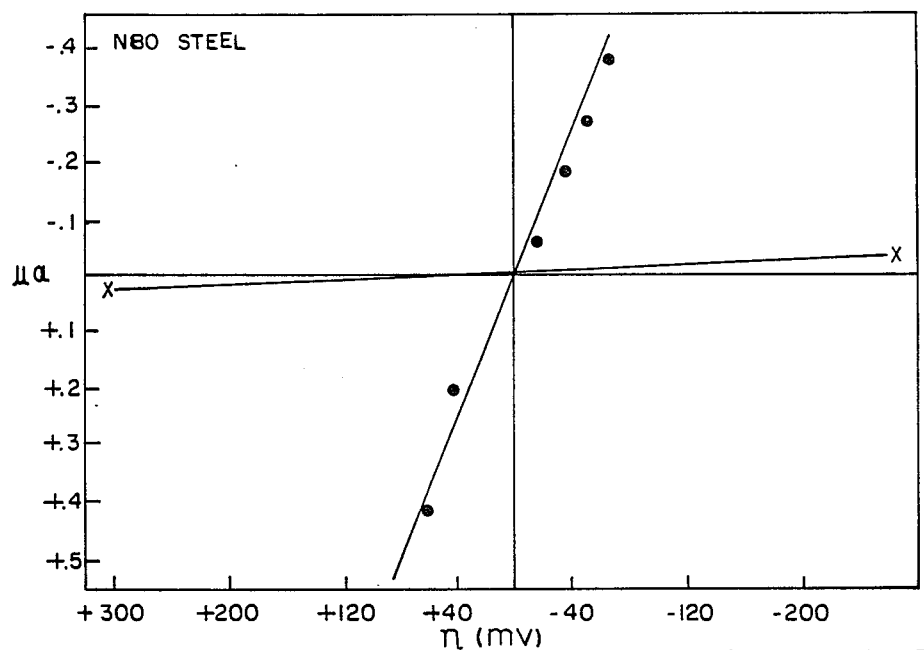
FIG. 39 is a corrosion current/potential curve for the improved probe of FIGS. 24 and 25 before and after the surface is rendered ionically conducting, in this case by treatment with hot KOH.

FIG. 39 shows the measurement of current-potential curves in the 40% brine in Crude B crude for the probe 12 embodiment of FIGS. 24 and 25, before and after activation with 10M KOH, 80° C. (2 hrs.). The measurements of the current (microamps) for before and after activation are −0.002 and −0.1, respectively a e.m.f. (volts) between reference electrode 18 and the working electrode 16 for before and after activation of −0.732 and −0.401, respectively. The resistance (megohms) between reference electrode 18 and working electrode 16 in each case is 0.8 and 0.095, respectively. The e.m.f. (volts) between the reference electrode 18 and a point in the crude in the immediate vicinity of the reference electrode 18 is −0.266 for before activation and 0.017 for after activation. The corrosion currents calculated are 0.0002 $\mu a$ and 0.25 $\mu a$ before and after activation, respectively. Clearly, the treatment with KOH generates a current response to the brine/oil mixture.

EXAMPLE IX

Corrosion currents were measured with a KOH treated probe 12 having the embodiment of FIGS. 24 and 25, and with a KOH treated probe 12 having the embodiment of FIGS. 6 and 7. Both embodiments of the probe 12 were in Crude D crude oil at a temperature of 185° F. and a $CO_2$ pressure of 760 psig. The results are found in the following Table VI (note that since the electrodes varied in surface area the corrrosion currents are given in terms of microamps per cm$^2$):

TABLE VI

CORROSION CURRENTS MEASURED WITH FIGS. 24 AND 25 PROBE AND FIGS. 6 AND 7 PROBE
(Crude Oil D, 760 psig $CO_2$, 185° F.)

| Liquid | Applied Current (microamps) | Measured e.m.f. between R and W, (volts) | | Determined e.m.f. between R and Point in Liquid, (volts) | Corrosion Current Density, (microamps/cm$^2$) | |
|---|---|---|---|---|---|---|
| | | FIGS. 6 & 7 Probe | FIGS. 24 & 25 Probe | | FIGS. 6 & 7 Probe | FIGS. 24 and 25 Probe |
| Crude D as received | +.01 | −.0232 | −0.1535 | +.00885 | .11 | 0.1 |
| Crude D/brine mixture 2% brine | +.02 | +.0323 | −.00618 | +.00782 | 0.27 | 0.45 |
| 5% brine | −.2 | +.01780 | −.01084 | −.0153 | 1.45 | 11.3 |

TABLE VII

Corrosion Rates in Brine/Crude Oil
(24 Hr., 760 psig $CO_2$, 185° F., NaCl Brine)

| | Corrosion Rate (mpy) | |
|---|---|---|
| Crude Oil | Weight Loss | Electrochemical (Improved) |
| 95% E | 34. | 28. |
| 95% C | 3. | 5. |
| 95% D | 0.4 | 0.3 |
| 100% C | 1.1 | 0.8 |

EXAMPLE XII

The embodiment of the corrosion probe of FIGS. 26 and 27 was connected (as in FIG. 1) at right angle to flow in the center of a 6 inch diameter flowline, horizontal section 20 feet from the wellhead of a well flowing 12,500 bbls. oil per day, 200 psig, 150° F., 12% $CO_2$, and 200 ppm $H_2S$. A prior art device (e.g., corrosometer), measuring the electrical resistance of a corroding wire, was similarly positioned as the corrosion probe, but 10 feet from the wellhead. A 7 mv voltage was dialed into the potentiostat means every day at noon to make a measurement, requiring nominally 20 secs. A meter current reading was taken and calibrated into a corrosion rate in mpy (mils per year). A reading was made on the prior art device - corrosometer. At each reading, a % water cut by volume was determined Each reading, calibration, and determination was plotted versus the particular day they were made. The resulting plots are in FIG. 41. The breaks in the plots between days 37 and 44 were due to the fact that the field engineer was not available to make the readings and the % water cut determination. The breaks in the % water cut by volume plot between day 7 and day 17 was due to the fact that the field engineer did not make the % water cut determination. The straight line through each plot is a trend line.

Figure 41:
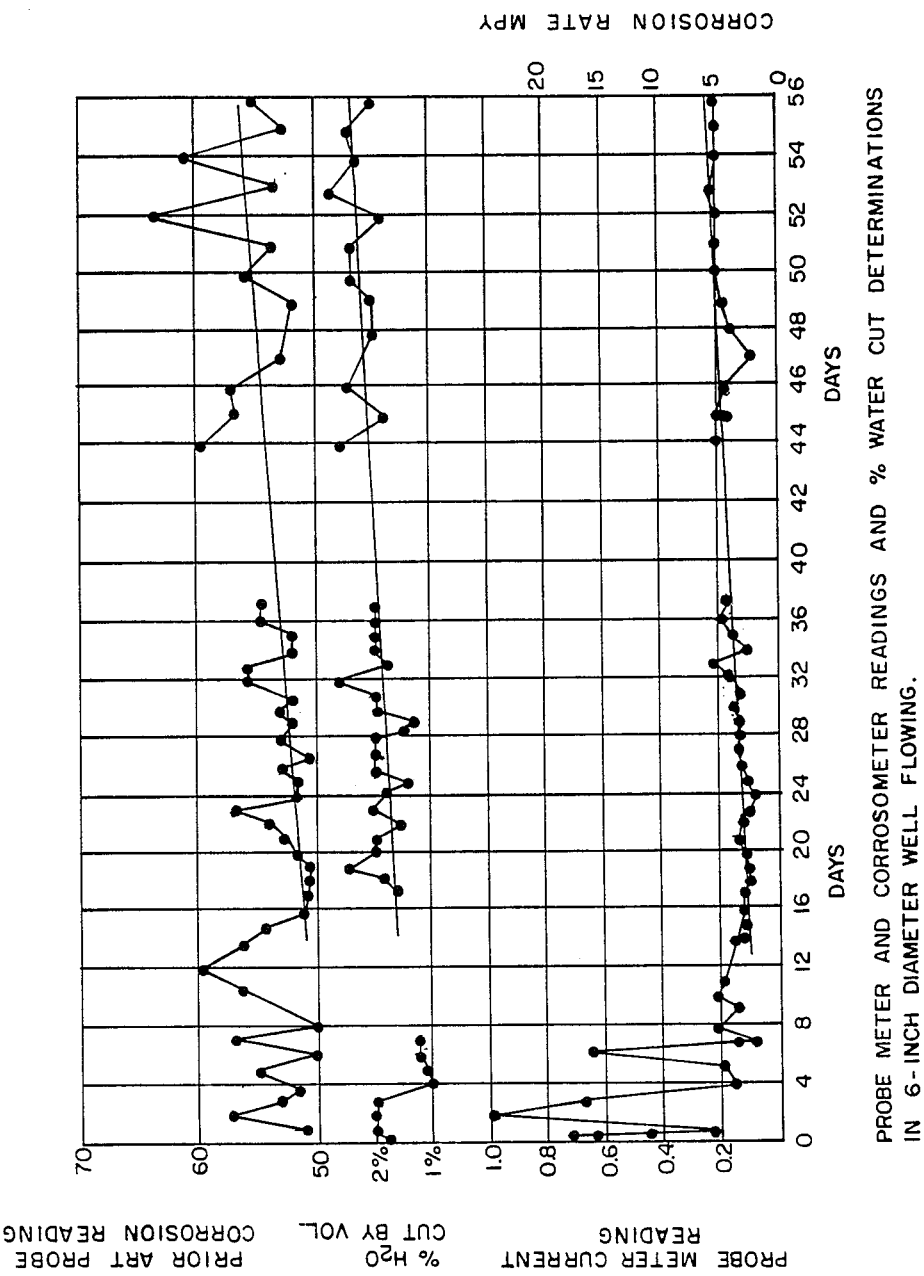
FIG. 41 is probe meter current reading versus days for the improved corrosion probe, corrosion rate (mpy) versus days for the improved corrosion probe, determined % water cut versus days, and prior art device corrosion reading versus days, all from a well flowing 12,500 bbls. oil per day, 200 psig., 150° F., 12% $CO_2$, and 200 ppm $H_2S$.

The results in FIG. 41 illustrate that as the % water cut by volume increases, the meter current reading of the corrosion probe of FIGS. 26 and 27 increases along with the calibrated corrosion rates. The prior art device corrosion reading also increases with increasing % water cut by volume, but the points are more scattered than the points obtained with the corrosion probe of this invention. It is clear from FIG. 41 that the corrosion probe of this invention gives a more sensitive, stable and precise indication of increasing corrosion rate, with increasing % water cut, than the prior art device - corrosometer.

EXAMPLE X

Figure 40:
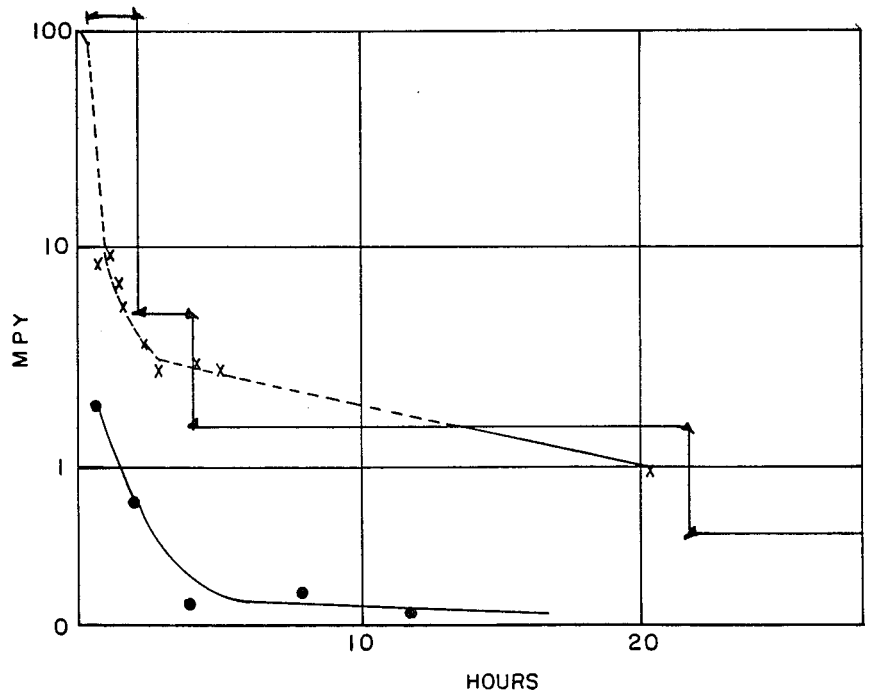
FIG. 40 is corrosion rate (mpy)/time profiles (hours) for the improved corrosion probe of FIGS. 24–25, the corrosion probe of FIGS. 6 and 7, and coupon weight loss, in a 40% brine crude at 185° F. with 760 psig. carbon dioxide.

Corrosion rate-time profiles for N80 steel in the 40 percent (%) brine in Crude A crude are shown in FIG. 40, measured with the probe 12 embodiment of FIGS. 24 and 25 and the probe 12 embodiment of FIGS. 6 and 7. The measurements were in the autoclave 15 at nominally 760 psig. $CO_2$, 185° F. Also included are the corrosion rates measured by the coupon weight loss. In all cases there generally appears to be a more rapid corrosion process at the beginning, dropping off with time to a lower steady-state rate. Clearly, the electrochemical corrosion rates measured with my improved probe of FIGS. 24 and 25 are in closer agreement to those measured by weight loss of coupons than the corrosion rates measured with my probe of FIGS. 6 and 7.

EXAMPLE XI

Shown in the following Table VII are the average corrosion rates (for 24 hours) as measured by the improved electrochemical technique with the improved probe of FIGS. 24 and 25 and by the weight loss of coupons. Obviously, both techniques give comparable results.

EXAMPLE XIII

The corrodant used in this test was a commercially available, standard pH2 buffer solution, deaerated with nitrogen. A corrosion probe 12 of the embodiment in FIGS. 28-33 (i.e. with a plurality of working electrodes 16A, 16B etc.) was employed to determine the corrosion rate upon each of the working electrodes. The multi-metal working electrode probe 12 consisted of a 0.25 in. diameter N80 steel rod, surrounded in the following order: 0.025 in. wide cylinder of phenolic resin dielectric, 0.025 in. wide cylinder of 316 stainless steel (ss), 0.025 in. wide cylinder of phenolic resin dielectric, 0.025 in. wide cylinder of N80 steel, 0.025 in. wide cylinder of phenolic resin dielectric, all contained within a 316 ss tube with the appropriate retaining material 60 added. The 316 ss tube was also used as the counter electrode 20 for measuring the corrosion rate of the N80 ring; the 316 ss ring served as the reference electrode 18. A cathodic current of 5 microamps was produced at a polarization of 10 millivolts, representing a corrosion rate for the N80 steel of 14 mils per year (mpy). Identical corrosion measurements were made with the 316 ss ring in the same solution with the same probe. Here a cathodic current of 0.1 microamps was produced at a polarization of the 316 ss surface by 70 millivolts, for a corrosion rate of 0.06 mpy.

EXAMPLE XIV

The probe described in Example XIII was used to measure the corrosivities of these two metals, 316 stainless steel and N80 steel, in a CO -brine-in-crude oil mixture (760 psig CO , 186° F.). Since the resistivity of this fluid mixture was very high, it was necessary that the phenolic dielectric surface be made ionically conductive. After the dielectric surface was made ionically conductive at the appropriate places, a cathodic current of 1 microamp was passed through the 316 ss ring (20 minutes after introducing the carbon dioxide corrodant). This current through the 316 ss ring produced a polarization of 31 millivolts, representing a corrosion rate of 1.3 mpy. The electrical potential of the steel ring at +330 mv. vs. N80 steel also implied that this ss surface was in the passive state. Polarization of the N80 ring at this early time in the corrosion process was difficult, indicating a corrosion rate greater than 1000 mpy; this low alloy steel surface was in the "active state". It is well known that prolonged corrosion of N80 steel by $CO_2$ can produce a surface film of insoluble iron carbonate. This film can passivate the surface to further reduce corrosion. After 24 hours, a current of 0.03 microamp polarized the N80 steel by 21 mv, indicating a corrosion rate of 0.06 mpy. The stainless steel surface was also found to be in the passive state at this time.

EXAMPLE XV

Figure 42:
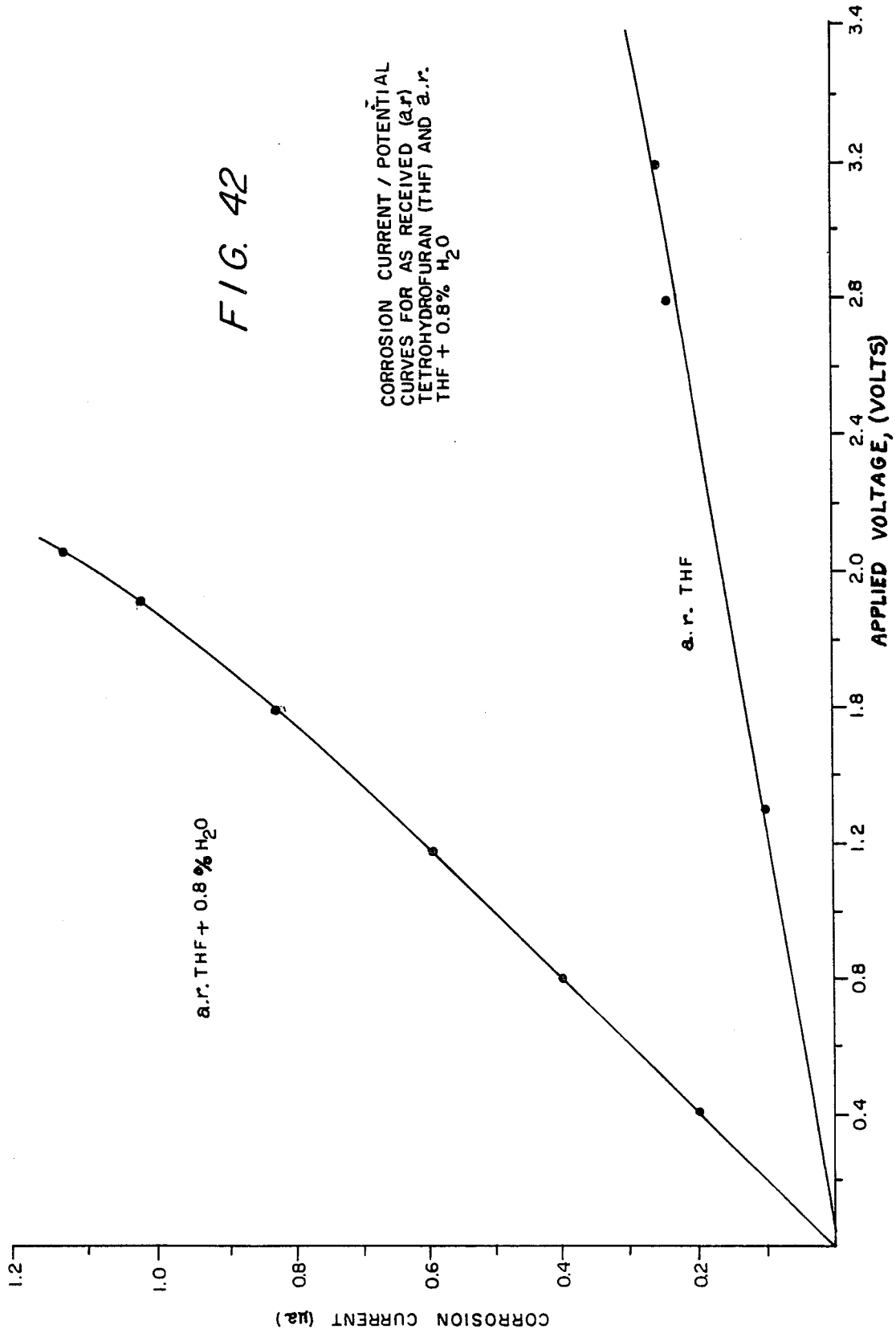
FIG. 42 is a calibration curve for a.r. (as received) Tetrahydrofuran (THF) and a.r. THF plus 0.8% $H_2O$, with each curve representing measured currents in microamperes ($\mu a$) in response to applied voltages.

The corrosion probe 12 of FIGS. 24 and 25 was manufactured with a caustic-attacked phenolic resin ionically conductive the reference electrode 18 from the working electrode 16. All electrodes (i.e. working electrode 16, reference electrode 18 and counter electrode 20) were manufactured of platinized steel. The corrosion probe 12 was inserted into pure, salt-free tetrahydrofuran (THF) to generate a calibration curve. As illustrated in FIG. 42, when 1.3 volts difference in potential was applied between the working and reference platinized electrodes 16 and 18 respectively, approximately 0.1 $\mu$a of current flowed betweeen the working and counter platinized electrodes 16 and 20, respectively. Similarly, when about 2.8 volts and about 3.2 volts were applied, approximately 0.24 and 0.26 $\mu$a of current were measured as flowing. With these three points a voltage-current curve was generated for pure, salt-free THF; and through the use of this curve, any purportedly pure THF solution (i.e. free of electroactive materials) may be tested with the corrosion probe 12 to see if in fact the THF is pure. The corrosion probe 12 would be inserted into the purportedly pure THF solution, and a given voltage would be signaled and a current would be measured. If the voltage-current point falls above the pure THF curve in FIG. 42, the purportedly pure THF is not pure but would contain an electroactive material since more current was allowed to be conducted through the purportedly pure THF solution in response to the given voltage signaled. Had the purportedly pure THF solution been pure, the voltage-current point would fall approximately on the generated calibration curve for pure THF.

EXAMPLE XVI

To the THF solution of Example XV 0.8% water was added. The corrosion probe 12 of Example XV was inserted into the THF/0.8% water solution; and when approximately 0.4, 0.8, 1.2, 1.6, 1.9 and 2.1 volts were respectively signaled and applied the following approximate $\mu$a of current were respectively read in response to the volts: 0.2, 0.4, 0.6, 0.85, 1.05, and 1.15. With these voltage-current points, a voltage-current curve was generated, as illustrated in FIG. 42, for a THF/0.8% water solution. Molecular water on platinum can be electrolytically oxidized to form oxygen gas and can also beelectrolytically reduced to form hydrogen gas (i.e. water is "electrochemically active").

Through the use of this curve and the corrosion probe 12, a THF/water solution may be tested to determine the amount of water contained within the THF/water solution. The corrosion probe 12 would be inserted into the THF/water solution, and a given voltage would be signaled and a current would be measured in response to the given, signaled voltage. If the voltage-current point falls above the THF/0.8% water curve in FIG. 42, the THF/water solution would contain more than 0.8% water, the electroactive material or component, since more current flowed through the THF/water solution in response to the given, signaled voltage, than the current which would have flowed through the THF/0.8% water solution had the same given voltage been signaled. If the voltage-current point falls below the THF/0.8% water curve (i.e. between the pure THF curve and the THF/0.8% water curve), the THF/water solution would contain less than 0.8% water since less current flowed through the THF/water solution in response to the given, signaled voltage, than the current which would have flowed through the THF/0.8% water solution had the same given voltage been signaled. If the voltage-current point falls on the THF/0.8% water curve, the THF/water solution would contain 0.8% water.

EXAMPLE XVII

Figure 43:
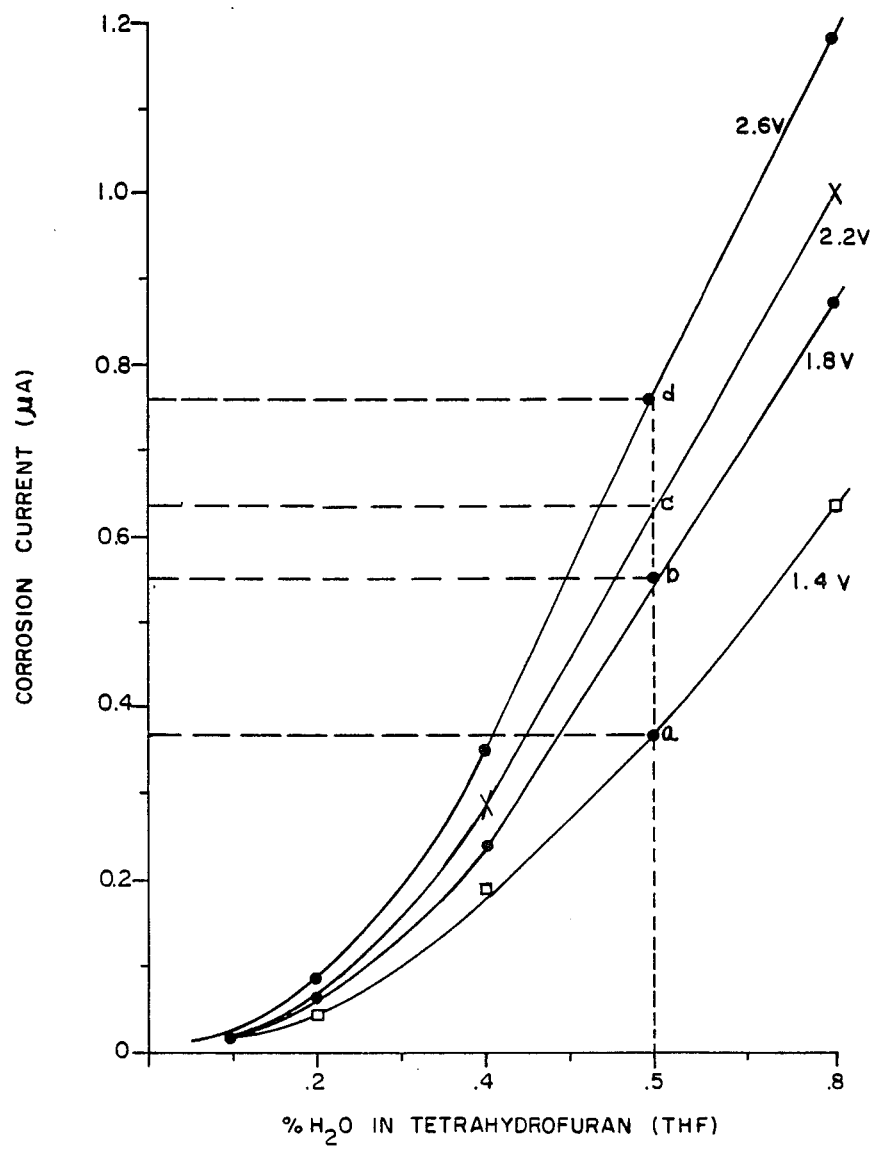
FIG. 43 is a family of constant voltage curves plotted on a graph of % $H_2O$ in tetrahydrofuran (THF) vs. measured current ($\mu a$) in response to applied voltages.

To the pure THF solution of Example XV, 0.2% water was added and 1.4, 1.8, 2.2 and 2.6 volts were signaled to the corrosion probe 12 after it was inserted into the THF/0.2% water solution. The 0.2% water current points were plotted on the graph of FIG. 43. The currents measured in response to each of these volts were less than about 0.1 $\mu$a, as illustrated in the graphs of FIG. 43. To the THF/0.2% water solutions, more water was added such that the new solution was a THF/0.4% water solution. The corrosion probe 12 was inserted into the THF/0.4% water solution and 1.4, 1.8, 2.2 and 2.6 volts were signaled to the corrosion probe 12. The current in μa measured in response to each of these were respectively as follows: 0.15, 2.5, 3.0, and 3.5. The 0.4% water/current points were subsequently plotted on the graph of FIG. 43. More water was added to the THF/0.4% water solution to form a THF/0.8% water solution, and when the same set of voltages was signaled to the corrosion probe 12 after it was inserted into the THF/0.8% water solution, the following currents in μa were measured respectively in response to each of these voltages: 0.63, 0.87, 0.99, and 1.19. The 0.8% water/current points were plotted on the graph of FIG. 43, and a family of curves was constructed for each of the signaled voltages (i.e. 1.4 v, 1.8 v, 2.2 v, and 2.6 v) as illustrated in FIG. 43. Clearly, more curves could be generated if more voltages were signaled. The current (measured) at any voltage in FIG. 43 is higher where more water is present in the THF. The value of the current (measured) depends on the quantity of water added to the THF. Through the use of the family of curves of FIG. 43 and the corrosion probe 12, a THF/water solution may be tested to determine the exact amount of water contained within the THF/water solution. For example the corrosion probe 12 would be inserted into a THF/water solution, and one of the voltages (i.e. 1.4 v or 1.8 v or 2.2 v or 2.6 v) from the family of curves would be signaled. If 1.4 v was signaled to the corrosion probe 12 and the current in response to the 1.4 v measured about 3.8 μa, a point on the 1.4 v curve corresponding or aligning to 3.8 μa would be identified and plotted. If the plotted point on the 1.4 v curve corresponding to the 3.8 μa (of measured current) is point "a" on the graph in FIG. 43, then the point on the horizontal axis (i.e. the abscissa) of the graph labeled "% H$_2$O in Tetrahydrofuran (THF)" which corresponds with point "a" would be 0.6, indicating that 0.6% water is contained within the THF/water solution. To verify this finding, the remaining voltages (i.e. 1.8 v and 2.2 v and 2.6 v) from the family of curves would be signaled and the respective currents in response from each of these voltages would be identified; and the point on each of the remaining voltage curves corresponding to the respective currents would be identified and plotted. If the plotted points on the 1.8 v, 2.2 v and 2.6 v curves corresponding to the respective measured currents are point "b", point "c", and point "d", respectively (as labelled on the graph in FIG. 43), then the point on the horizontal axis of the graph corresponding with these points would be 0.6%, indicating and verifying that the THF/water solution indeed contains 0.6% water. Thus, the corrosion probe 12 of this invention can generate a family of calibration curves that may be used to detect and measure the exact amount of water contained within a THF/water solution.

EXAMPLE XVIII

Figure 44:
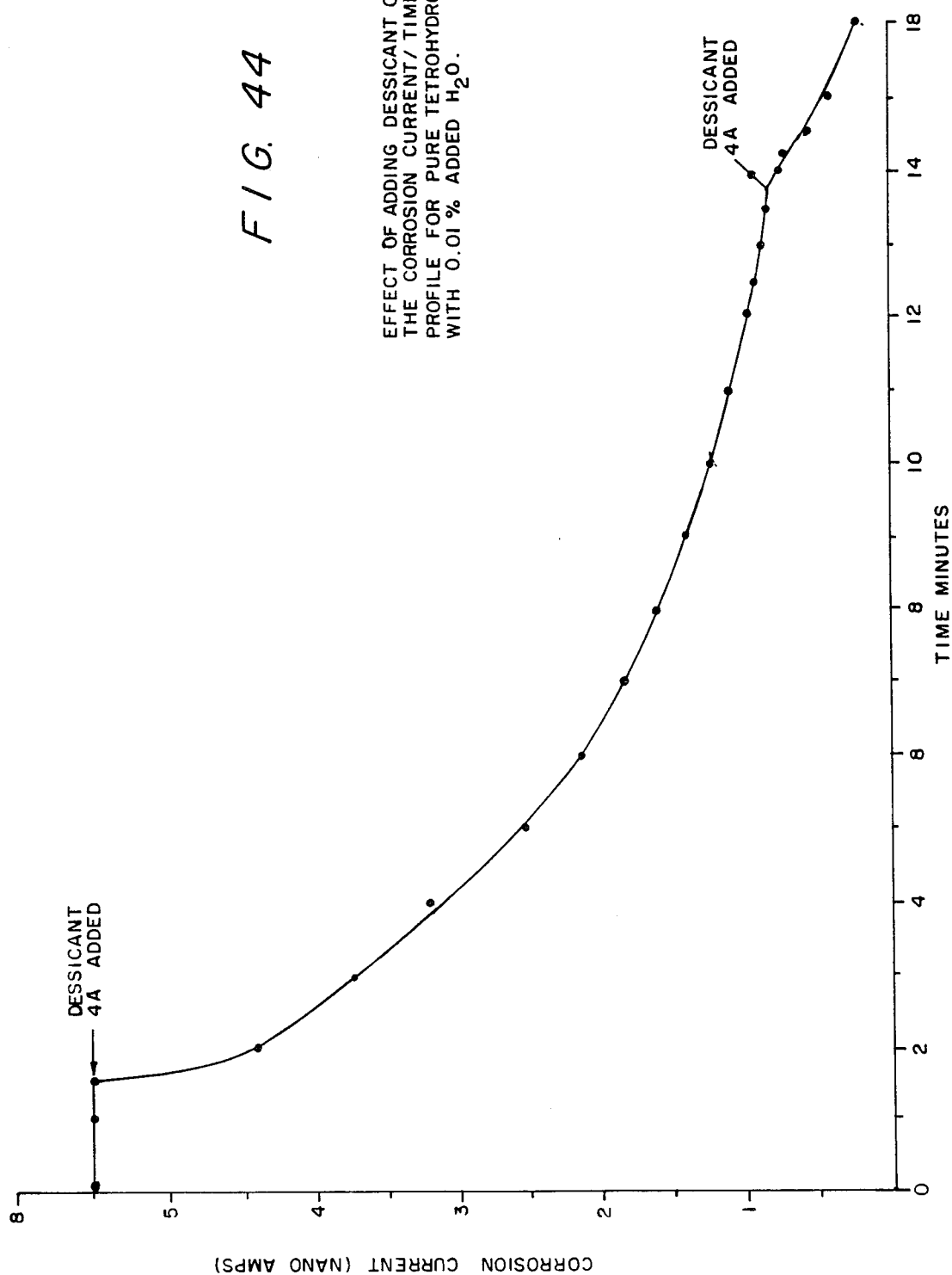
FIG. 44 is a curve of pure THF containing 0.01% added water decreasing in measured current with time after a dessicant (Linde 4A Molecular Sieves) was added to the THF solution.

The same electrodes and configuration described in Example XV were immersed in pure THF containing 0.01% added water. A constant voltage of 2.5 volts was applied to the corrosion probe 12. After two minutes a dessicant was added to the fluid (Linde 4A Molecular Sieves). The current as a function of time is shown in FIG. 44; after nominally 14 minutes additional dessicant was added. The decrease in signal (current) with time shown in FIG. 44 resulted from the removal of water from THF by the dessicant. Clearly the corrosion probe 12 does sense the presence of electroactive water in an electrically insulating fluid which in this instance was THF.

EXAMPLE XIX

Figure 45:
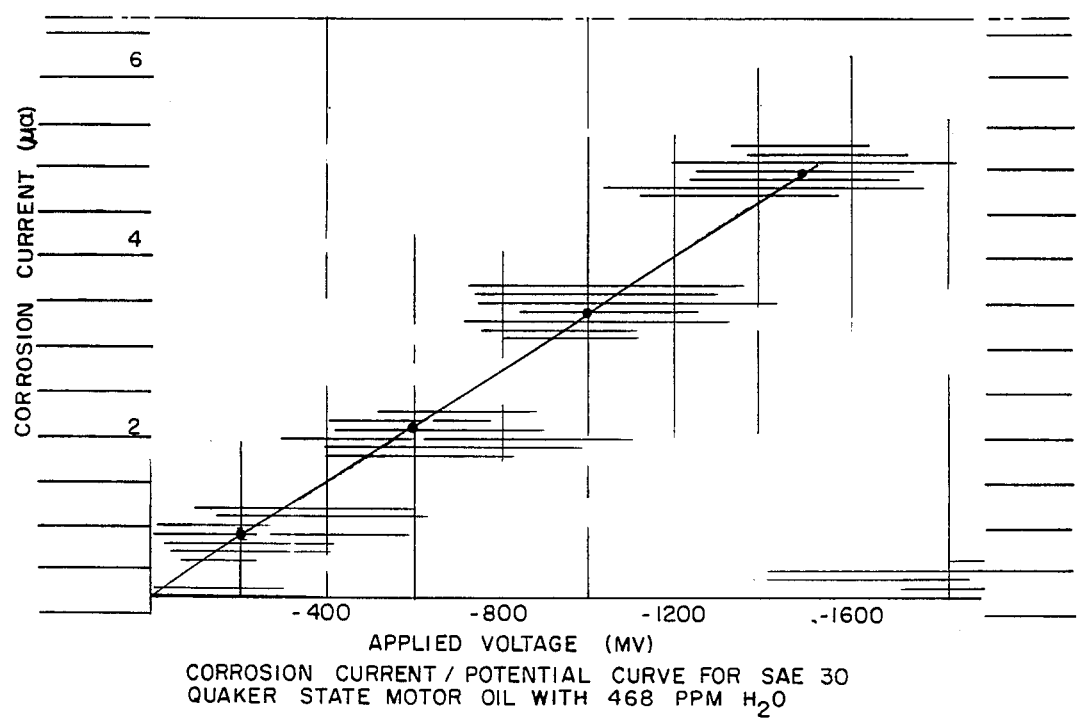
FIG. 45 is a graph representing signal currents measured as a function of applied potential at a fixed concentration of water in lube oil.

This invention was demonstrated with an amperometric analysis for water in motor oil (i.e. specifically Quaker State SAE 30) using the corrosion probe 12 described in Example XV. Shown in FIG. 45 are the signal currents measured as a function of applied voltage for a fixed concentration of added water, in this example 468 ppm H$_2$O. The larger the applied potential, the larger the signal current that is measured with a fixed concentration of water.

EXAMPLE XX

Figure 46:
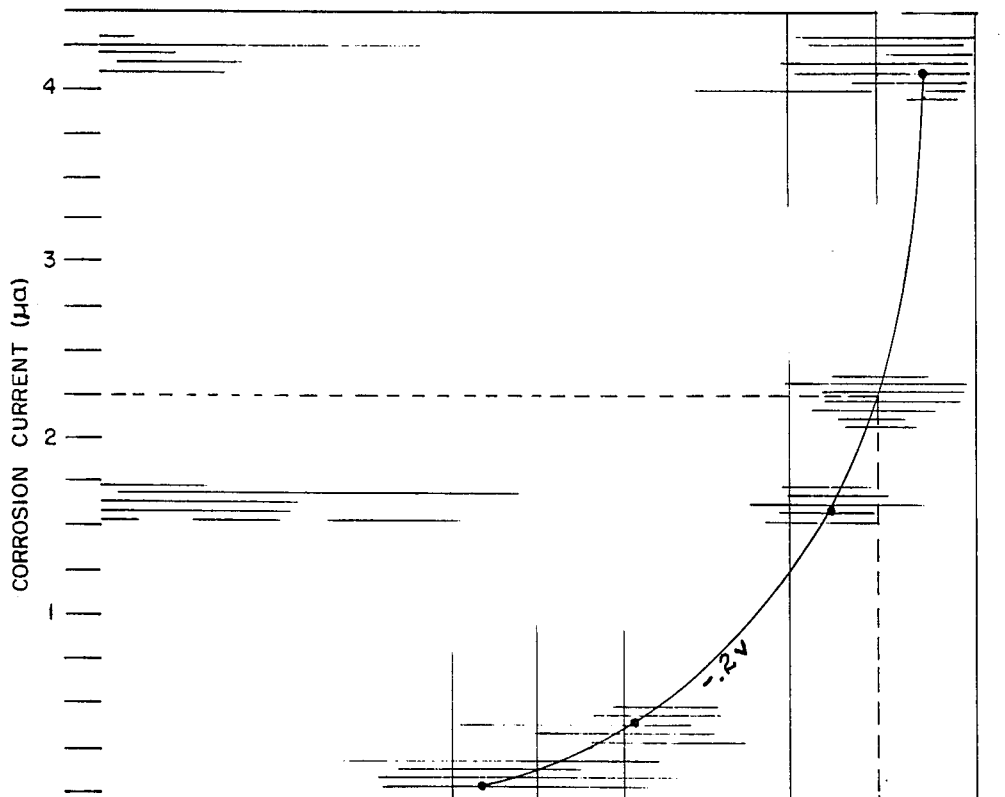
FIG. 46 is a graph of −0.2 v constant voltage curve plotted on a graph of ppm concentration of water in lube oil vs. measured current and illustrates the dependencies of current signal on the amount of water at a fixed applied potential.

In another test using the motor oil of Example XIX, a sufficient quantity of water was added such that the oil/water solution comprised about 430 ppm H$_2$O. A constant voltage of $-0.2$ v. was applied to the corrosion probe 12 after it was inserted into the oil/water solution comprising 430 ppm H$_2$O. The current in response to $-0.2$ v. was 0.1 μa. More water was added to the motor oil such that the oil/water solution comprised about 620 ppm H$_2$O). Approximately $-0.2$ v was signaled to the probe 12 again, and about 0.4 μa of current was measured in response to the $-0.2$ v. Still more water was added until the oil/water solution comprised about 840 ppm H$_2$O. In response to another $-0.2$ v. applied to the inserted corrosion probe 12, 1.5 μa of current was measured. More water was added to the motor oil such that the oil/water solution comprised about 950 ppm H$_2$O. After about $-0.2$ v. was signaled to corrosion probe 12 subsequent to inserting it into the oil/water solution comprising about 950 ppm H$_2$O, about 4.2 μa was measured in response thereto. The resulting curve is shown in FIG. 46 and illustrates the dependencies of measured current on the amount of water present in the motor oil at a fixed applied potential (i.e. $-0.2$ v). Such a curve may be employed along with the corrosion probe 12 to determine the amount of water in a given motor oil solution. For example, when a known $-0.2$ v. is applied to the corrosion probe 12 after it is inserted into a given solution of motor oil/water whose water content is to be determined, a signal current may be measured in response to this $-0.2$ v. signaled potential. The particular amount (ppm) of water corresponding to the measured current on the $-0.2$ v. curve in FIG. 46 represents the amount of water in the motor oil. Thus, if the measured current in response to an applied $-0.2$ v. to a corrosion probe 12 within a motor oil/water solution (whose water content is to be determined) is about 2.5 μa, then the corresponding ppm H$_2$O to this measured current (see dotted lines in FIG. 46) is about 900 ppm. This would indicate that the amount of water in the motor oil/water solution is 900 ppm.

EXAMPLE XXI

Figure 47:
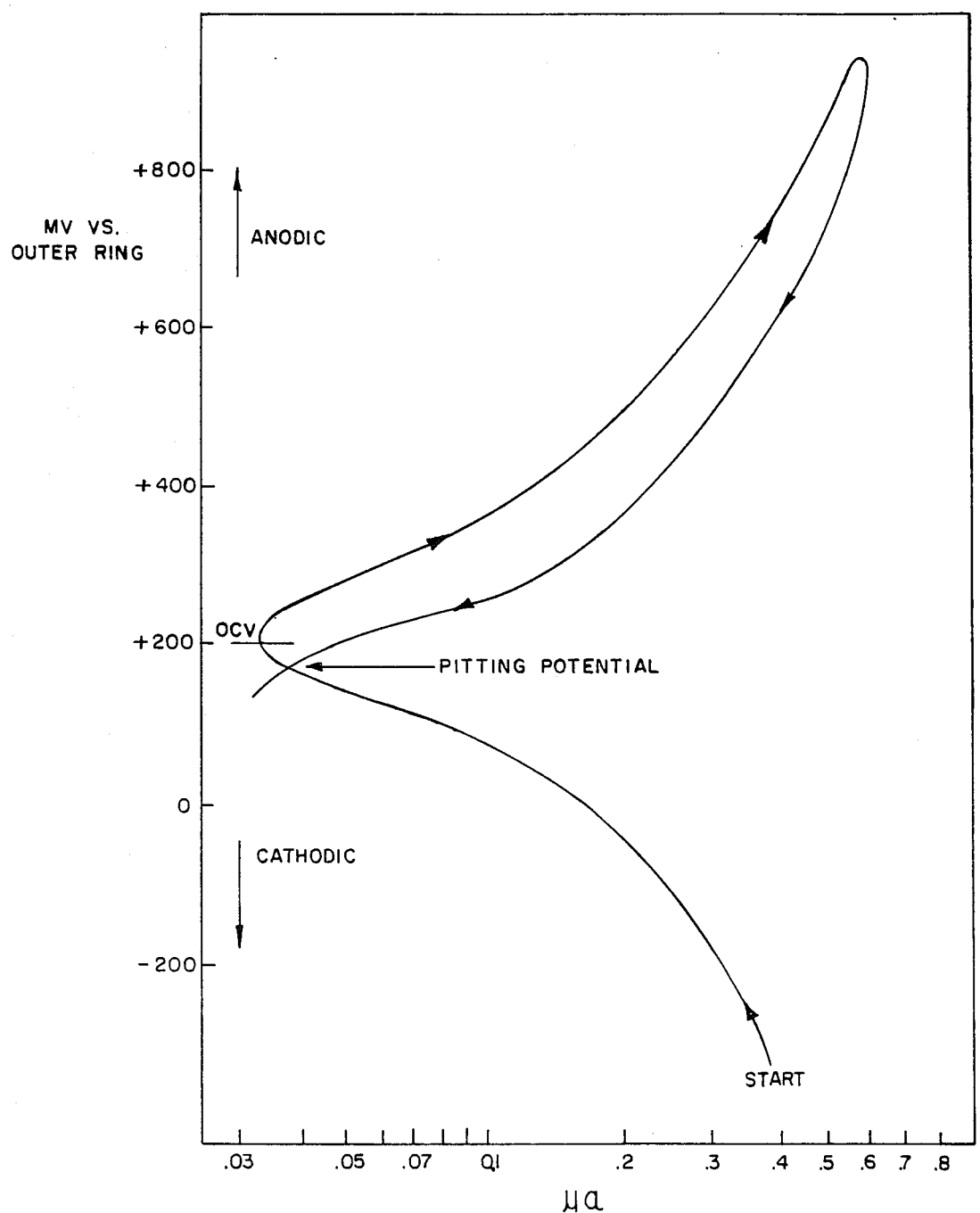
FIG. 47 is a curve of a cyclic voltammetry conducted with the corrosion probe for a low alloy carbon steel electrode in a mixture of crude oil containing 40% by volume brine and 760 psig. $CO_2$.

The corrosion probe 12 of this invention may be used in an electroanalytical technique known as "cyclic voltametry". The potential applied to the working electrode 16 is changed rapidly with time, e.g. 100 millivolts per second, generally in a linear manner from one prechosen value to another prechosen value and then back to the original prechosen value. The current-potential pattern resulting can provide information about the fluid phase and/or about the electrode material. One such cyclic voltammetric experiment carried out with the corrosion probe 12 is illustrated in FIG. 47 for a low alloy carbon steel electrode in a mixture of highly resistive crude oil containing 40% by volume brine and 760 psig. $CO_2$ (This mixture thus contained current-carrying ions, but because of rapid mixing (stirring at 1000 rpm), the ionically conductive water phase was dispersed as isolated droplets throughout the continuous crude oil phase. The mixture was therefore poorly conductive ; the ohmic resistance measured between the working and reference electrodes was in excess of 1 megohm.) The steel working electrode 16 potential was initially −400 mv and was increased continuously at 100 mv/sec to +900 mv and then decreased at the same rate to +100 mv. The current pattern (FIG. 47) shows that at potentials less than +200 mv, steel of this particular composition, will not corrode (the current was cathodic). The fact that the +900 mv-to-+100 mv scan intersects the −400 mv-to- +900 mv scan where it does, implies that this steel surface is prone to generate pits as part of the spontaneous corrosion process at +200 mv.

EXAMPLE XXII

The test medium was 1000 ml of crude oil with 5% (by volume) brine phase (4% NaCl) in an autoclave 15 stirred at 1000 rpm with N80 steel coupons, under 760 psig $CO_2$ at 186° F. The dielectric material 22 in the probe was an epoxy resin and was not ionically conductive. The ohmic resistance between the sample 16 and reference electrodes 18 was in the range of 5.7 to 8.7 megohms under these experimental conditions. The surfactant was the WITCO product WITCONATE "P10-59", an oil soluble ionic amine alkyl-aryl lauryl sulfonate. The probe 12 was first dipped in this material, the excess surfactant fluid rinsed off with water and the probe 12 placed into the autoclave 15. The open circuit potentials were stable, indicative of a functioning ionically conductive dielectric surface 23. Stable corrosion rates were measurable, as for example:

| Time  | $I_c$ (microamps) | Volts  | Mils Per Year |
|-------|-------------------|--------|---------------|
| 7 min | 0.0               | −.0027 |               |
|       | −20               | −.178  | 17            |

The corrosion rate-time relationship measured was:

| Time  | mpy   |
|-------|-------|
| 0     | 5,540 |
| 5 min | 168   |
| 7     | 17    |
| 15    | 11    |
| 166   | 13    |

This probe 12 was replaced by a probe 12 having the embodiment of FIGS. 2–11 and activated in accordance with an etchant of Table I. The corrosion rate so measured was 16 mpy, essentially the same value as found with the surfactant activated probe 12. The sample-reference electrode resistance for the surfactant activated probe 12 was 0.1 megohm in the test medium After grinding off the surface, the ohmic resistance was 5.7 megohm and the open circuit potentials were very unstable; and electrochemical corrosion rate measurements were not possible. These results confirm that the surfactant did indeed activate the surface of the dielectric 22 and the data was not due to the injection of surfactant into the fluid phase.

EXAMPLE XXIII

The test medium and conditions were the same as described in EXAMPLE XXII. The surfactant was a GAF product "IGEPAL" C0 170, an oil-soluble nonionic ethoxylated alkylphenol surfactant of the nonylphenol family. The inactive epoxy dielectric probe was dipped into this material, the excess washed off and the probe placed into the autoclave. Again the open circuit potentials were stable and corrosion rates could be measured by electrochemical means, as for example:

| Time   | $I_c$ (microamps) | Volts   | Mils Per Year |
|--------|-------------------|---------|---------------|
| 50 min | 0.0               | −.0006  |               |
|        | 2                 | −.0478  | 7             |

The corrosion rate-time relationship measured was:

| Time  | mpy |
|-------|-----|
| 5 min | 544 |
| 35    | 60  |
| 50    | 7   |

It is to be concluded that nonionic surfactants will also activate the probe.

While the present invention has been described herein with reference to particular embodiments thereof and examples therefor, a latitude of modification, various changes and substitutions are intended in the foregoing disclosure and it will be appreciated that in some instances some features of the invention will be employed without a corresponding use of other features without departing from the scope of the invention as set forth. For example, in the embodiment of the corrosion probe 12 in FIGS. 48–51, the function of the reference electrode 18 is not needed, but is replaced by the counter electrode 20. Stated alternatively, the corrosion probe 12 would comprise only two electrodes (i.e. working electrode 16 and counter electrode 20, with no reference electrode 18) with the dielectric 22 therebetween having the ionically conductive dielectric surface 23. With respect to this embodiment of the invention, working electrode 16 and counter electrode 20 are separated by the dielectric 22 having the ionically conductive dielectric surface 23. Counter electrode 20 may occupy the center position as illustrated in FIG. 49, or working electrode 16 may occupy the center position with the counter electrode 20 surrounding the working electrode 16 as illustrated in FIGS. 50 and 51. In addition to the working electrode 16, the counter electrode 20, and the dielectric 22 with the ionically conductive dielectric surface 23 therebetween, corrosion probe 12 of this embodiment of the invention may include the sheath 30 that terminates into the sheath end 32 (see FIGS. 50 and 51). The dielectric 22 or any similar matter or material without the ionically conductive surface 23 may be positioned between the counter electrode 20 and the sheath 30. The working electrode 16 and the counter electrode 20 terminate into the working electrode end 24 and the counter electrode end 28, respectively. Depending conductors 34 and 38 respectively connect to the opposed ends 52 and 56 of the working electrode end 24 and the counter electrode end 28. The procedure to find the corrosion rate upon the working electrode 16 in the corrosive liquid environment with this embodiment of the corrosion probe 12 comprises applying a constant current between the working electrode 16 and the counter electrode 20, and the polarization $\Delta\phi$ of the working electrode 16 (versus the reference electrode) is measured. The corrosion rate is calculated by dividing a conversion factor K (which depends on Tafel slopes, polarization $\Delta\phi$ and electrode area) by the polrization $\Delta\phi$. This procedure, as well as the other procedure(s) to determine corrosion rate(s) upon the working electrode(s) 16, is more particularly described in an article entitled "Electrical and Electrochemical Methods for Determining Corrosion Rates" published in 1984 by the Technical Committee of the National Association of Corrosion Engineers, Houston, Tex. (article No. T-3L-3(TCR) D52 R1 pd). This article, as well as all of the bibliography and/or references that are contained in this article, are incorporated entirely herein by reference.

Similarly, in a more broader aspect of the present invention, any of the embodiments of the corrosion probe 12 can be connected electrically to any device 39 or any potential change selecting means (well known to those possessing ordinary skill in the art, such as direct current power supplies, potentiometer, etc.) for selecting and maintaining a desired change in potential of the working electrode 16 with respect to the reference electrode 18 by causing a current to flow, in response to the selected desired change in potential, through the working electrode 16 and the counter electrode 20 (or the current conductive means) of a magnitude sufficient to effect the selected desired change in potential of the working electrode 16 with respect to the reference electrode 18. A current measuring means (e.g. meter 48) can measure the magnitude of the current which was caused to flow through the working electrode means. The corrosion rate upon the working electrode 16 may now be determined in accordance with any of the previously mentioned procedures, including those procedures described in the article entitled "Electrical and Electrochemical Methods for Determining Corrosion Rates". Likewise, any of the embodiments of the corrosion probe 12 can be connected electrically to any device 39 or any current selecting means (well known to those possessing ordinary skill in the art, such as direct current power supplies, potentiometer, etc.) for selecting and maintaining a desired current flow through the working electrode 16 and the counter electrode 20 (or the current conductive means). A difference in potential measuring means (e.g. voltmeter 50) can measure the magnitude of a difference in potential between the working electrode 16 and the reference electrode 18; and the corrosion rate upon the working electrode 16 can subsequently be found in accordance with any of the previously mentioned procedures.

While various embodiments of the invention have been described, it will be understood that the embodiments are capable of many further modifications and this application is intended to cover any variations, uses, or adaptions of the invention following in general, the principles of the invention and including such departures from the present disclosure as come within knowledge or customary practice in the art to which the invention pertains, and as may be applied to the essential features hereinbefore set forth and fall within the scope of the invention or the limits of the appended claims.

I claim:

1. An apparatus for measuring the corrosion rates of metals in a corrosive liquid environment, comprising in combination at least one first electrode means having a first depending conductor means connected thereto; at least one second electrode means having a second depending conductor means connected thereto; at least one third electrode means having a third depending conductor means connected thereto; a dielectric means positioned between each of the first and second electrode means and between each of the second and the third electrode means, said dielectric means having an ionically conductive surface; at least one means electrically engaged to each of said first, second and third depending conductor means for applying a difference in potential between the first electrode means and the second electrode means; at least one means for measuring the current being conducted through the first electrode means and the third electrode means.

2. The apparatus of claim 1 wherein each of said first, said second, and said third electrode means respectively terminates into a first, a second, and a third electrode end means, each of said electrode end means is substantially in a coplanar relationship among and with respect to each other, said means for applying a difference in potential is a potentiostat means; and at least one means for signaling to the potentiostat means the difference in potential which is to be applied by the same.

3. A process for measuring the corrosion rates of metals in a corrosive liquid environment, comprising the steps of:
 (a) inserting a corrosion probe means into a corrosive liquid environment;
 (b) attaching electrically to a means for applying a difference in potential the corrosion probe means comprising in integral combination at least one first, at least one second, and at least one third electrode means; a dielectric means having an ionically conductive surface and positioned between the first and second electrode means and between the second and third electrode means; a predetermined ohmic resistance between the first and second electrode means; and a predetermined electromotive force between said second electrode means and an area in the surrounding corrosive liquid environment in general microscopic proximity thereto;
 (c) applying with said means for applying a difference in potential a predetermined difference in potential between the first electrode means and the second electrode means;
 (d) measuring simultaneously with step (c) a current being conducted through the first electrode means, over the ionic dielectric surface between the first electrode means and the third electrode means, and through the third electrode means back to the means for applying a difference in potential;
 (e) calculating from the measured current of step (d) and the predetermined ohmic resistance of step (b) an electromotive force between an area in the corrosive liquid environment in general microscopic proximity to the first electrode means and an area in the corrosive liquid environment in general microscopic proximity to the second electrode means;
 (f) determining an electromotive force between the first electrode means and an area in the corrosive liquid environment in general microscopic proximity to the first electrode means by subtracting from the predetermined difference in potential of step (c), the electromotive force of step (e) and the predetermined electromotive force of step (b); and (g) computing a corrosion current on the first electrode means from the determined electromotive force of step (f) and the measured current of step (d).

4. A process for measuring the corrosion rates of metals in a corrosive liquid environment, comprising the steps of:

(a) inserting a corrosion probe means into a corrosive liquid environment;

(b) attaching electrically to a means for applying a difference in potential the corrosion probe means comprising in integral combination at least one first, at least one second, and at least one third electrode means; a dielectric means having an ionically conductive surface and positioned between the first and second electrode means and between the second and third electrode means; a predetermined ohmic resistance between the first and second electrode means; and a predetermined electromotive force between said second electrode means and an area in the surrounding corrosive liquid environment in general microscopic proximity thereto;

(c) applying with said means for applying a difference in potential a first predetermined difference in potential between the first electrode means, and the second electrode means;

(d) measuring simultaneously with step (c) a current being conducted through the first electrode means, over the ionic dielectric surface between the first electrode means and the third electrode means, and through the third electrode means back to the means for applying a difference in potential;

(e) calculating from the measured current of step (d) and the predetermined ohmic resistance of step (b) an electromotive force between an area in the corrosive liquid environment in general microscopic proximity to the first electrode means and an area in the corrosive liquid environment in general microscopic proximity to the second electrode means;

(f) determining an electromotive force between the first electrode means and an area in the corrosive liquid environment in general microscopic proximity to the first electrode means by subtracting from the predetermined difference in potential of step (c), the electromotive force of step (e) and the predetermined electromotive force of step (b);

(g) repeating steps (c) through (f) with a second predetermined difference in potential to measure a second current and to determine a second electromotive force; and (h) computing a corrosion current on the first electrode means from the electromotive force of step (f) and the measured current of step (d) and from the second electromotive force of step (g) and the second measured current.

5. A process for measuring the corrosion rates o metals in a corrosive liquid environment, comprising the steps of:

(a) inserting a corrosion probe means into a corrosive liquid environment;

(b) attaching electrically to a means for applying a difference in potential the corrosion probe means comprising in integral combination at least one first, at least one second, and at least one third electrode means; a dielectric means having an ionically conductive surface and positioned between the first and second electrode means and between the second and third electrode means; a predetermined ohmic resistance between the first and second electrode means; and a predetermined electromotive force between said second electrode means and an area in the surrounding corrosive liquid environment in general microscopic proximity thereto;

(c) applying with said means for applying a difference in potential a first predetermined difference in potential between the first electrode means and the second electrode means;

(d) measuring simultaneously with step (c) a current being conducted through the first electrode means, over the ionic dielectric surface between the first electrode means and the third electrode means, and through the third electrode means back to the means for applying a difference in potential;

(e) calculating from the measured current of step (d) and the predetermined ohmic resistance of step (b) an electromotive force between an area in the corrosive liquid environment in general microscopic proximity to the first electrode means and an area in the corrosive liquid environment in general microscopic proximity to the second electrode means;

(f) determining an electromotive force between the first electrode mean and an area in the corrosive liquid environment in general microscopic proximity to the first electrode means by subtracting from the predetermined difference in potential of step (c), the electromotive force of step (e) and the predetermined electromotive force of step (b);

(g) repeating steps (c) through (f) with a second predetermined difference in potential to measure a second current and to determine a second electromotive force;

(h) repeating steps (c) through (f) with a third predetermined difference in potential to measure a third current and to determined a third electromotive force; and (i) computing a corrosion current on the first electrode means from the electromotive force of step (f) and the measured current of step (d), from the second electromotive force of step (g) and the second measured current, and from the third electromotive force of step (h) and the third measured current.

6. An apparatus for measuring the corrosion rats of metals in a corrosive liquid environment, comprising a first electrode means having a first depending conductor means connected thereto; a second electrode means having a second depending conductor means connected thereto; a dielectric means positioned between the first and the second electrode means, said dielectric means having an ionically conductive surface; a current conductive means having a third depending conductor means connected thereto; and at least one means electrically engaged to said first, said second and said third conductor means for applying a difference to potential between the second electrode means and the first electrode means; at least one means for measuring a current being conducted through the first electrode means, through the corrosive liquid environment, and through the current conductive means.

7. The apparatus of claim 6 wherein said first and said second electrode means, respectively, terminate in a first and a second electrode end means, said first and said second electrode end means are substantially in a coplanar relationship among and with respect to each other.

8. An apparatus for measuring the corrosion rates of metal in a corrosive liquid environment, comprising in combination a first electrode means having a first depending conductor means connected thereto; a second electrode means having a second depending conductor means connected thereto; a third electrode means having a third depending conductor means connected thereto; a dielectric means positioned between the first and the second electrode means and between the second and the third electrode means, said dielectric means between said first and said second electrode means having an ionically conductive surface; at least one means electrically engaged to said first, said second, and said third depending conductor means for applying a difference in potential between the second electrode means and the first electrode means; at least one means for measuring current being conducted through the second electrode means, through the corrosive liquid environment, and through the third electrode means.

9. The apparatus of claim 8 wherein said first, said second, and said third electrode means, respectively, terminate in a first, a second, and a third electrode end means, said first and said second electrode end means are substantially in a coplanar relationship among and with respect to each other.

10. A process of measuring the corrosion rates of metal in a corrosive liquid environment, comprising the steps of:
 (a) inserting a corrosion probe means into a corrosive liquid environment;
 (b) attaching electrically to a means for applying a difference in potential the corrosion probe means comprising a first electrode means, a second electrode means, and a current conductive means; a dielectric mean having an ionically conductive surface and postioned between the first and second electrode means; and a predetermined electromotive force between said first electrode means and an area in the surrounding corrosive liquid environment in general microscopic proximity thereto;
 (c) applying with said means for applying a difference in potential a predetermined difference in potential between the second electrode means and the first electrode means;
 (d) measuring simultaneously with step (c) a current being conducted through the second electrode means, through the corrosive liquid environment, and through the current conductive means back to the means for applying a difference in potential;
 (e) determining an electromotive force between the second electrode means and an area in the corrosive liquid environment in general microscopic proximity to the second electrode means by subtracting from the predetermined difference in potential of step (c), the predetermined electromotive force of step (b); and
 (f) computing a corrosion current on the second electrode means from the determined electromotive force of step (e) and the measured current of step (d).

11. A process for measuring the corrosion rates of metals in a corrosive liquid environment, comprising the steps of:
 (a) inserting a corrosion probe means into a corrosive liquid environment;
 (b) attaching electrically to a means for applying a difference in potential the corrosion probe means comprising a first electrode means, a second electrode means, and a current conductive means; a dielectric means having an ionically conductive surface and postioned between the first and second electrode means; and a predetermined electromotive force between said first electrode means and an area in the surrounding corrosive liquid environment in general microscopic proximity thereto;
 (c) applying with said means for applying a difference in potential a predetermined difference in potential between the second electrode means and the first electrode means;
 (d) measuring simultaneously with step (c) a current being conducted through the second electrode means, through the corrosive liquid environment, and through the current conductive means back to the means for applying a difference in potential;
 (e) determining an electromotive force between the second electrode means and an area in the corrosive liquid environment in general microscopic proximity to the second electrode means by subtracting from the predetermined difference in potential of step (c) the predetermined electromotive force of step (b);
 (f) repeating steps (c) through (e) with a second predetermined difference in potential to measure a second current and to determine a second electromotive force; and
 (g) computing a corrosion current on the second electrode means from the electromotive force of step (e) and the measured current of step (d) and from the second electromotive force of step (f) and the second measured current.

12. A process for measuring the corrosion rates of metal in a corrosive liquid environment, comprising the steps of:
 (a) inserting a corrosion probe means into a corrosive liquid environment;
 (b) attaching electrically to a means for applying a difference in potential the corrosion probe means comprising a first electrode means, a second electrode means, and a current conductive means; a dielectric means having an ionically conductive surface and positioned between the first and the second electrode means; and a predetermined electromotive force between the first electrode means and an area in the surrounding corrosive liquid environment in general microscopic proximity thereto;
 (c) applying with said means for applying a difference in potential a first predetermined difference in potential between the second electrode means and the first electrode means;
 (d) measuring simultaneously with step (c) a current being conducted through the second electrode means, through the current conductive means back to the means for applying a difference in potential;
 (e) determining an electromotive force between the second electrode means and an area in the corrosive liquid environment in general microscopic proximity to the second electrode means by subtracting from the predetermined difference in potential of step (c) the predetermined electromotive force of step (b);
 (f) repeating steps (c) through (e) with a second predetermined difference in potential to measure a second current and to determine a second electromotive force;

(g) repeating steps (c) through (e) with a third predetermined difference in potential to measure a third current and to determined a third electromotive force; and computing a corrosion current on the second electrode means from the electromotive force of step (e) and the measured current of step (d), form the second electromotive force of step (f) and the second measured current, and from the third electromotive force of step (g) and the third measured current.

13. A process for measuring the corrosion rates of metals in a corrosive liquid environment, comprising the steps of:

(a) inserting a corrosion probe means into a corrosive liquid environment;

(b) attaching electrically to a means for applying a difference in potential the corrosion probe means comprising in combination a first electrode means, a second electrode means, and a third electrode means; a dielectric means positioned between the first and second electrode means and between a second and a third electrode means; said dielectric means between the first and the second electrode means having an ionically conductive surface; and a predetermined electromotive force between the first electrode means and an area in the surrounding corrosive liquid environment in general microscopic proximity thereto;

(c) applying with said means for applying a difference in potential a predetermined difference in potential between the second electrode means and the first electrode means;

(d) measuring simultaneously with step (c) a current being conducted through the second electrode means, through the corrosive liquid environment, and through the third electrode means back to the means for applying a difference in potential;

(e) determining an electromotive force between the second electrode means and an area in the corrosive liquid environment in general microscopic proximity to the first electrode means by subtracting from the predetermined difference in potential of step (c) the predetermined electromotive force of step (b); and (f) computing a corrosion current on the second electrode means from the determined electromotive force of step (e) and the measured current of step (d).

14. A process for measuring the corrosion rates of metal in a corrosive liquid environment, comprising the steps of:

(a) inserting a corrosion probe means into a corrosive liquid environment;

(b) attaching electrically to a means for applying a difference in potential the corrosion probe means comprising in combination a first electrode means, a second electrode means, and a third electrode means; a dielectric means positioned between the first and the second electrode means and between the second and a third electrode means; said dielectric means between the first and second electrode means having an ionically conductive surface; and a predetermined electromotive force between the first electrode means and an area in the surrounding corrosive liquid environment in general microscopic proximity thereto;

(c) applying with said means for applying a difference in potential a first predetermined difference in potential between the second electrode means and the first electrode means;

(d) measuring simultaneously with step (c) a current being conducted through the second electrode means, through the corrosive liquid environment, and through the third electrode means back to the means for applying a difference in potential;

(e) determining an electromotive force between the second electrode means and an area in the corrosive liquid environment in general microscopic proximity to the second electrode means by subtracting from the predetermined difference in potential of step (c) the predetermined electromotive force of step (b);

(f) repeating steps (c) through (e) with a second predetermined difference in potential to measure a second current and to determine a second electromotive force; and (g) Computing a corrosion current on the second electrode means from the electromotive force of step (e) and the measured current of step (d) and from the second electromotive force of step (g) and the second measured current.

15. A process of measuring the corrosion rates of metals in a corrosive liquid environment, comprising the steps of:

(a) inserting a corrosion probe means into a corrosive liquid environment;

(b) attaching electrically to a means for applying a difference in potential the corrosion probe means comprising in combination a first electrode means, a second electrode means, and a third electrode means; a dielectric means positioned between the first and the second electrode means and between the second and the third electrode means; said dielectric means positioned between the first and second electrode means having an ionically conductive surface; and a predetermined electromotive force between the first electrode means and an area in the surrounding corrosive liquid environment in general microscopic proximity thereto; potential a first predetermined difference in potential between the second electrode means and the first electrode means;

(d) measuring simultaneously with step (c) a current being conducted through the second electrode means, through the corrosive liquid environment, and through the third electrode means back to the means for applying a difference in potential;

(e) determining an electromotive force between the second electrode means and an area in the corrosive liquid environment in general microscopic proximity to the second electrode means by subtracting from the predetermined difference in potential of step (c) the predetermined electromotive force of step (b);

(f) repeating steps (c) through (e) with a second predetermined difference in potential to measure a second current and to determine a second electromotive force;

(g) repeating steps (c) through (e) with a third predetermined difference in potential to measure a third current and to determine a third electromotive force; and (h) computing a corrosion current on the second electrode means from the electromotive force of step (e) and the measured current of step (d), from the second electromotive force of step (f) and the second measured current, and from the third electromotive force of step (g) and the third measured current.

16. A process for measuring the corrosion rates of metal in a corrosive liquid environment, comprising the steps of:
(a) inserting a corrosion probe means into a corrosive liquid environment;
(b) attaching electrically to a means for applying a difference in potential the corrosion probe means comprising in integral combination at least one first, at least one second, and at least one third electrode means; a dielectric mean having an ionically conductive surface and positioned between the first and second electrode means and between the second and third electrode means;
(c) determining an ohmic resistance between the first and second electrode means;
(d) applying with said means for applying a difference in potential a predetermined difference in potential between the first electrode means and the second electrode means;
(e) measuring simultaneously with step (d) a current being conducted through the first electrode means, over the ionic dielectric surface between the first electrode means and the third electric means, and through the third electrode means back to the means for applying a difference in potential;
(f) calculating from the measured current of step (e) and the determined ohmic resistance of step (c) an electromotive force between an area in the corrosive liquid environment in general microscopic proximity to the first electrode means and an area in the corrosive liquid environment in general microscopic proximity to the second electrode means;
(g) determining an electromotive force between the first electrode means and an area in the corrosive liquid environment in general microscopic proximity to the first electrode means by subtracting from the predetermined difference in potential of step (d) the electromotive force of step (f); and
(h) computing a corrosion current on the first electrode means from the determined electromotive force of step (g) and the measured current of step (e).

* * * * *